United States Patent
Crawford et al.

(10) Patent No.: US 11,395,613 B2
(45) Date of Patent: Jul. 26, 2022

(54) MANUAL FLOW REGULATION FOR BLOOD COLLECTION

(71) Applicant: Becton, Dickinson and Company, Franklin Lakes, NJ (US)

(72) Inventors: Jamieson W. Crawford, Hagersten (SE); Craig Owen Russ, Wayne, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1 day.

(21) Appl. No.: 16/839,990

(22) Filed: Apr. 3, 2020

(65) Prior Publication Data

US 2020/0229745 A1     Jul. 23, 2020

Related U.S. Application Data

(63) Continuation of application No. 14/889,217, filed as application No. PCT/US2013/041156 on May 15, 2013, now Pat. No. 10,646,149.

(51) Int. Cl.
*A61B 5/15*     (2006.01)
*A61B 5/154*     (2006.01)
(Continued)

(52) U.S. Cl.
CPC .... *A61B 5/150946* (2013.01); *A61B 5/15003* (2013.01); *A61B 5/153* (2013.01); *A61B 5/154* (2013.01); *A61B 5/15074* (2013.01); *A61B 5/150221* (2013.01); *A61B 5/150259* (2013.01); *A61B 5/150389* (2013.01);
(Continued)

(58) Field of Classification Search
CPC .......... A61B 5/150946; A61B 5/15003; A61B 5/150221; A61B 5/150259; A61B 5/150389; A61B 5/150503; A61B 5/150572; A61B 5/150587; A61B 5/150717; A61B 5/150732; A61B 5/15074; A61B 5/150824; A61B 5/150992;
(Continued)

(56) References Cited

U.S. PATENT DOCUMENTS 2,848,999 A     8/1958     McGrew et al.
3,604,410 A     9/1971     Whitacre
(Continued)

FOREIGN PATENT DOCUMENTS

CN     102143774 A     8/2011
DE     10049295 C1     1/2002
(Continued)

*Primary Examiner* — Patrick Fernandes
(74) *Attorney, Agent, or Firm* — The Webb Law Firm

(57) ABSTRACT

A specimen collection assembly including a flow control member for adjustably altering a flow path is disclosed. In one configuration, the flow control member defines a regulation channel in fluid communication with a lumen of a cannula, wherein the flow control member is configured to adjustably alter an effective flow distance between the lumen of the cannula and an interior of an evacuated collection container. In another configuration, the flow control member is positioned to vary an effective cross-sectional area of at least one of an inlet port and an outlet port adapted to be in fluid communication with the lumen and the evacuated collection container.

9 Claims, 44 Drawing Sheets

(51) Int. Cl.
*A61M 5/168* (2006.01)
*A61M 1/00* (2006.01)
*A61B 5/153* (2006.01)
*A61M 39/24* (2006.01)

(52) U.S. Cl.
CPC .. *A61B 5/150503* (2013.01); *A61B 5/150572* (2013.01); *A61B 5/150587* (2013.01); *A61B 5/150717* (2013.01); *A61B 5/150732* (2013.01); *A61B 5/150824* (2013.01); *A61B 5/150992* (2013.01); *A61M 1/0003* (2013.01); *A61M 1/7413* (2021.05); *A61M 5/16813* (2013.01); *A61M 2039/2493* (2013.01)

(58) Field of Classification Search
CPC ...... A61B 5/153; A61B 5/154; A61M 1/7413; A61M 1/0003; A61M 5/16813; A61M 2039/2493
See application file for complete search history.

(56) References Cited

U.S. PATENT DOCUMENTS

| | | | |
|---|---|---|---|
| 3,848,579 A | 11/1974 | Villa-Real | |
| 3,848,581 A | 11/1974 | Cinqualbre et al. | |
| 3,877,465 A | 4/1975 | Miyake | |
| 4,073,288 A * | 2/1978 | Chapman | A61B 5/15003 600/578 |
| 4,409,991 A | 10/1983 | Eldridge | |
| 4,787,882 A | 11/1988 | Claren | |
| 4,972,843 A * | 11/1990 | Broden | A61B 5/150389 600/573 |
| 5,234,413 A | 8/1993 | Wonder et al. | |
| 5,269,768 A | 12/1993 | Cheung | |
| 6,506,165 B1 | 1/2003 | Sweeney | |
| 6,626,884 B1 | 9/2003 | Dillon et al. | |
| 9,174,007 B2 | 11/2015 | Lum et al. | |
| 2001/0025167 A1 | 9/2001 | Kraus et al. | |
| 2002/0049391 A1 | 4/2002 | Kuracina et al. | |
| 2003/0097097 A1 | 5/2003 | Scagliarini et al. | |
| 2003/0135164 A1 | 7/2003 | Simon | |
| 2005/0256447 A1 | 11/2005 | Richardson et al. | |
| 2007/0293828 A1 | 12/2007 | Lee | |
| 2011/0166525 A1 | 7/2011 | Tanabe et al. | |
| 2013/0116599 A1 | 5/2013 | Bullington et al. | |

FOREIGN PATENT DOCUMENTS

| | | |
|---|---|---|
| EP | 1312388 A1 | 5/2003 |
| EP | 1665986 A1 | 6/2006 |
| JP | S56109643 A | 8/1981 |
| JP | 2002325749 A | 11/2002 |
| JP | 2005323942 A | 11/2005 |
| WO | 9834532 A1 | 8/1998 |
| WO | 9948425 A1 | 9/1999 |
| WO | 03105942 A1 | 12/2003 |
| WO | 2012007614 A2 | 1/2012 |

\* cited by examiner

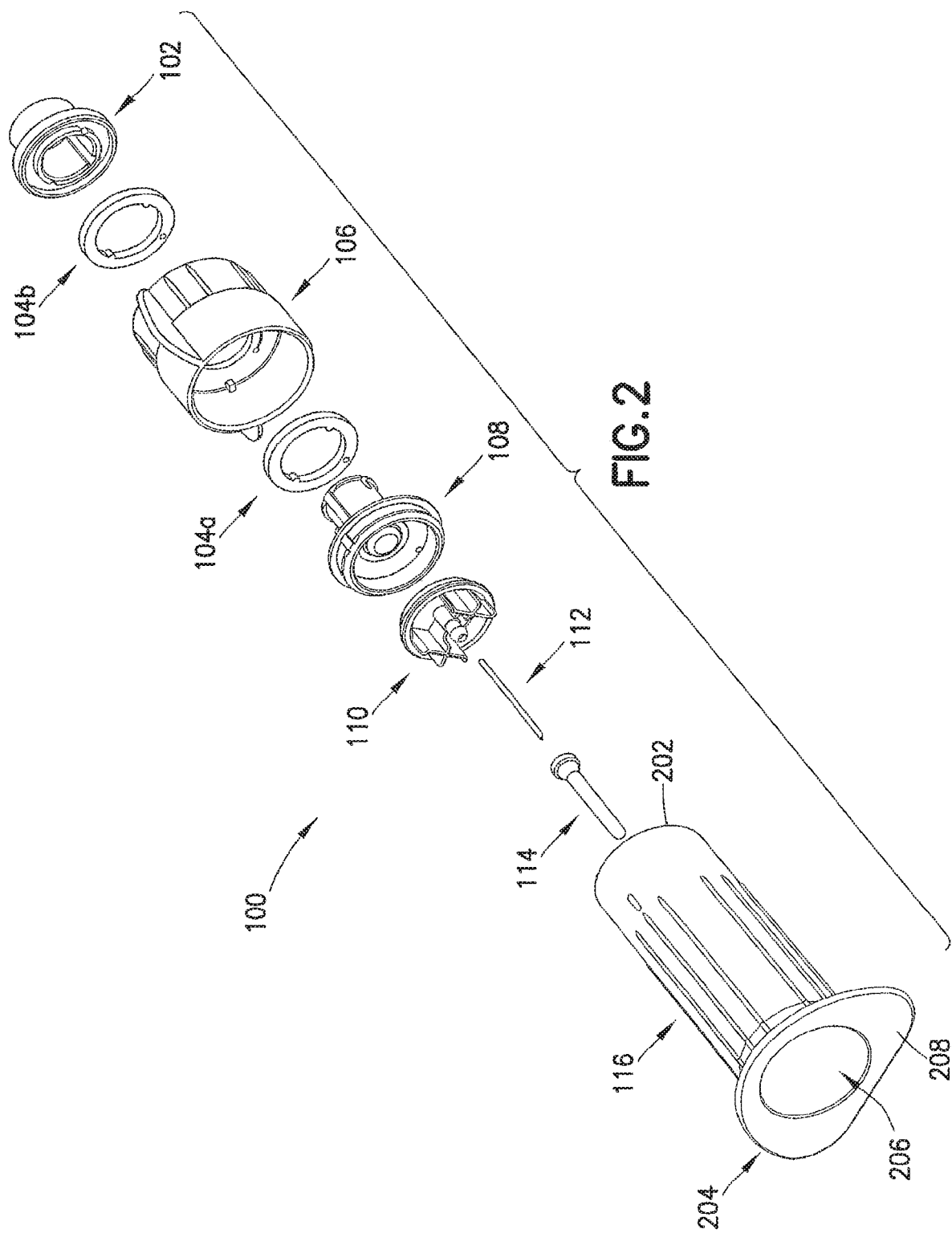

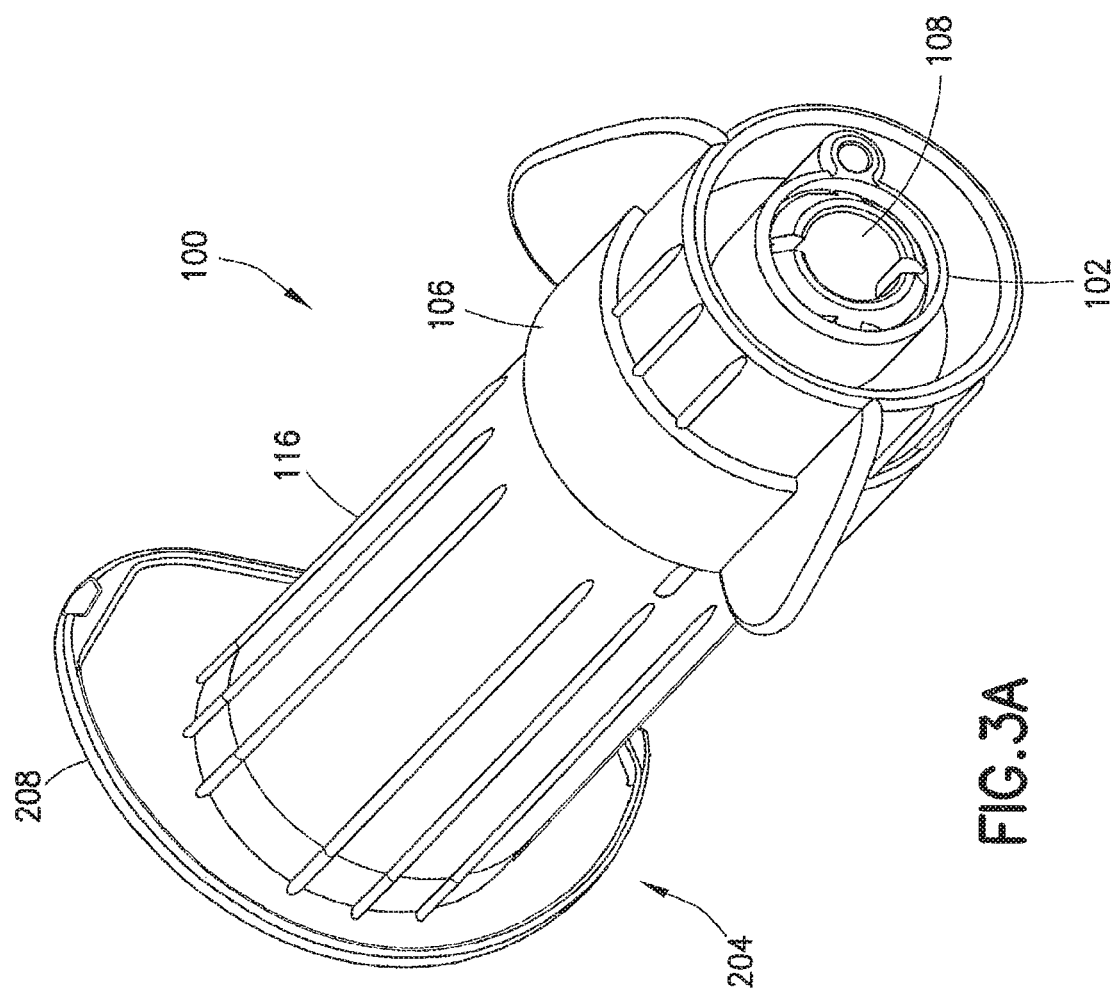

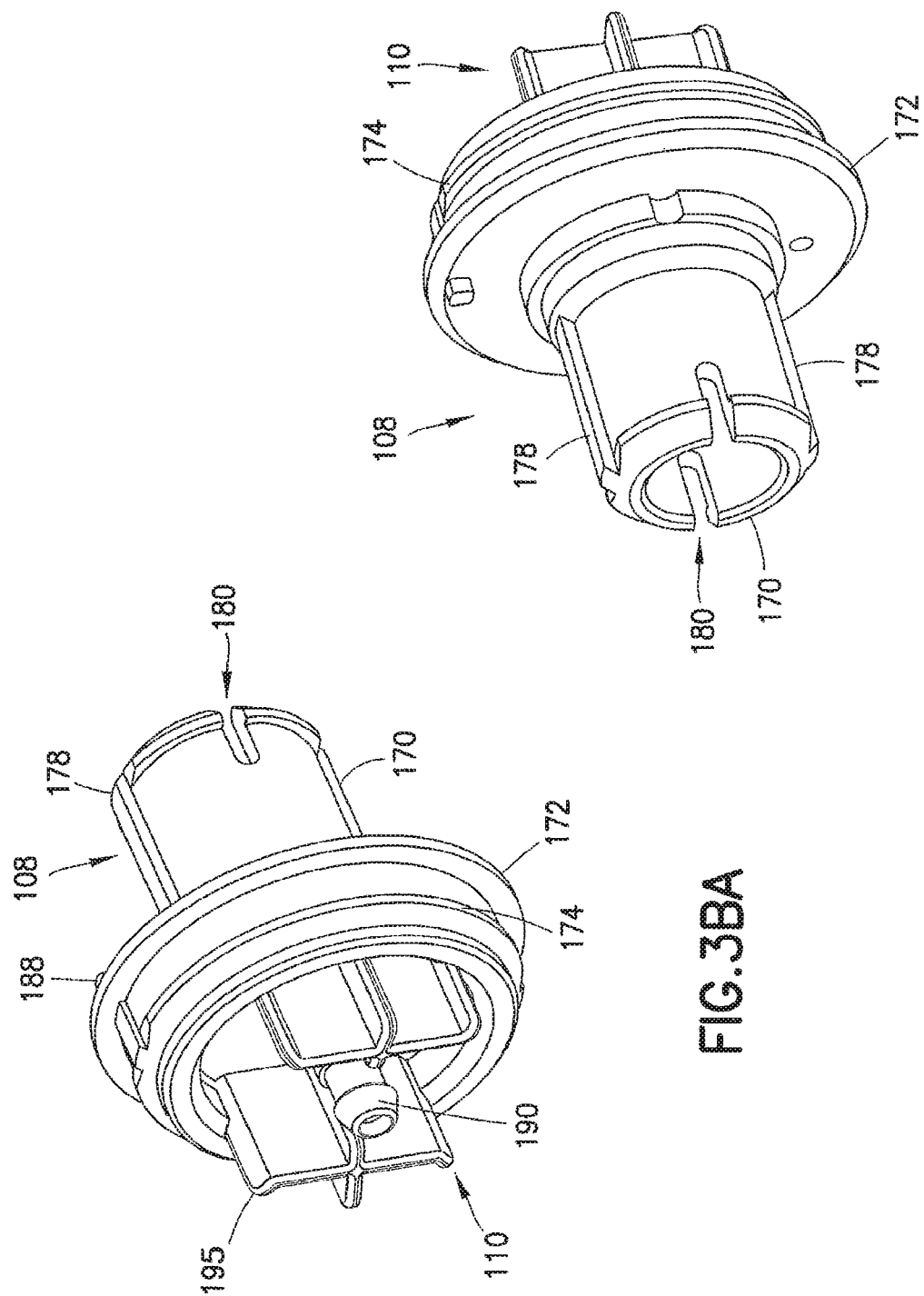

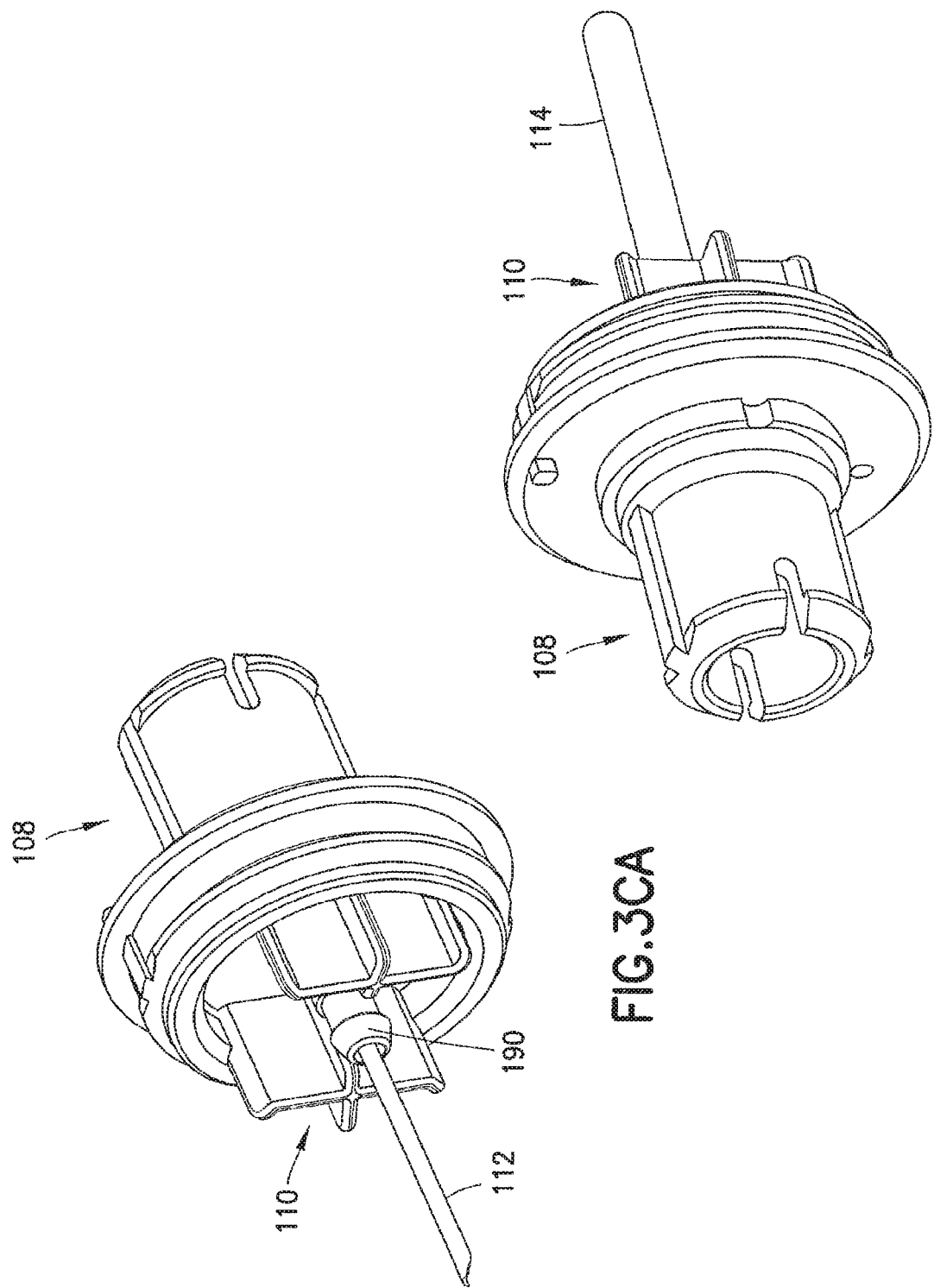

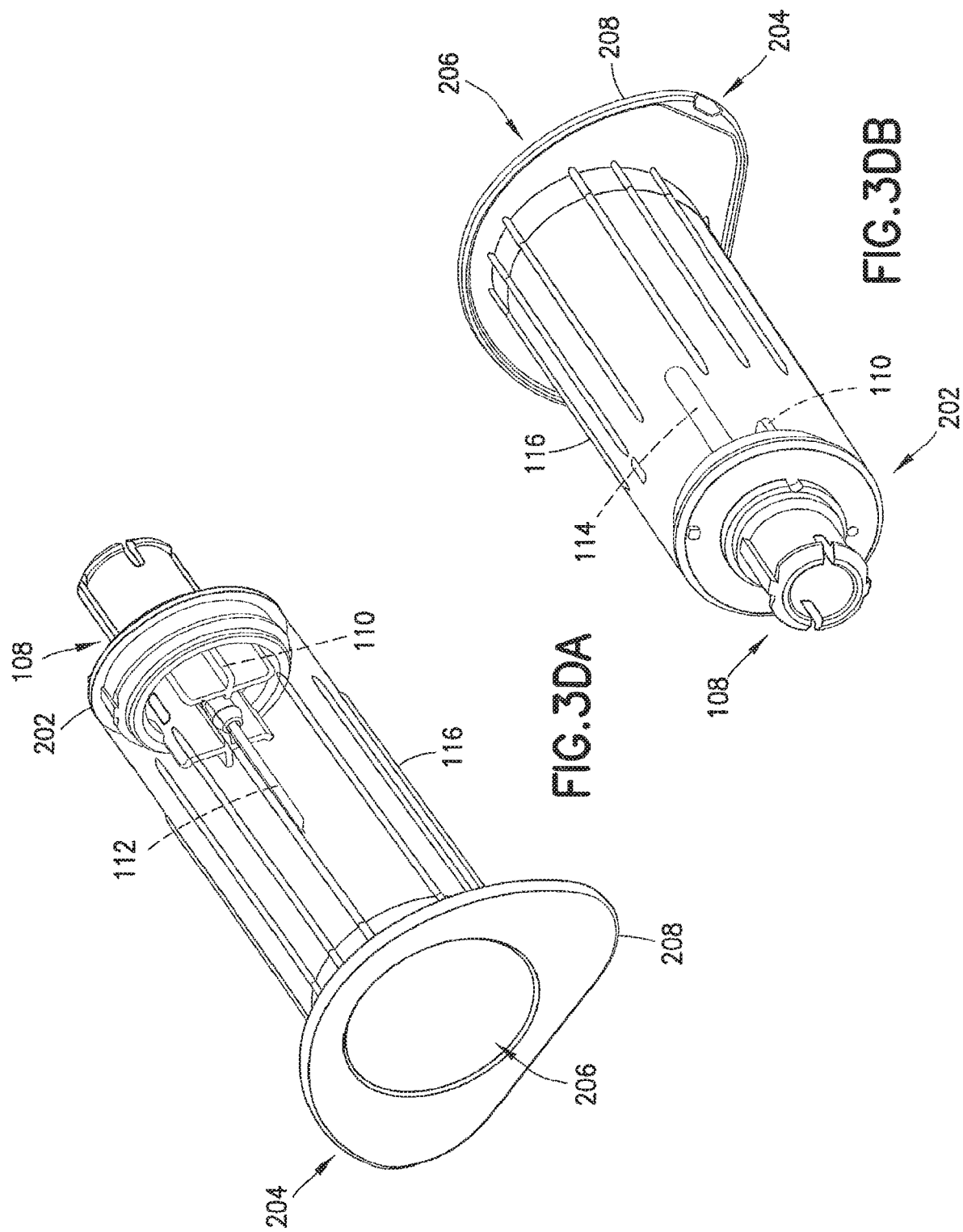

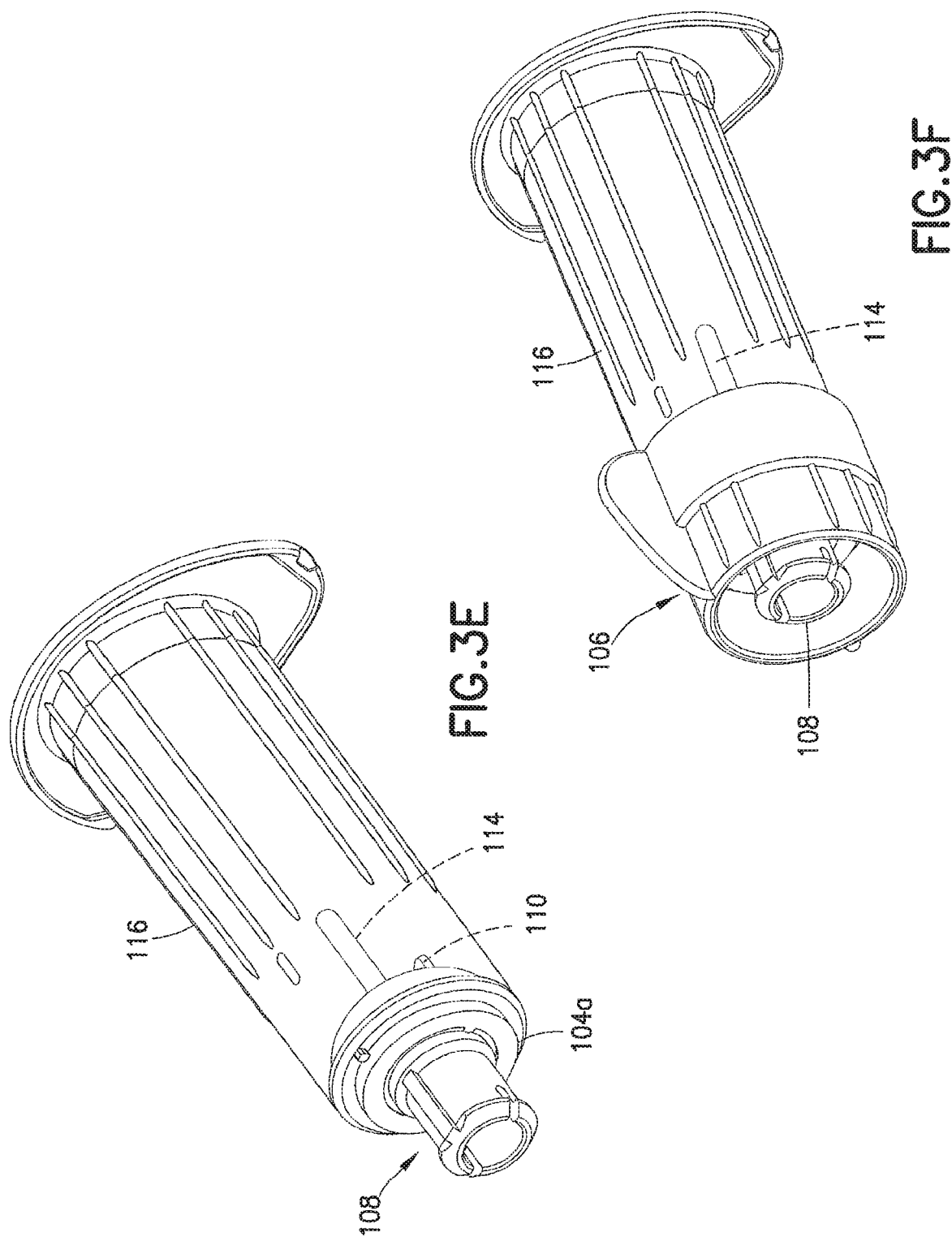

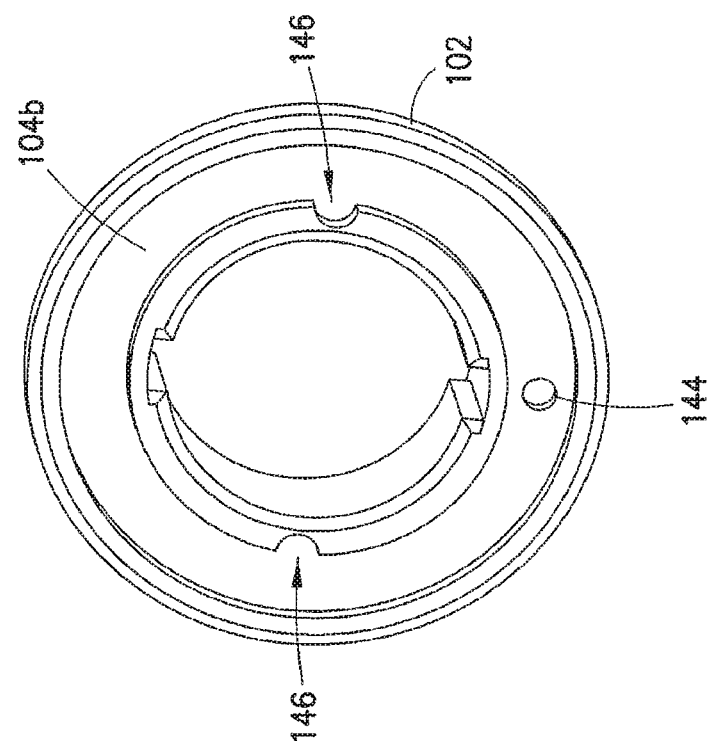
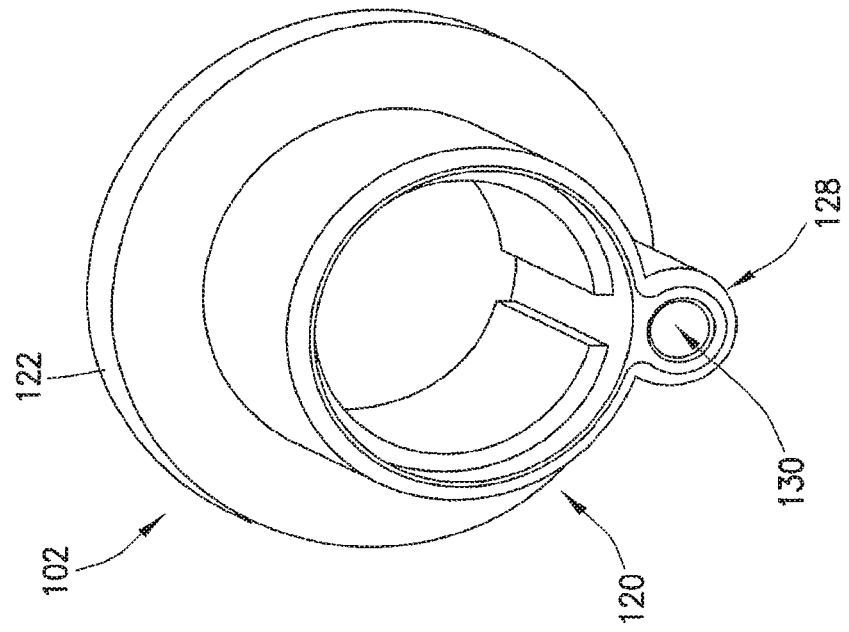

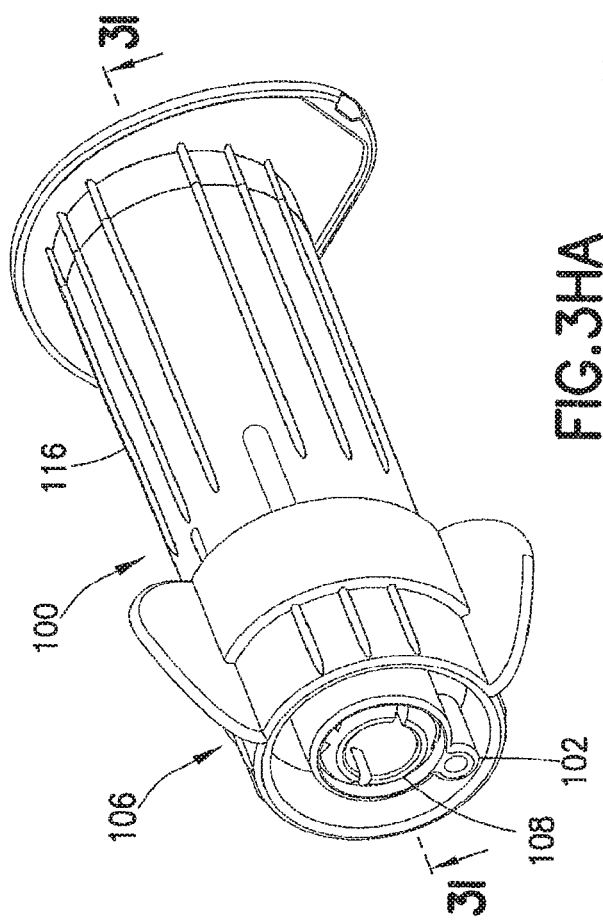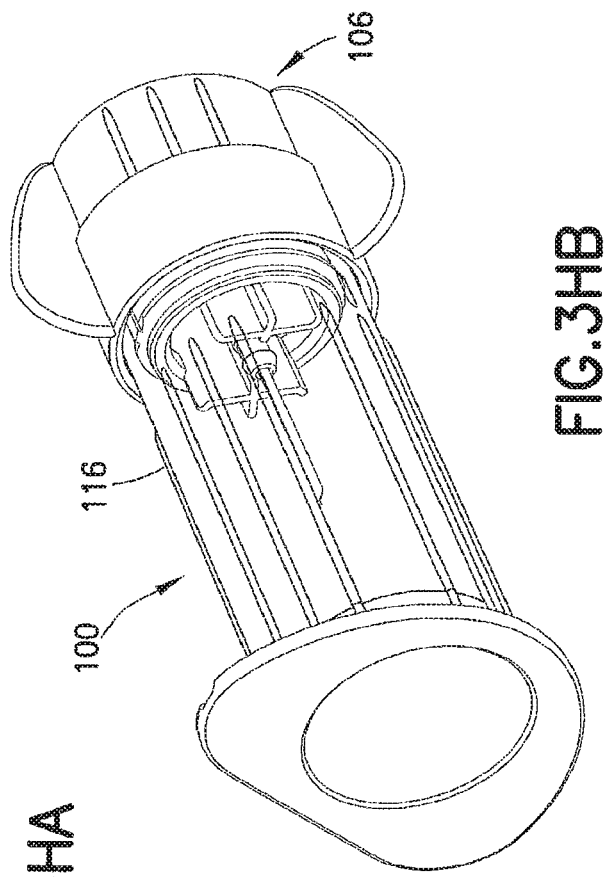

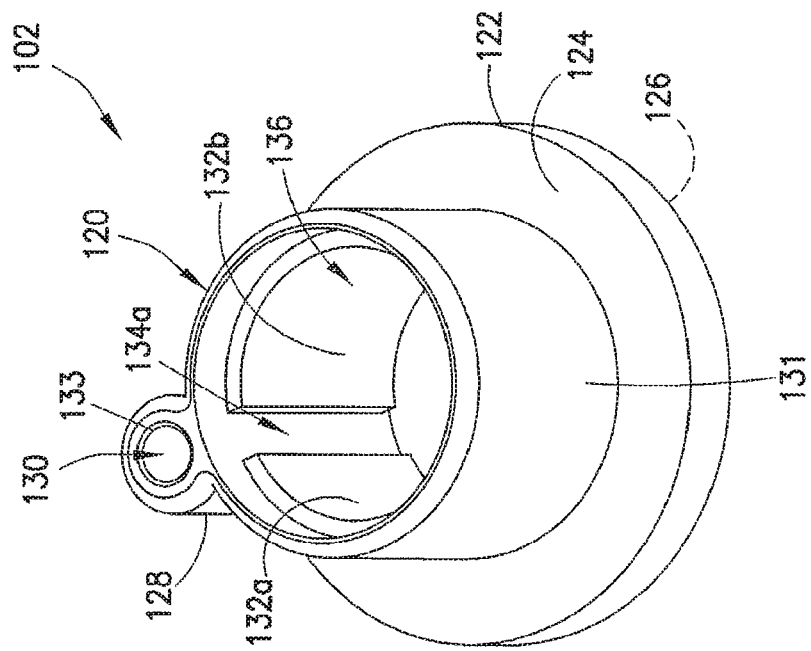
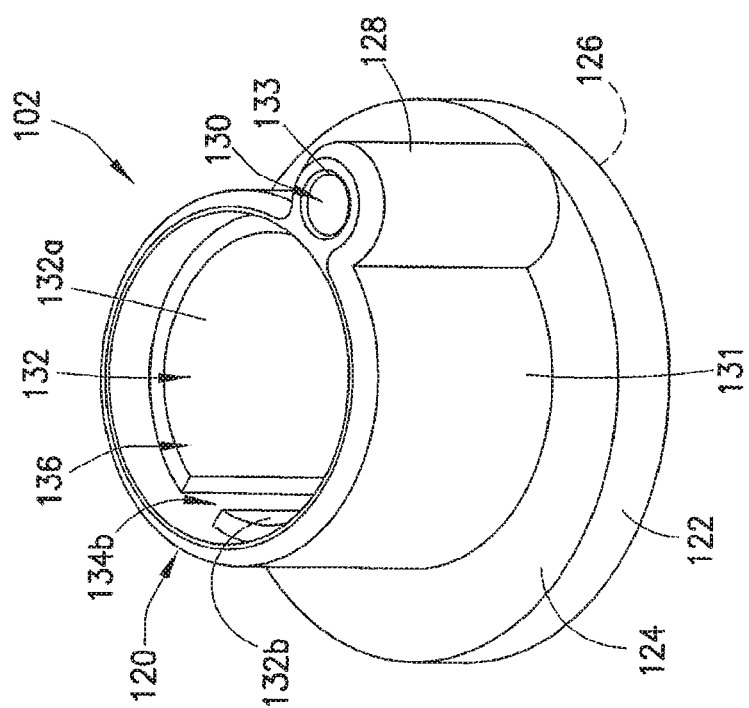
FIG.5B
FIG.5A

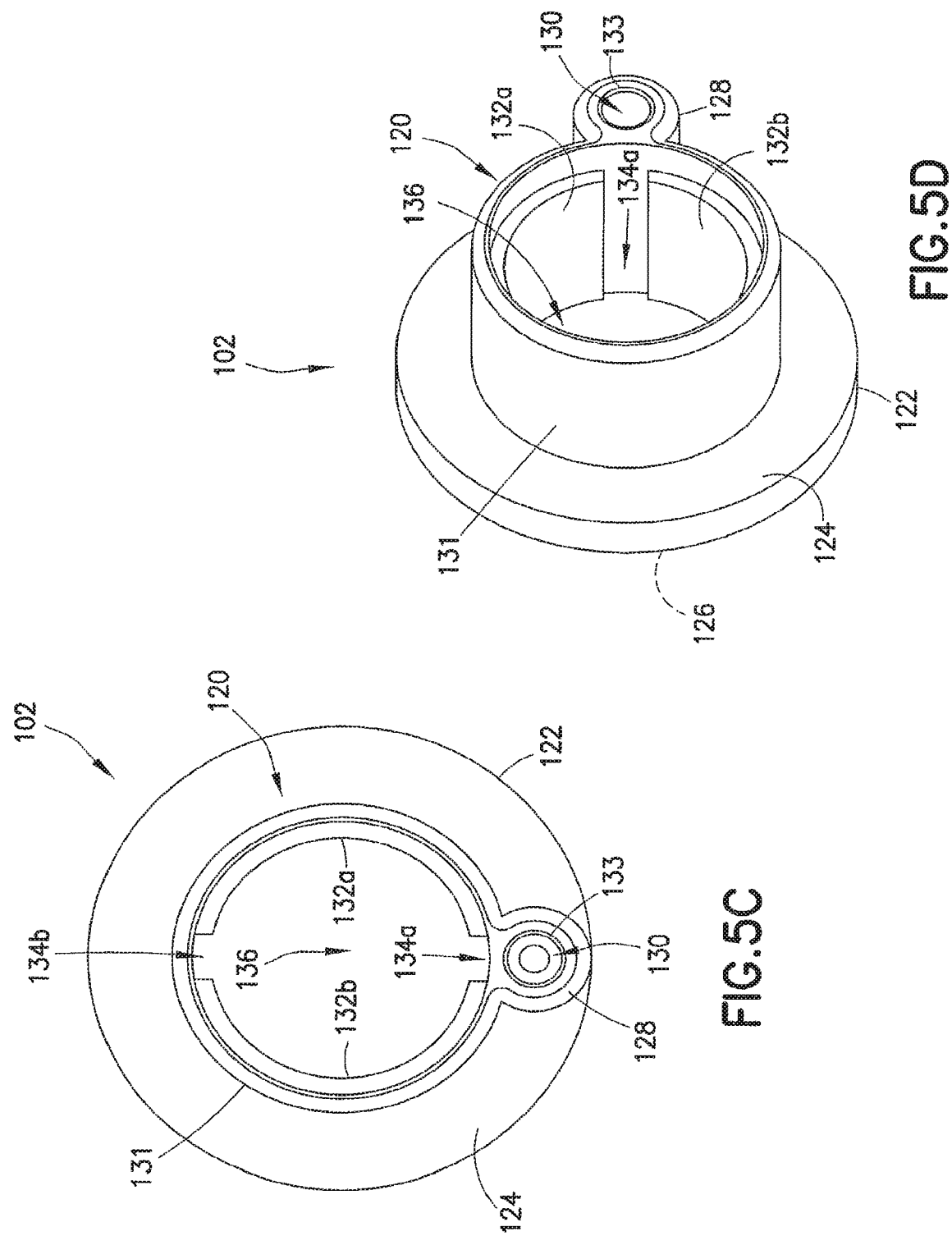

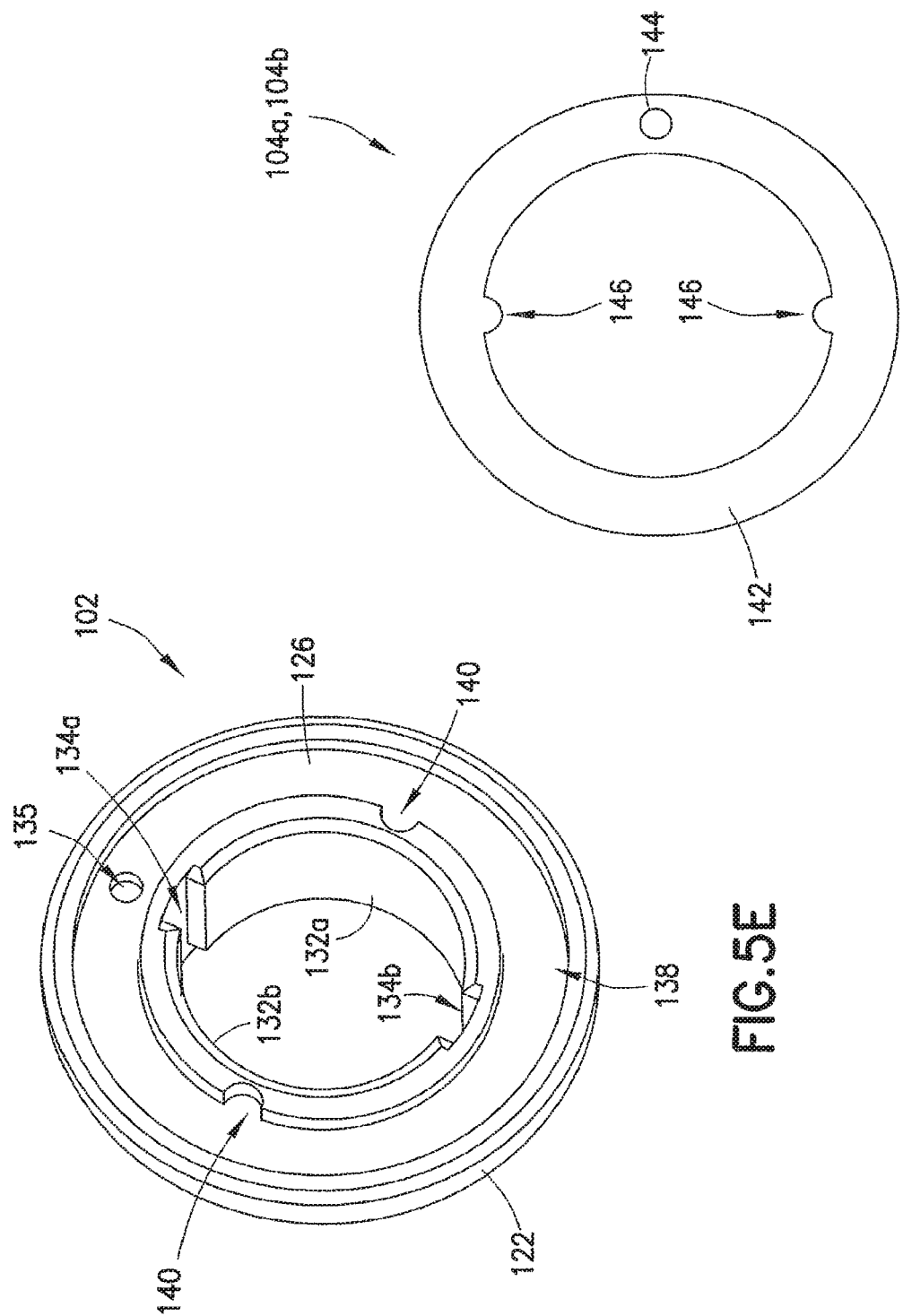

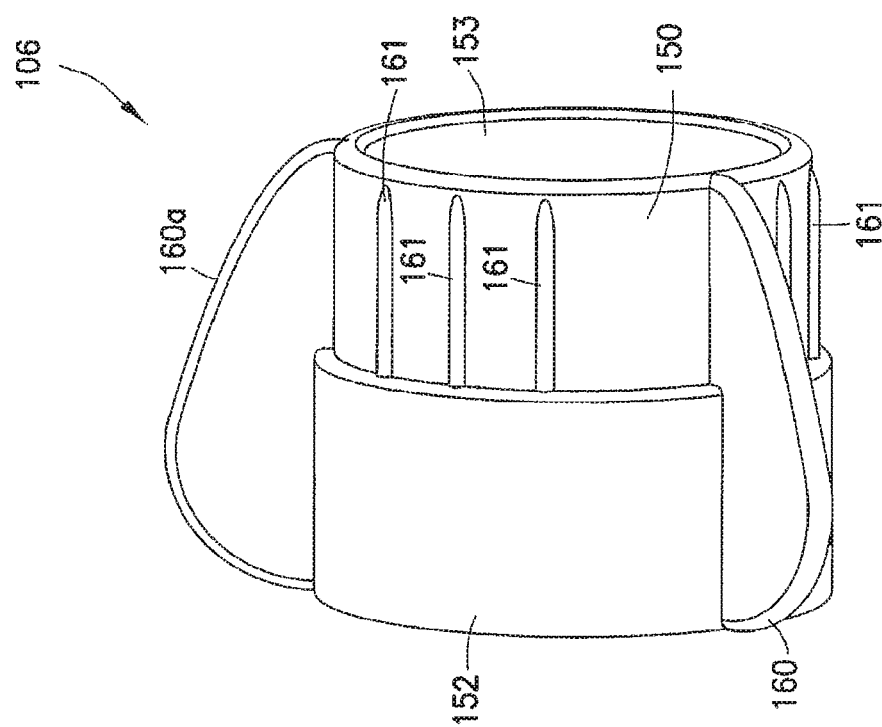
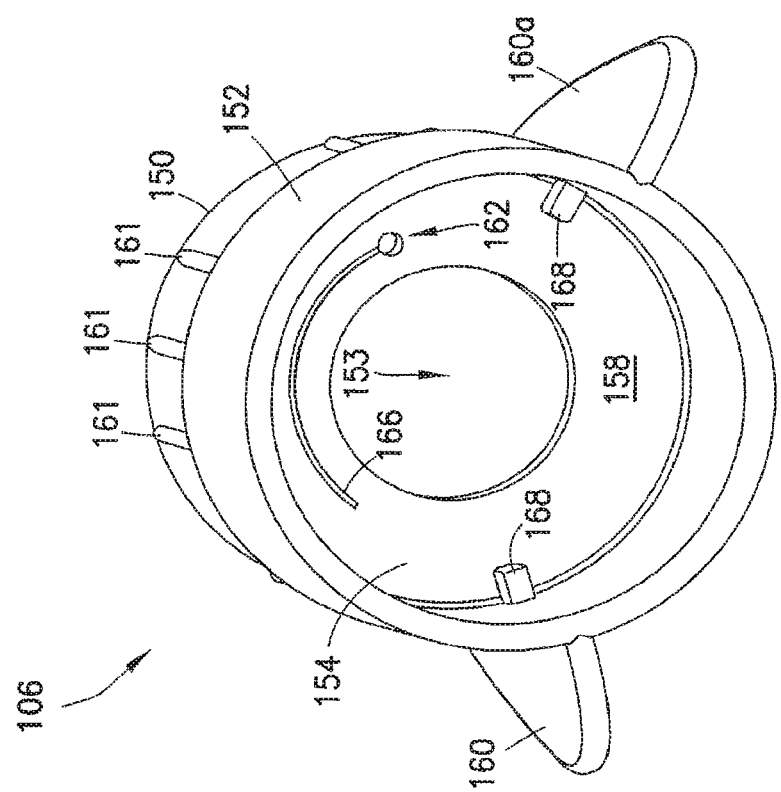
FIG. 7C
FIG. 7B

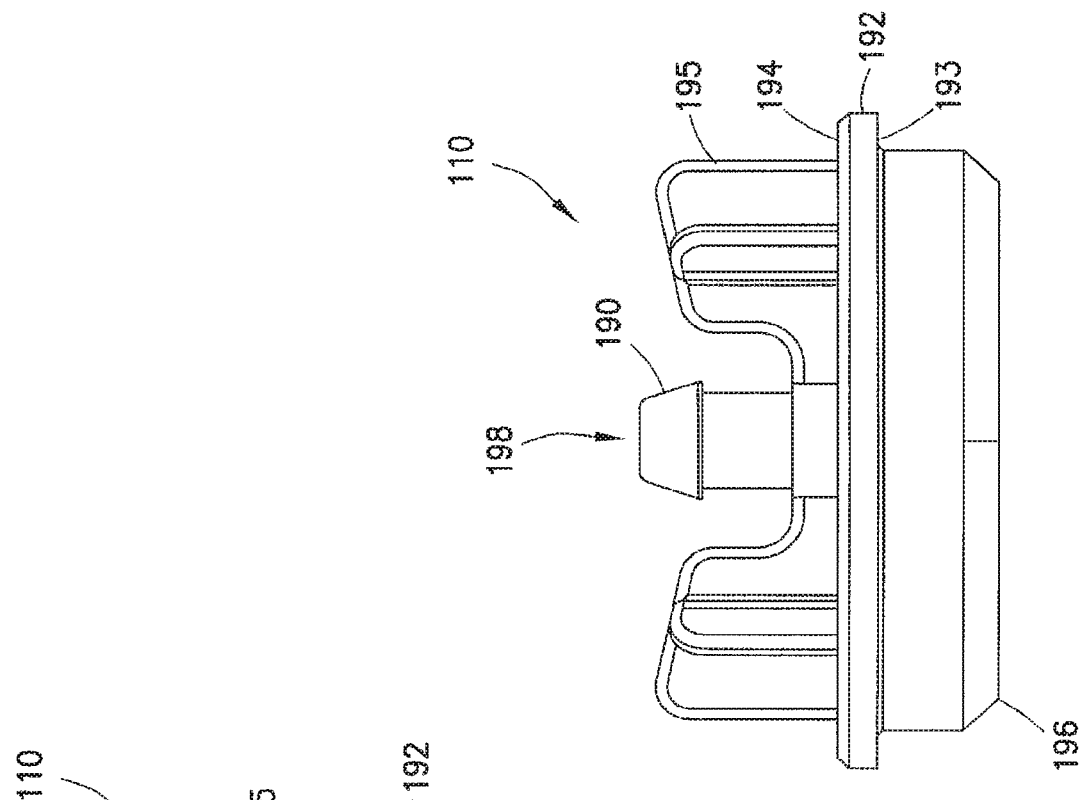
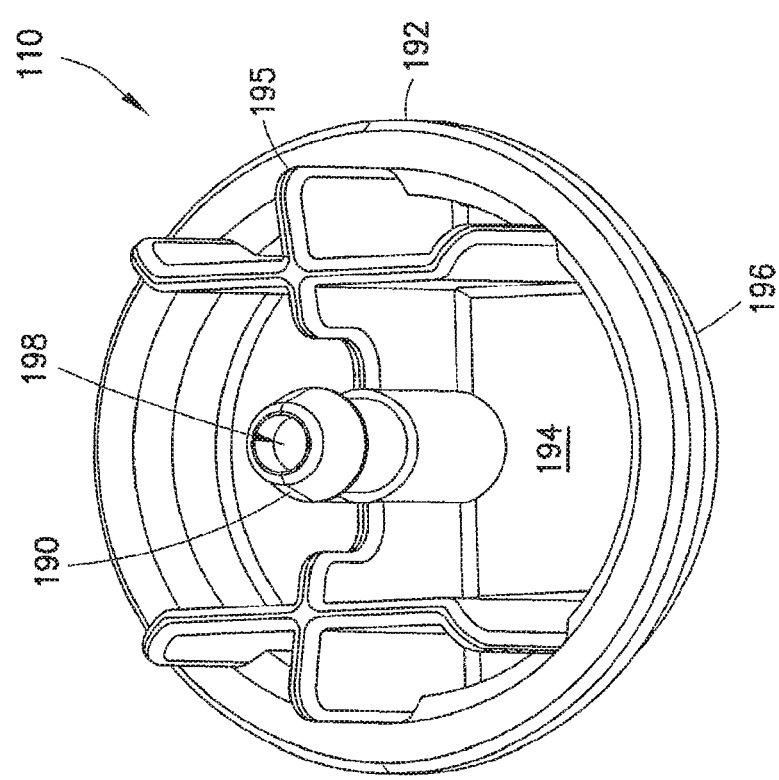

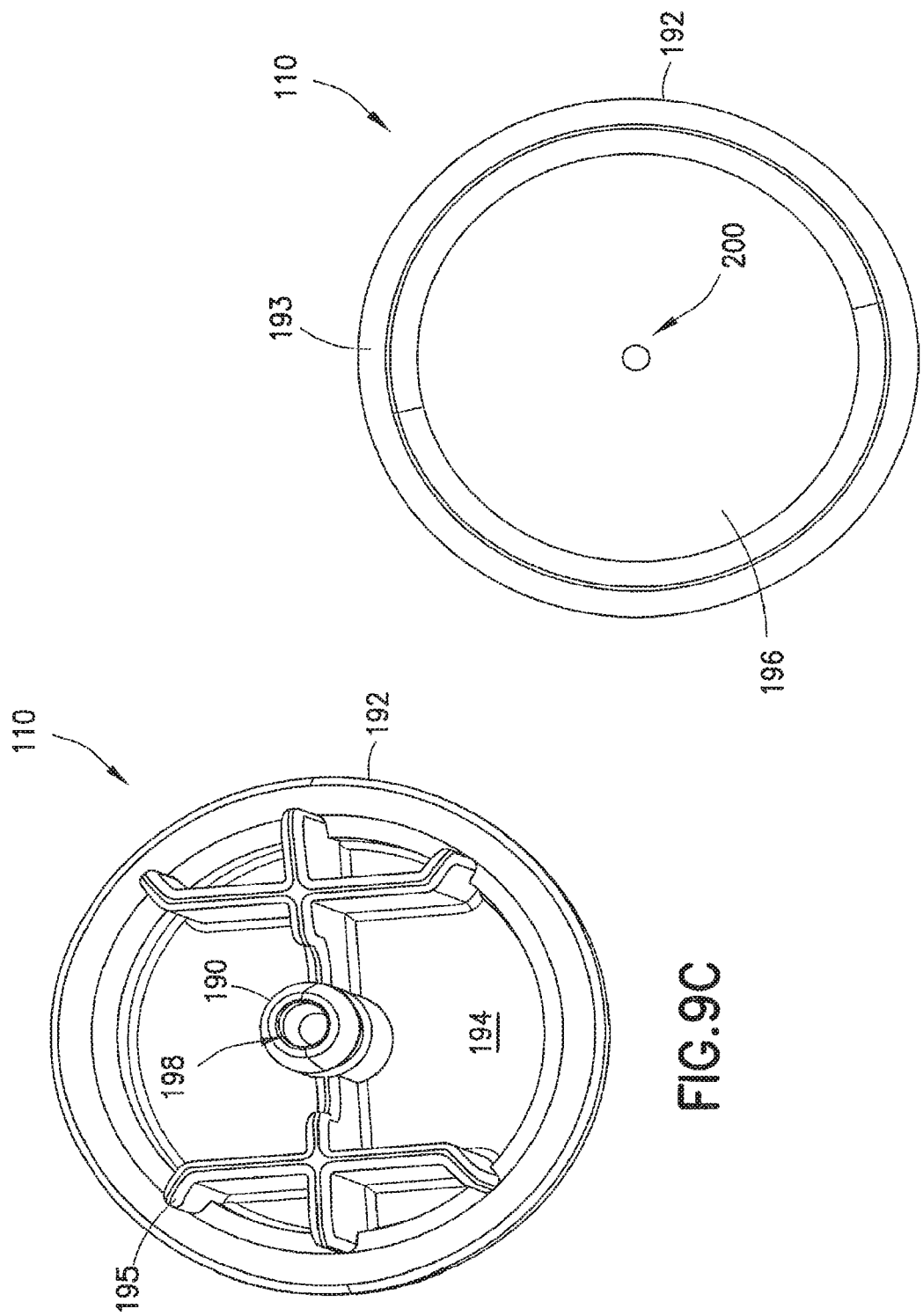

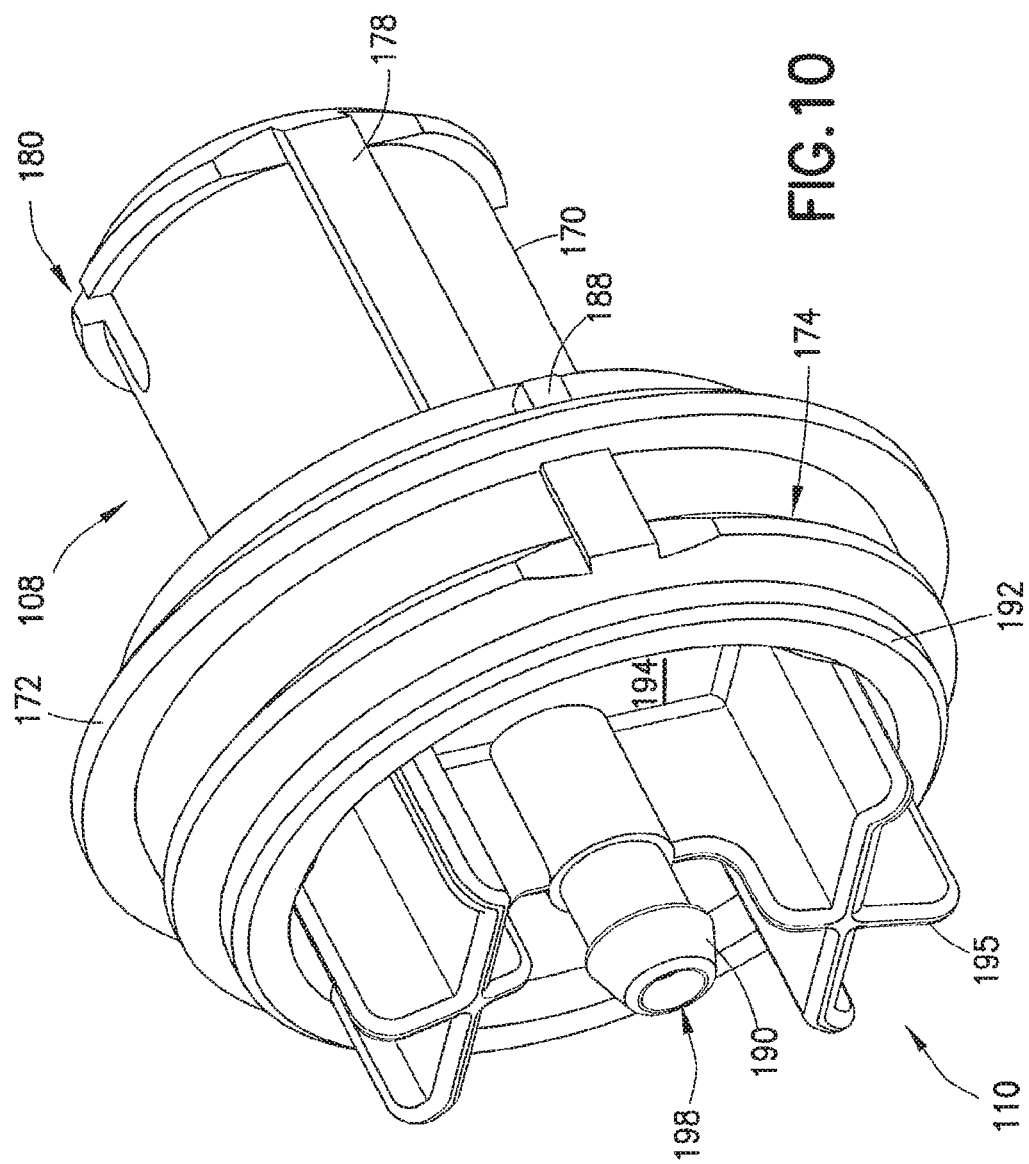

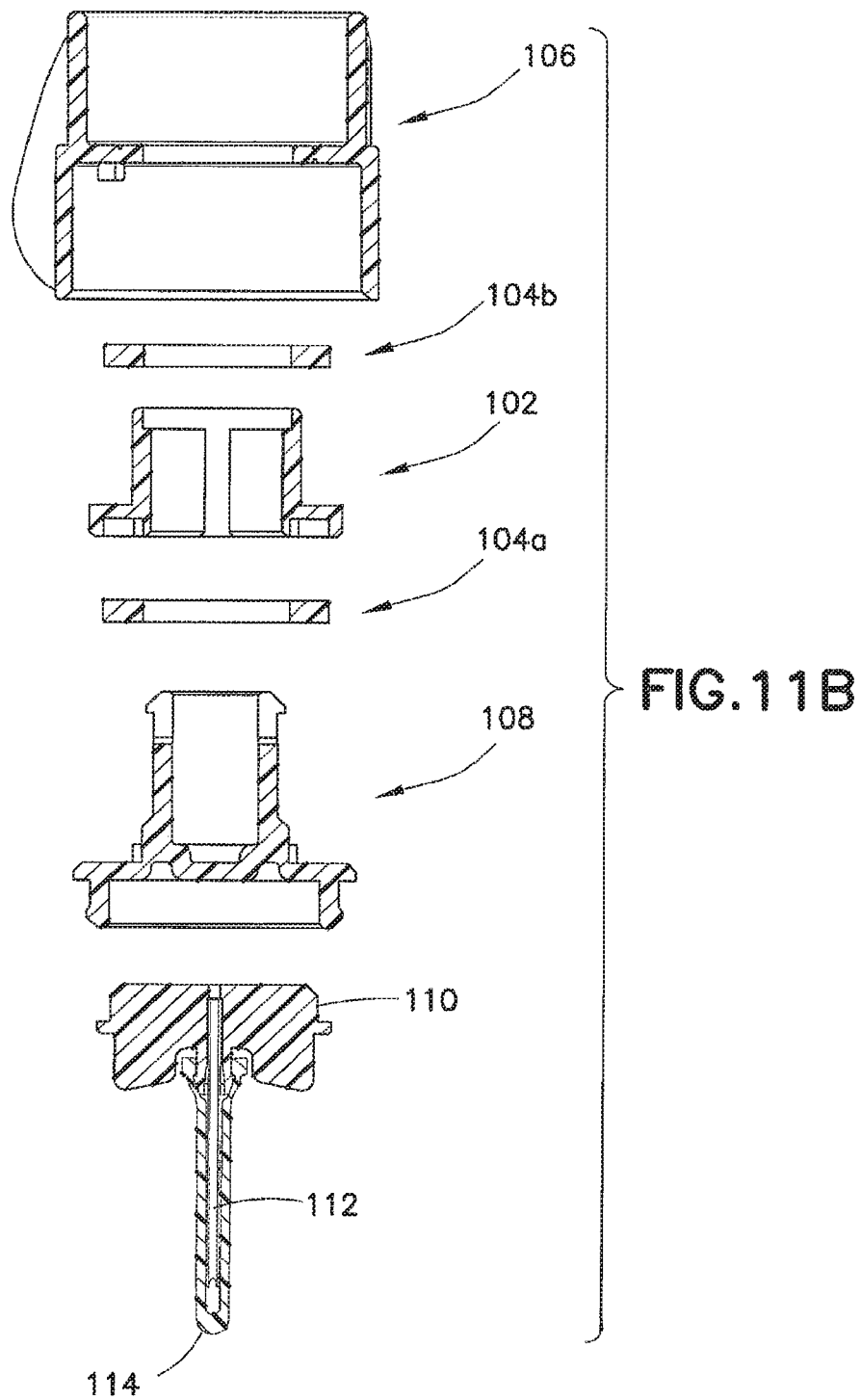

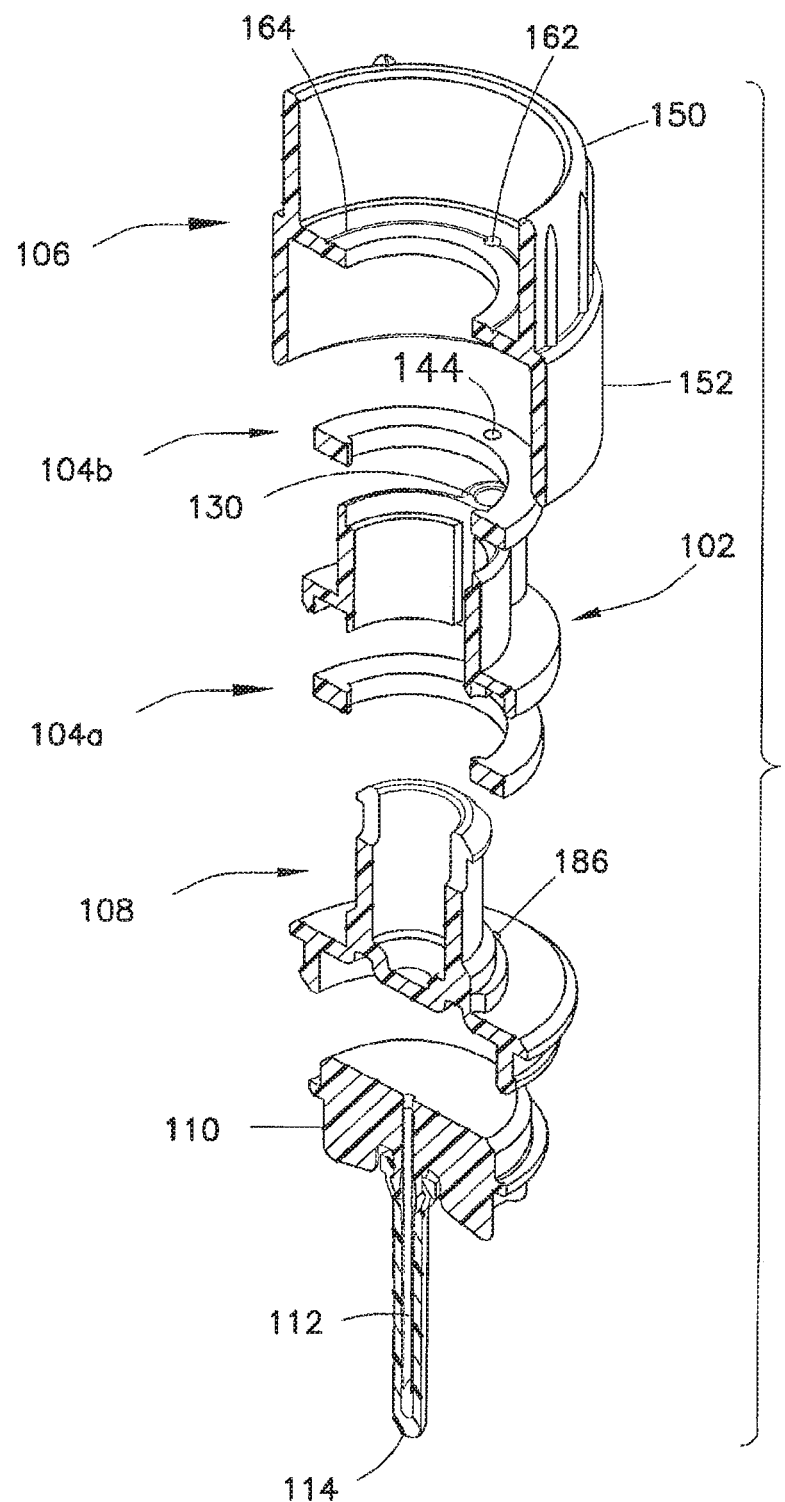

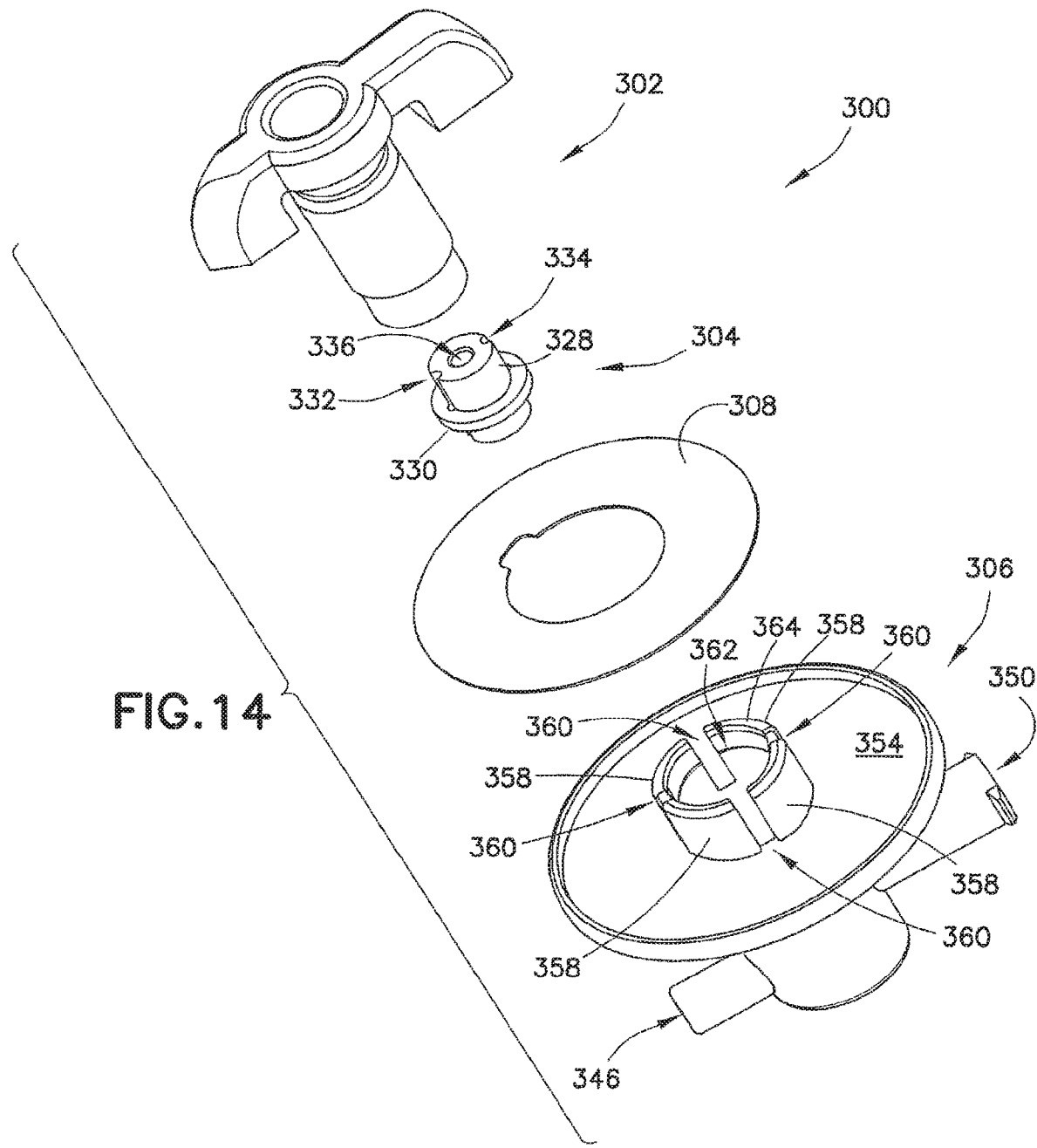

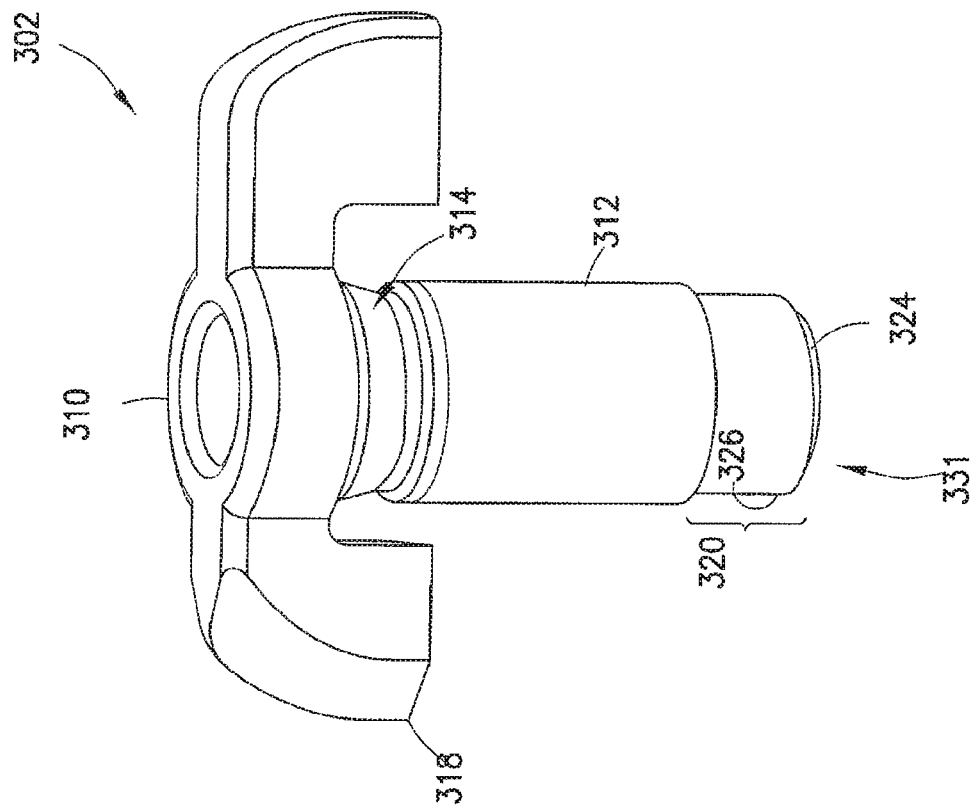
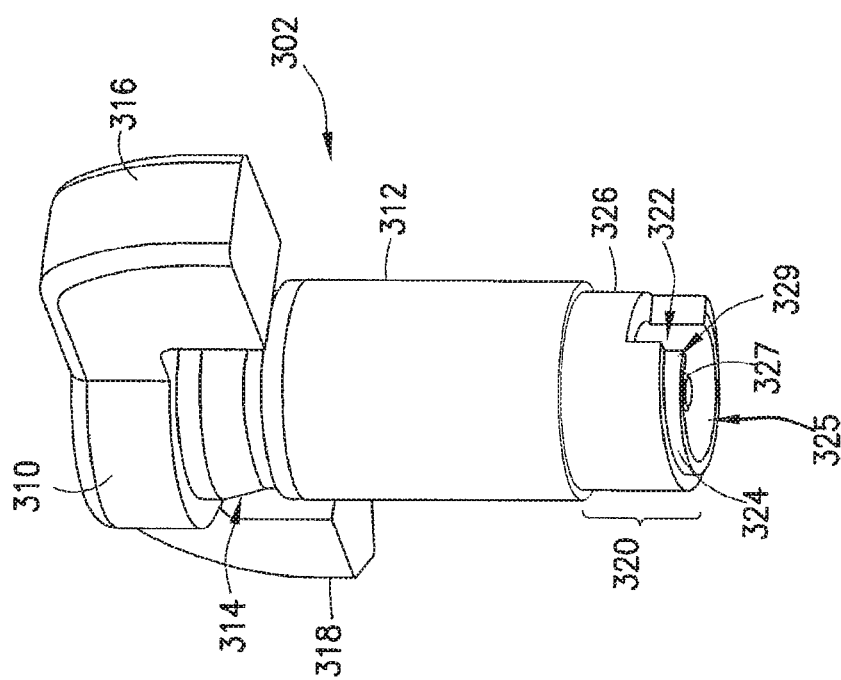
FIG. 15B
FIG. 15A

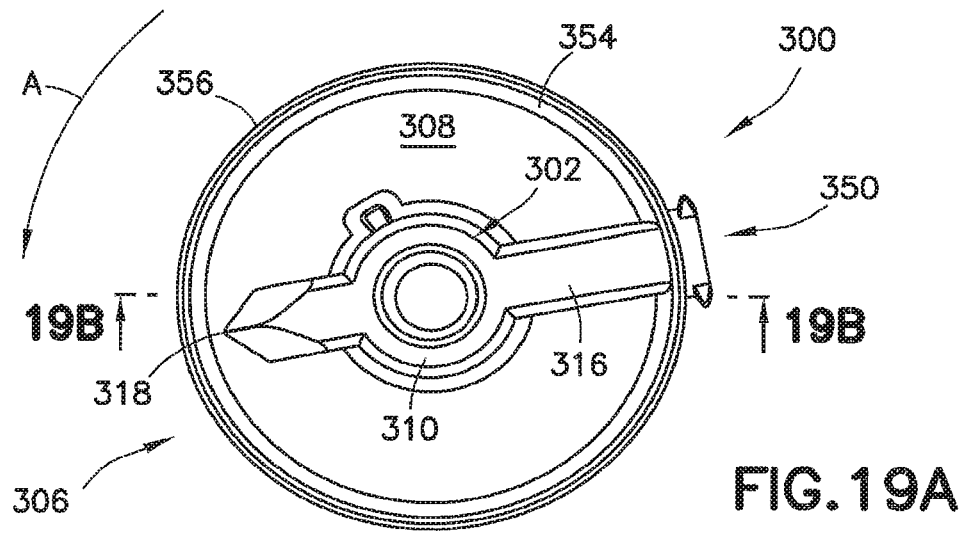
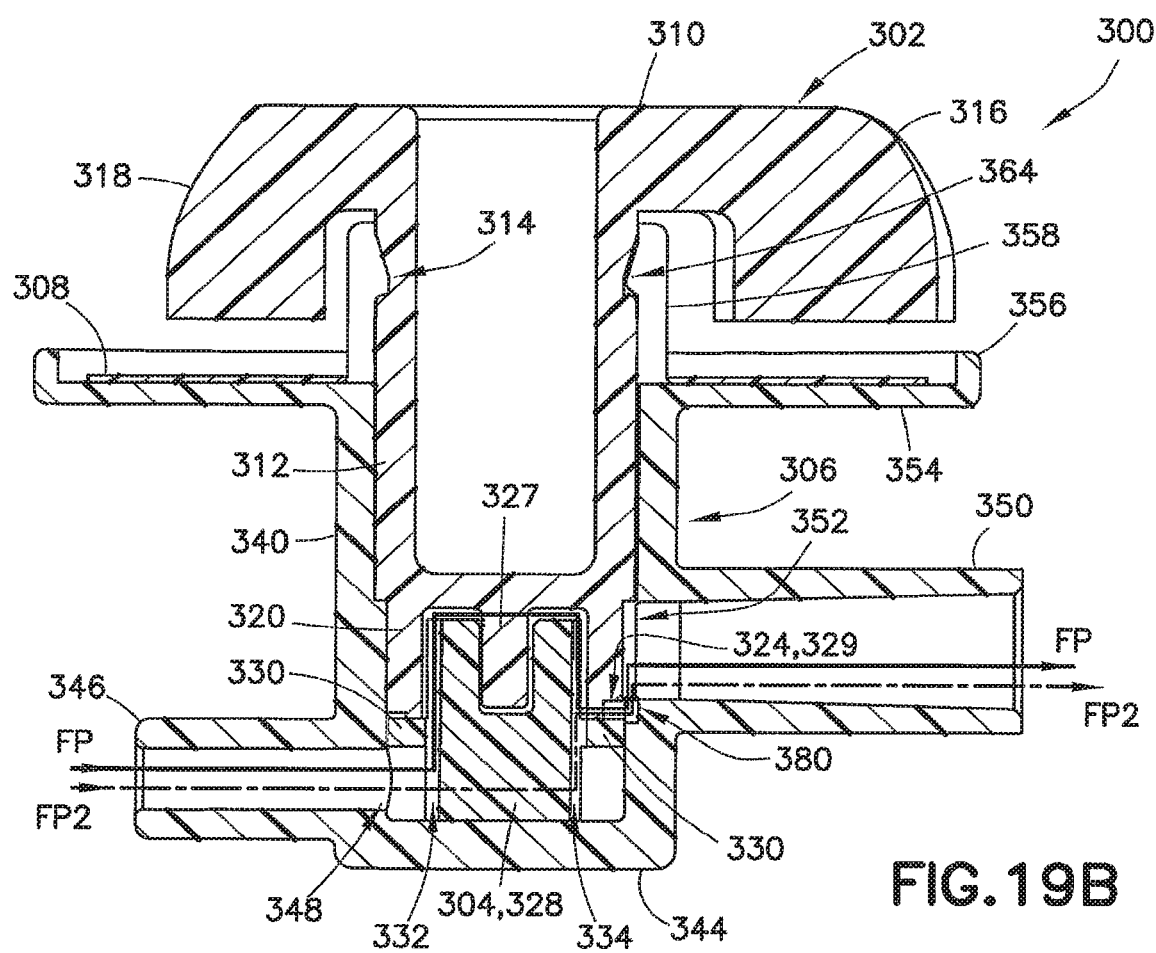
FIG.19A
FIG.19B

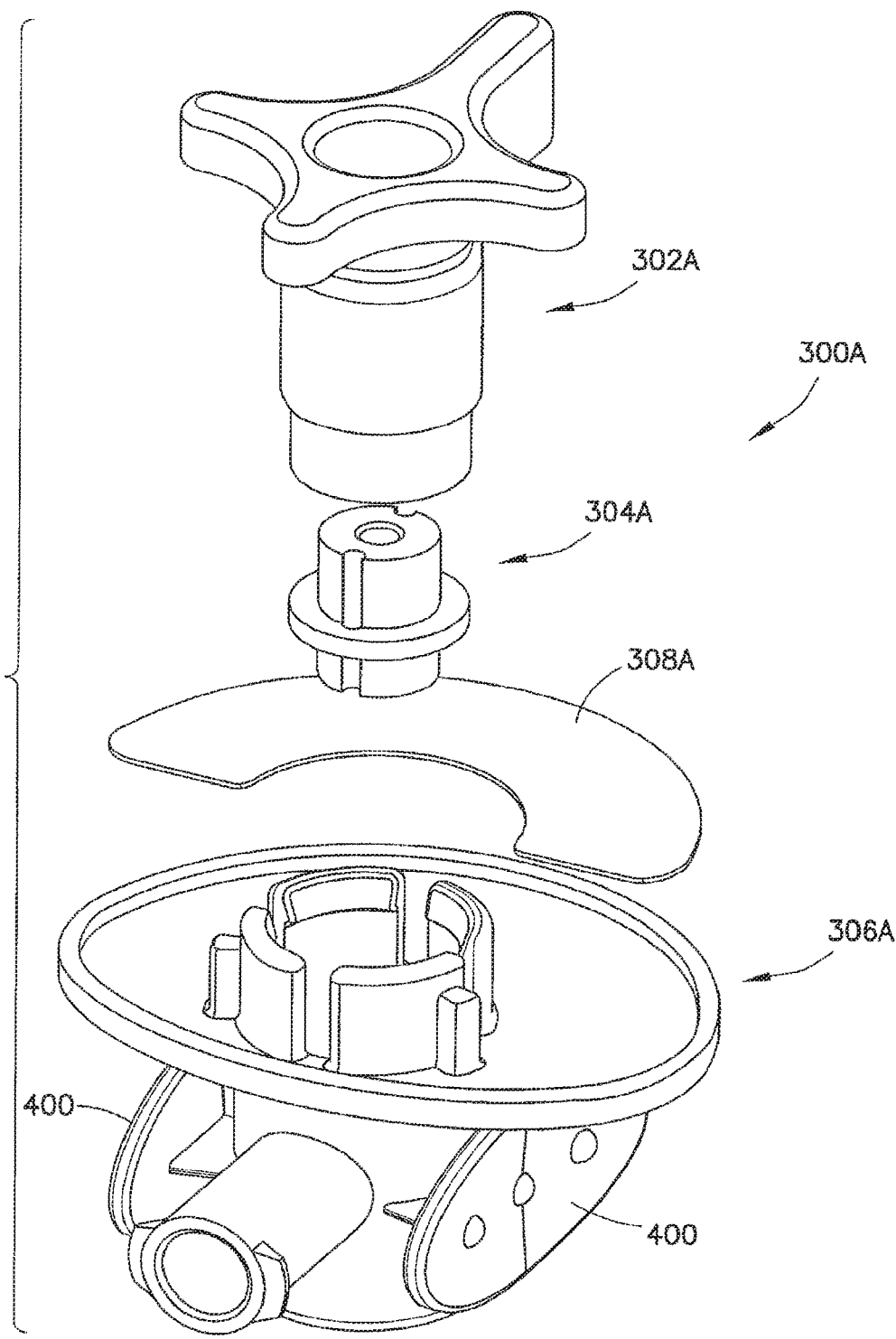

MANUAL FLOW REGULATION FOR BLOOD COLLECTION

CROSS-REFERENCE TO RELATED APPLICATION

The present application is a continuation of U.S. patent application Ser. No. 14/889,217 filed Nov. 5, 2015, which is the United States national phase of International Application No. PCT/US2013/041156 filed May 15, 2013, the disclosures of each of which are hereby incorporated in their entirety by reference.

BACKGROUND OF THE INVENTION

1. Field of the Disclosure

The present disclosure relates generally to a fluid flow regulator for regulating the initial flow rate of a fluid specimen. More particularly, the present disclosure relates to a variable fluid flow regulator that regulates the initial flow rate of blood into an evacuated blood collection device.

2. Description of the Related Art

Collapse of the patient's blood vessel during blood collection can occur as a result of a pressure differential created by the connection of the evacuated tube to the non-patient needle cannula. This collapse can occur as a result of the blood being removed too quickly from the patient's blood vessel. Physiological conditions such as the elasticity of the blood vessel wall can also contribute to this problem. With a standard evacuated tube, there is an instantaneous introduction of a sharp vacuum pressure when the evacuated tube is attached to the non-patient end of the blood collection device. This strong vacuum results in an initially high flow rate of blood out of the patient's blood vessel. This sharp outflow of blood coupled with the high elasticity of a patient's vessel can lead to the vessel wall being pulled down onto the bevel of the distal end of the patient cannula resulting in flow stoppage. The site for obtaining the blood supply can also be a contributing factor toward vessel collapse. Most typical blood collection sites are in the patient's arm and hand. Because of the one-way valves in the vessel, the supply of blood available for collection resides below the collection site. In-flow of new blood to this area is limited as a result of the capillary blood vessels. In the situations where there is little resident blood, such as a hand collection, the sharp vacuum from the collection tube leads to a high flow rate out of the vessel, which can lead to an outflow rate higher than the inflow rate and a rapid depletion of the resident blood. This scenario can quickly lead to collapse.

One way to avoid this collapse is to use a syringe for blood collection. Syringes can provide a user with greater control over the flow rate of blood out of the patient. The initial spike in pressure from an evacuated tube and the associated high flow rate can be avoided through the use of a syringe collection technique. However, the skill of the user plays a large role with this type of collection as there can be a lot of variability in the amount of force the user exerts on the syringe plunger and the associated flow rates. Also, if not used appropriately, the flow rates can be greater than a standard evacuated tube.

The manual flow regulator of the present invention seeks to minimize the incidence of vessel or vein collapse in patient populations susceptible to this type of condition. The device achieves this by controlling the flow rate of the blood out of the patient's vessel or vein. This is accomplished through the use of a variable flow resistor. The resistor acts to slow down the initial flow rate of blood into the evacuated tube and avoid the initial spike, as well as to slow down the overall collection time to avoid depleting the resident blood in the vessel too rapidly.

SUMMARY OF THE INVENTION

The present disclosure provides a specimen collection assembly including a flow control member for adjustably altering a flow path. In one configuration, the flow control member defines a regulation channel in fluid communication with the lumen of a cannula, wherein the flow control member is configured to adjustably alter an effective flow distance between the lumen of the cannula and the interior of an evacuated collection container. In another configuration, the flow control member is positioned to vary an effective cross-sectional area of at least one of an inlet port and an outlet port adapted to be in fluid communication with the lumen and the evacuated collection container.

In accordance with an embodiment of the present invention, a specimen collection assembly includes a cannula, defining a lumen therein. The specimen collection assembly further includes a flow control member defining a regulation channel in fluid communication with the lumen of the cannula, wherein the flow control member is configured to adjustably alter an effective flow distance between the lumen of the cannula and an interior of an evacuated collection container.

In one configuration, the specimen collection assembly further includes a hub at least partially supporting the cannula and defining a collection channel therein, the collection channel adapted for fluid communication with the interior of the evacuated collection container. In another configuration, the flow control member is manually adjustable to alter the effective flow distance. In yet another configuration, the flow control member is rotatable between a maximum flow position, in which the regulation channel has a first effective length, and a minimum flow position, in which the regulation channel has a second effective length, the second effective length being longer than the first effective length. In one configuration, the flow control member includes a hub engaging member engaged with the hub, the hub engaging member defining a through-port extending therethrough, the through-port connecting a portion of the regulation channel defined within a proximal surface of the flow control member to a portion of the regulation channel defined within a distal surface of the flow control member. In one configuration, the specimen collection assembly further includes a spine member engaged with a portion of the hub and a portion of the hub engaging member, wherein the spine member and the hub define a flow space therebetween in fluid communication with the regulation channel and the collection channel. In another configuration, the flow control member and the spine member include opposing detents to limit rotation of the flow control member between a minimum flow position and a maximum flow position. In yet another configuration, the specimen collection assembly further includes a specimen collection container in fluid communication with the lumen of the cannula. In another configuration, the specimen collection assembly further includes a hub engaging member engaged with a portion of the hub and defining a flow-entry port extending therethrough and in fluid communication with the regulation channel. In yet another configuration, the specimen collection assembly further includes a spine member engaged with and positioned between the hub and the hub engaging member, wherein the spine member and hub define a flow space therebetween in fluid communication with the regulation channel and the collection channel, the spine member defining a through-port extending therethrough connecting the flow space and the regulation channel in fluid communication. In one configuration, the spine member through-port and the flow-entry port are axially aligned. In another configuration, the specimen collection assembly further includes at least one gasket defining a gasket through-port aligned with at least one of the through-port and the flow-entry port. In yet another configuration, the flow control member is rotatable about a portion of the hub. In one configuration, the regulation channel is defined radially about a center axis of a hub engaging member engaged with the hub. In another configuration, the specimen collection assembly further includes a holder housing having a distal end and a proximal end defining an internal chamber therebetween, the proximal end being adapted to receive a portion of the evacuated collection container therein, wherein the evacuated collection container is adapted to be pierced by the cannula to establish flow between an internal chamber of the evacuated collection container and the regulation channel. In yet another configuration, the flow control member includes at least one manipulation wing for transition by a user between a minimum flow position and a maximum flow position.

In accordance with another embodiment of the present invention, a specimen collection assembly includes a cannula defining a lumen therein. The specimen collection assembly further includes a housing having a housing wall defining an internal chamber having an inlet port and an outlet port, the inlet port adapted for fluid communication with the lumen, the outlet port adapted for fluid communication with an evacuated collection container, and a flow control member positioned to vary an effective cross-sectional area of at least one of the inlet port and the outlet port.

In one configuration, the flow control member is manually adjustable to alter the effective cross-sectional area. In another configuration, the flow control member is rotatable between a maximum flow position and a minimum flow position. In yet another configuration, the flow control member includes a helical profile disposed about a central axis of the flow control member, wherein, upon rotation of the flow control member, the helical profile is configured to open and/or close at least one of the inlet port and/or the outlet port. In one configuration, the specimen collection assembly further includes a flow control insert disposed at least partially within the internal chamber and configured to cooperate with the flow control member to direct flow from the inlet port to the outlet port.

In accordance with another embodiment of the present invention, a specimen collection assembly includes a cannula, defining a lumen therein. The specimen collection assembly further includes a hub at least partially supporting the cannula and defining a collection channel therein, the collection channel adapted for fluid communication with an interior of an evacuated collection container, and flow control means for altering a flow path between the lumen of the cannula and the interior of the evacuated collection container.

In one configuration, the flow control means includes manually varying a length of the flow path. In another configuration, the flow control means includes manually varying a cross-sectional area of the flow path.

In accordance with another embodiment of the present invention, a method of regulating blood flow in a blood collection assembly includes: establishing fluid communication between a patient vasculature and an evacuated collection container; and regulating blood flow from the patient vasculature by varying an effective flow distance between a patient cannula and the evacuated collection container by manually adjusting a flow control member defining a flow regulation channel in the blood collection assembly to vary an effective length of the regulation channel.

In accordance with another embodiment of the present invention, a method of regulating blood flow in a blood collection assembly includes: establishing fluid communication between a patient vasculature and an evacuated collection container; and regulating blood flow from the patient vasculature by varying an effective cross-sectional area of at least one of an inlet port and an outlet port defined in a portion of a blood collection assembly housing provided in fluid communication with the patient vasculature.

In one configuration, the regulating blood flow occurs by manually varying the effective cross-sectional area of the at least one of an inlet port and an outlet port.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 2 is an exploded, perspective view of a flow regulator system in accordance with an embodiment of the present invention.

FIG. 3A is an assembled, perspective view of the flow regulator system of FIG. 2 in accordance with an embodiment of the present invention.

FIG. 3BA is an assembled, perspective view of a spine and a hub of the flow regulator system of FIG. 2 in accordance with an embodiment of the present invention.

FIG. 3BB is another assembled, perspective view of the spine and the hub of FIG. 3BA.

FIG. 3CA is an assembled, perspective view of the spine and the hub of FIG. 3BA with a needle of the flow regulator system of FIG. 2 secured to the hub of FIG. 3BA in accordance with an embodiment of the present invention.

FIG. 3CB is another assembled, perspective view of FIG. 3CA with a sleeve of the flow regulator system of FIG. 2 disposed over the needle of the flow regulator system in accordance with an embodiment of the present invention.

FIG. 3DA is an assembled, perspective view of the spine and the hub of FIG. 3CB with the spine and the hub of FIG. 3CB secured to a tube holder of the flow regulator system of FIG. 2 in accordance with an embodiment of the present invention.

FIG. 3DB is another assembled, perspective view of the spine, the hub, and the tube holder of FIG. 3DA.

FIG. 3E is an assembled, perspective view of the spine, the hub, and the tube holder of FIG. 3DA with a gasket of the flow regulator system of FIG. 2 secured to the spine of FIG. 3DA in accordance with an embodiment of the present invention.

FIG. 3F is an assembled, perspective view of the flow regulator system of FIG. 3E with a dial of the flow regulator system of FIG. 2 assembled to the tube holder of FIG. 3E in accordance with an embodiment of the present invention.

FIG. 3GA is a perspective view of a tube holder sub-assembly of the flow regulator system of FIG. 2 in accordance with an embodiment of the present invention.

FIG. 3GB is an assembled, perspective view of the tube holder sub-assembly of FIG. 3GA and a gasket of the flow regulator system of FIG. 2 in accordance with an embodiment of the present invention.

FIG. 3HA is an assembled, perspective view of the flow regulator system of FIG. 3F with the tube holder sub-assembly and the gasket of FIG. 3GB secured to the spine of FIG. 3F in accordance with an embodiment of the present invention.

FIG. 3HB is another assembled, perspective view of the flow regulator system of FIG. 3HA in accordance with an embodiment of the present invention.

FIG. 5A is a perspective view of a tube holder of the flow regulator system of FIG. 2 in accordance with an embodiment of the present invention.

FIG. 5B is another perspective view of the tube holder of FIG. 5A in accordance with an embodiment of the present invention.

FIG. 5C is a plan view of the tube holder of FIG. 5A in accordance with an embodiment of the present invention.

FIG. 5D is another perspective view of the tube holder of FIG. 5A in accordance with an embodiment of the present invention.

FIG. 5E is a bottom perspective view of the tube holder of FIG. 5A in accordance with an embodiment of the present invention.

FIG. 6 is a plan view of a gasket of the flow regulator system of FIG. 2 in accordance with an embodiment of the present invention.

FIG. 7B is a bottom perspective view of the dial of FIG. 7A in accordance with an embodiment of the present invention.

FIG. 7C is a side perspective view of the dial of FIG. 7A in accordance with an embodiment of the present invention.

FIG. 9A is a perspective view of a hub of the flow regulator system of FIG. 2 in accordance with an embodiment of the present invention.

FIG. 9B is a side elevation view of the hub of FIG. 9A in accordance with an embodiment of the present invention.

FIG. 9C is a plan view of the hub of FIG. 9A in accordance with an embodiment of the present invention.

FIG. 9D is a bottom view of the hub of FIG. 9A in accordance with an embodiment of the present invention.

FIG. 10 is an assembled perspective view of the spine of FIG. 8A and the hub of FIG. 9A in accordance with an embodiment of the present invention.

FIG. 11B is an exploded, cross-sectional view taken along line 11B-11B of FIG. 11A in accordance with an embodiment of the present invention.

FIG. 11F is an exploded, cross-sectional view taken along line 11F-11F of FIG. 11E in accordance with an embodiment of the present invention.

FIG. 14 is an exploded, perspective view of a flow regulator system in accordance with another exemplary embodiment of the present invention in accordance with an embodiment of the present invention.

FIG. 15A is a perspective view of a flow control dial of the flow regulator system of FIG. 14 in accordance with an embodiment of the present invention.

FIG. 15B is another perspective view of the flow control dial of FIG. 15A in accordance with an embodiment of the present invention.

FIG. 19A is a plan view of the flow regulator system of FIG. 16 in a second flow or second partially open position in accordance with an embodiment of the present invention.

FIG. 19B is a cross-sectional view taken along line 19B-19B of FIG. 19A in accordance with an embodiment of the present invention.

FIG. 21 is an exploded, perspective view of a flow regulator system in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
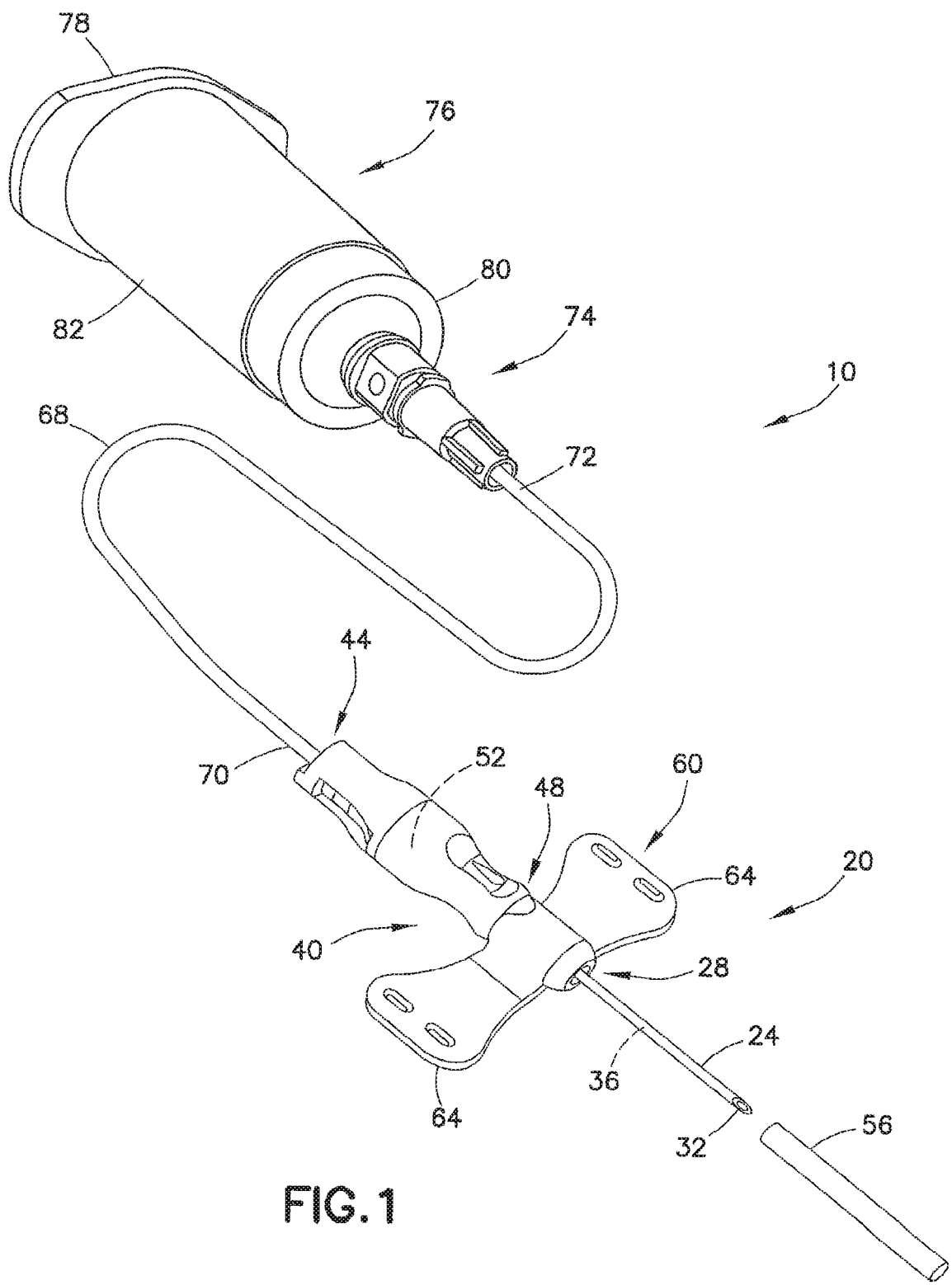
FIG. 1 is a perspective view of a blood collection device with tubing in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a specimen collection assembly in accordance with the present disclosure.

FIGS. 2-13E illustrate an exemplary embodiment of the present disclosure directed to a manual blood flow regulation device which regulates the flow of blood from the vasculature of a patient by manually varying the length of an orifice or flow path. Referring to FIGS. 2-13E, a flow regulator system 100 includes a tube holder sub-assembly 102, gaskets 104a and 104b, a flow control member or dial 106, a spine 108, a hub 110, a non-patient needle 112, a sleeve 114, and a tube holder 116.

Referring to FIGS. 5A-5E, tube holder sub-assembly 102 includes a body portion 120, a flange portion 122 having a superior surface 124 and an opposing inferior surface 126, and a flow member 128. Body portion 120 extends from superior surface 124 of flange portion 122 and includes an exterior wall 131 and an interior wall 132. Interior wall 132 of body portion 120 defines a bore 136 through tube holder sub-assembly 102. In one embodiment, interior wall 132 includes two interior wall components 132a and 132b that define respective opposing slots 134a and 134b. Slots 134a and 134b are sized and shaped to receive respective rails 178 (FIGS. 8A-8D) of spine 108 to secure tube holder sub-assembly 102 to spine 108 as will be described in more detail below. In one embodiment, flow member 128 is disposed adjacent a portion of exterior wall 131 of body portion 120. Flow member 128 defines a flow channel 130 therein such that flow channel 130 extends the extent of tube holder sub-assembly 102. For example, flow channel 130 includes a first opening 133 at a top portion of flow member 128 and a second opening 135 (FIG. 5E) at inferior surface 126 of flange portion 122. In this manner, a fluid such as blood is able to flow through tube holder sub-assembly 102 via flow channel 130 as will be described in more detail below. FIGS. 5A-5E illustrate flow member 128 and flow channel 130 as elongated cylindrical members, though it is contemplated that other shapes and sizes of flow member 128 and flow channel 130 may be used. For example, flow member 128 and flow channel 130 can have other multisided polygon cross-sectional shapes, such as square or rectangular cross-sectional shapes.

Referring to FIG. 5E, inferior surface 126 of flange portion 122 defines a gasket receiving cavity 138 and opposing gasket protuberance apertures 140 therein. Gasket receiving cavity 138 and gasket protuberance apertures 140 are sized and shaped to receive gasket 104*b* within inferior surface 126 of flange portion 122 of tube holder sub-assembly 102 as shown in FIG. 3GB. In this manner, gasket 104*b* is able to provide a substantially leak proof seal between tube holder sub-assembly 102 and dial 106.

Referring to FIG. 6, gasket 104*a*, 104*b* includes a gasket body 142, a gasket through-port such as gasket flow aperture 144 defined therethrough, and opposing gasket protuberances 146. For the sake of brevity, only one gasket is shown in FIG. 6 which corresponds to both gasket 104*a* and gasket 104*b* as gaskets 104*a* and 104*b* each include the same structure.

Referring to FIG. 3GB, gasket 104*b* is secured to tube holder sub-assembly 102 such that gasket body 142 is received within gasket receiving cavity 138 (FIG. 5E) with gasket protuberances 146 received within respective gasket protuberance apertures 140 (FIG. 5E) of tube holder sub-assembly 102. In this manner, gasket 104*b* is secured within tube holder sub-assembly 102 so that gasket 104*b* is prevented from rotating relative to tube holder sub-assembly 102. Additionally, gasket 104*b* is secured to tube holder sub-assembly 102 such that gasket flow aperture 144 is in alignment with second opening 135 (FIG. 5E) of flow channel 130 of tube holder sub-assembly 102 as will be described in more detail below.

Figure 7A:
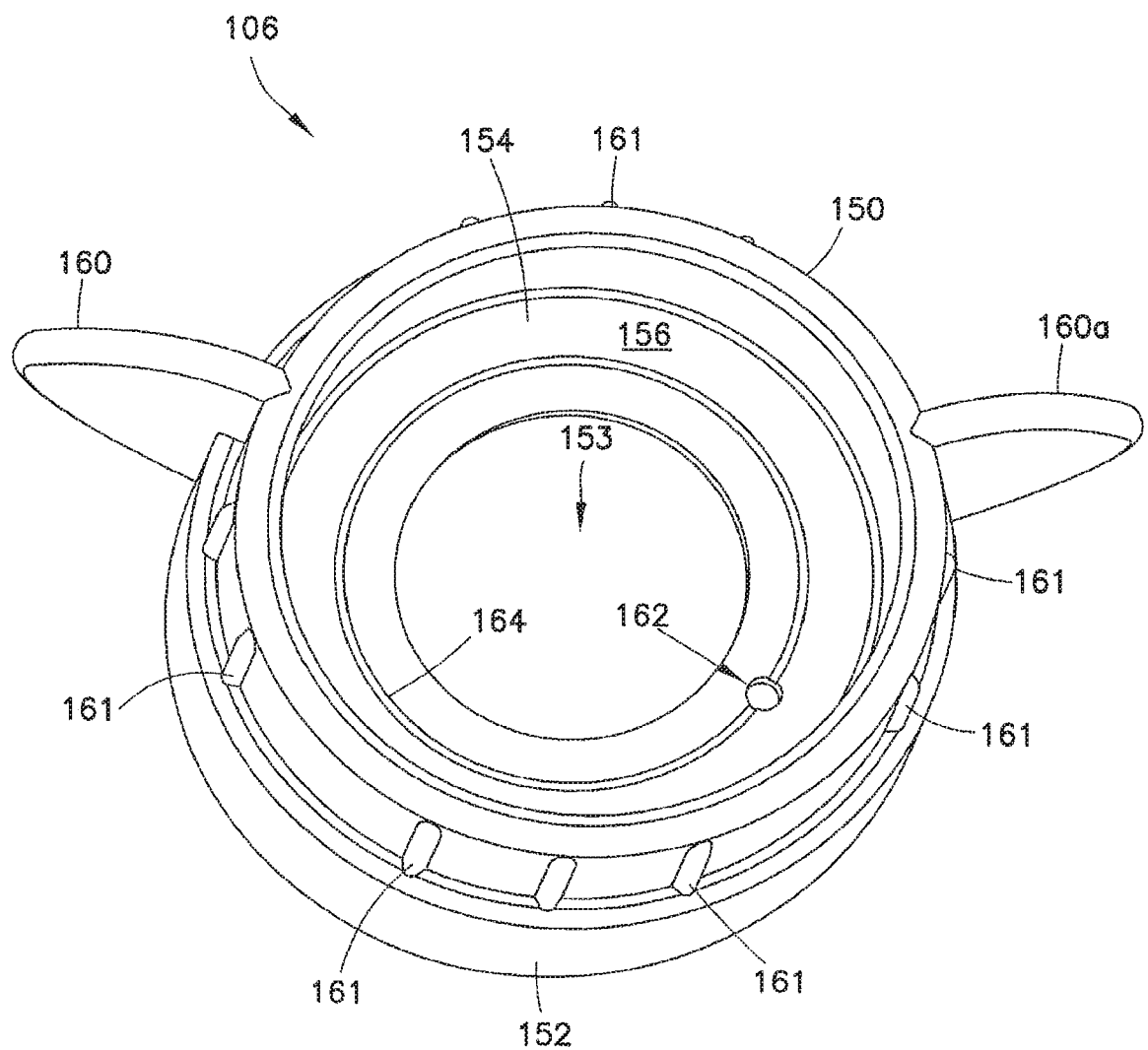
FIG. 7A is a plan perspective view of a dial of the flow regulator system of FIG. 2 in accordance with an embodiment of the present invention.

Referring to FIGS. 7A-7C, flow control member or dial 106 includes an upper body portion 150, a lower body portion 152, and a center plate 154 disposed therebetween and within body portions 150, 152. The walls of upper body portion 150 and lower body portion 152 together define center bore 153 through dial 106. Dial 106 also includes at least one flange 160, such as opposing flanges 160, 160*a* extending from an exterior surface of upper body portion 150 and lower body portion 152. In one embodiment, flanges 160, 160*a* extend parallel to the longitudinal axis of dial 106. Flanges 160, 160*a* may be configured for easy grasping of dial 106 by a medical practitioner. In this manner, a medical practitioner may easily rotate dial 106 relative to flow regulator system 100 to adjustably alter a flow path as will be described in more detail below. FIGS. 7A-7C illustrate dial 106 having two (2) flanges 160, 160*a*, though it is contemplated that other numbers of flanges 160 could be provided on dial 106. For example, three (3) or more flanges 160 may be used. Referring to FIGS. 7A-7C, upper body portion 150 may also include a plurality of ribs 161 extending from an exterior surface. Ribs 161 provide a further gripping surface for a medical practitioner.

Referring to FIGS. 7A and 7B, center plate 154 includes a superior surface 156 and an opposing inferior surface 158. Referring to FIG. 7A, superior surface 156 of center plate 154 defines through-port or flow aperture 162 through center plate 154 and a front flow channel 164. In one embodiment, front flow channel 164 extends three-hundred sixty (360) degrees around superior surface 156 from flow aperture 162 as shown in FIG. 7A. In this manner, the entirety of front flow channel 164 is in fluid communication with flow aperture 162. Flow aperture 162 allows a fluid to pass from superior surface 156 of center plate 154 through center plate 154 to inferior surface 158. In other embodiments, front flow channel 164 may extend any number of degrees around superior surface 156. For example, front flow channel 164 may extend about only a portion of superior surface 156.

Referring to FIG. 7B, inferior surface 158 of center plate 154 defines a back flow channel 166 and includes flow aperture 162. In one embodiment, back flow channel 166 extends one-hundred twenty (120) degrees around inferior surface 158 from flow aperture 162 as shown in FIG. 7B. In this manner, a fluid that passes through flow aperture 162 to inferior surface 158 can travel within back flow channel 166 one-hundred twenty (120) degrees from flow aperture 162 as will be described in more detail below. In other embodiments, back flow channel 166 may extend any number of degrees around inferior surface 158. For example, back flow channel 166 may extend three-hundred sixty (360) degrees around inferior surface 158. In such embodiments, a fluid that passes through flow aperture 162 to inferior surface 158 can travel within back flow channel 166 any number of degrees around inferior surface 158 from flow aperture 162.

In one embodiment, the length that back flow channel 166 extends around superior surface 156 of center plate 154 corresponds to the degree that dial 106 can be rotated relative to system 100. For example, referring to FIG. 7B, if dial 106 can be rotated relative to system 100 by one-hundred twenty (120) degrees, then back flow channel 166 correspondingly extends one-hundred twenty (120) degrees around inferior surface 158. Inferior surface 158 also includes detents 168 for controlling movement of dial 106 relative to spine 108 as will be discussed below.

Figure 8A:
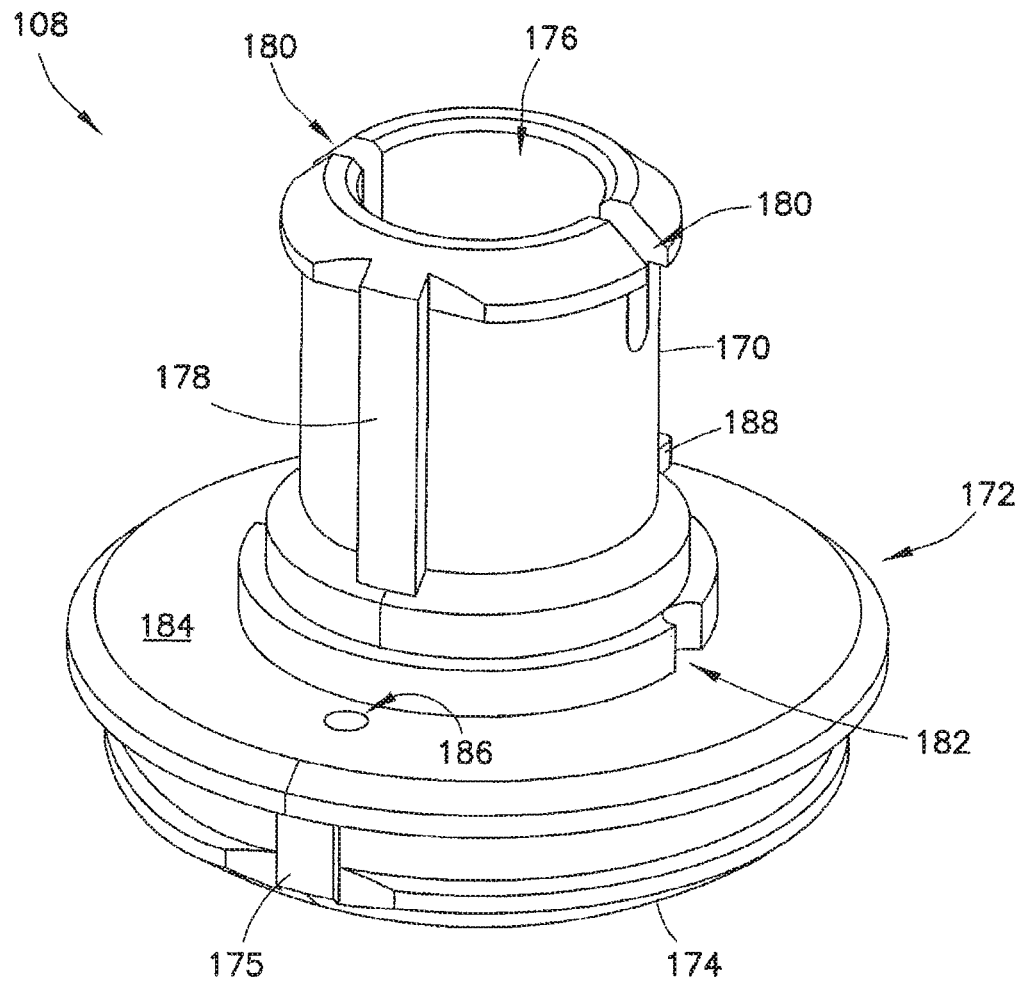
FIG. 8A is a perspective view of a spine of the flow regulator system of FIG. 2 in accordance with an embodiment of the present invention.
Figure 8B:
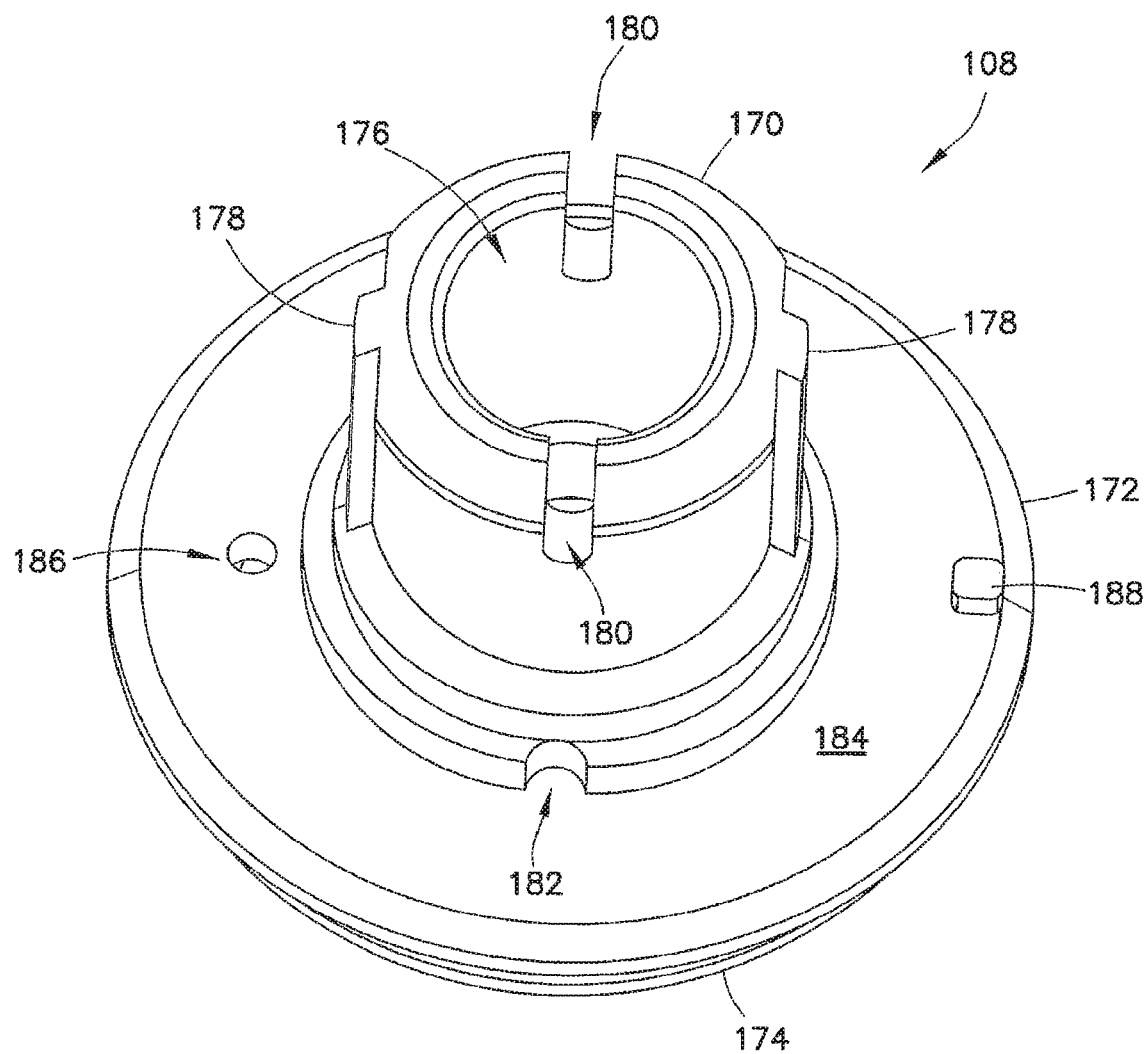
FIG. 8B is a plan perspective view of the spine of FIG. 8A in accordance with an embodiment of the present invention.
Figure 8C:
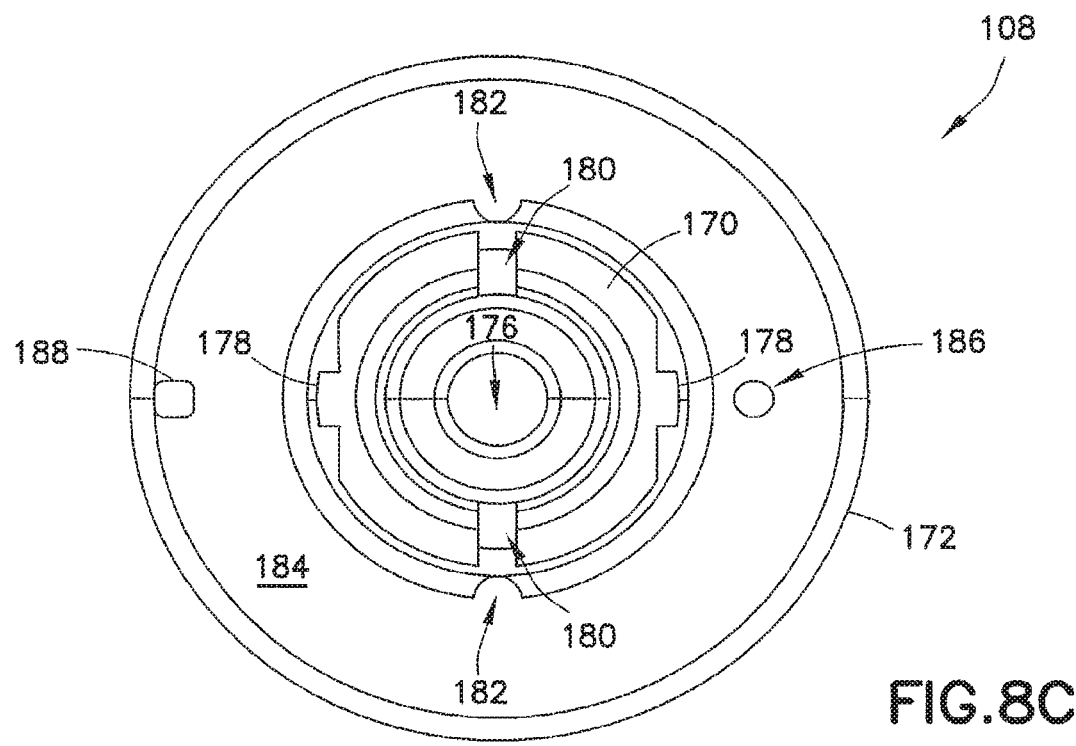
FIG. 8C is a plan view of the spine of FIG. 8A in accordance with an embodiment of the present invention.
Figure 8D:
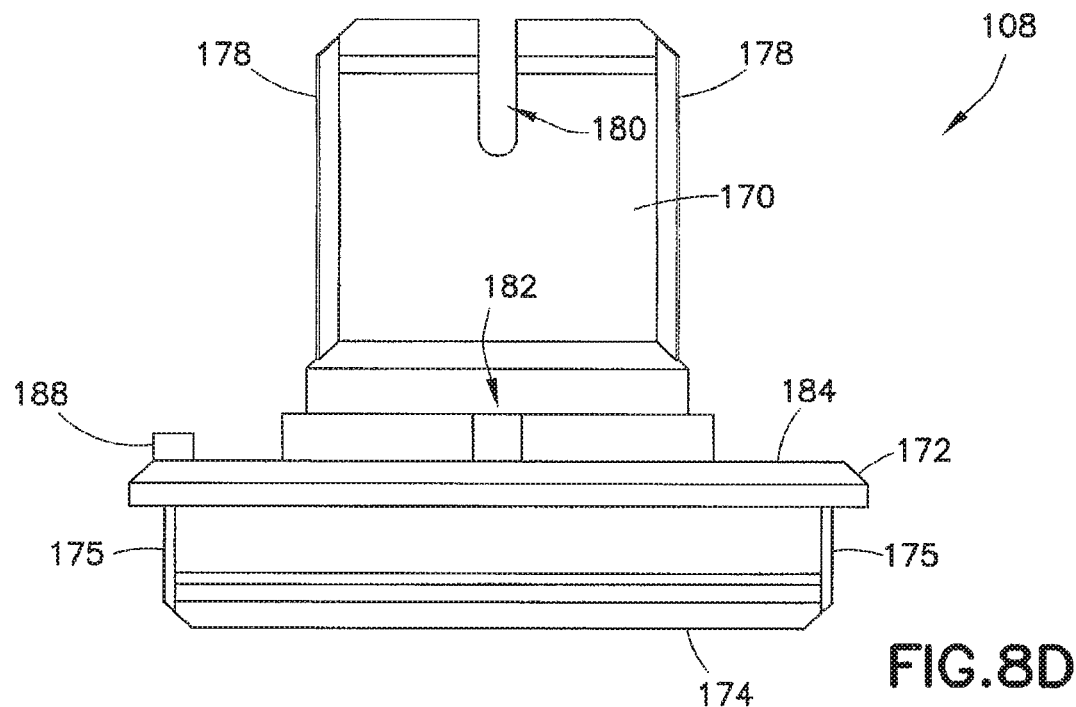
FIG. 8D is a side elevation view of the spine of FIG. 8A in accordance with an embodiment of the present invention.
Figure 11A:
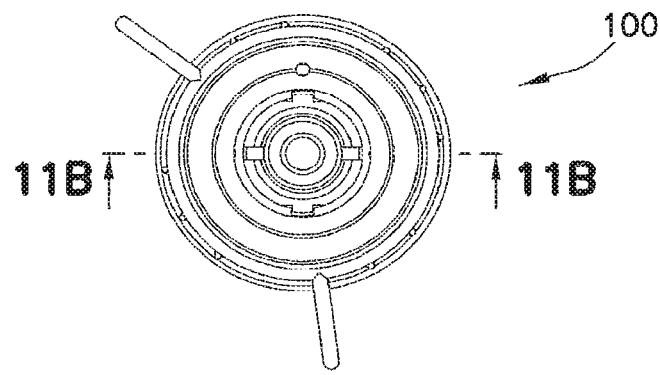
FIG. 11A is a plan view of the flow regulator system of FIG. 2 in accordance with an embodiment of the present invention.
Figure 11C:
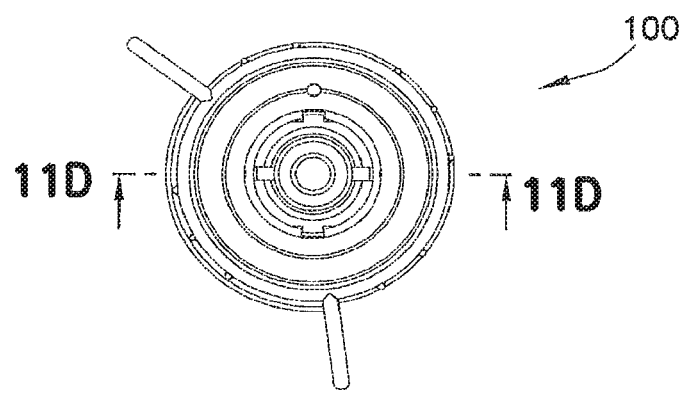
FIG. 11C is a plan view of the flow regulator system of FIG. 2 in accordance with an embodiment of the present invention.
Figure 11E:
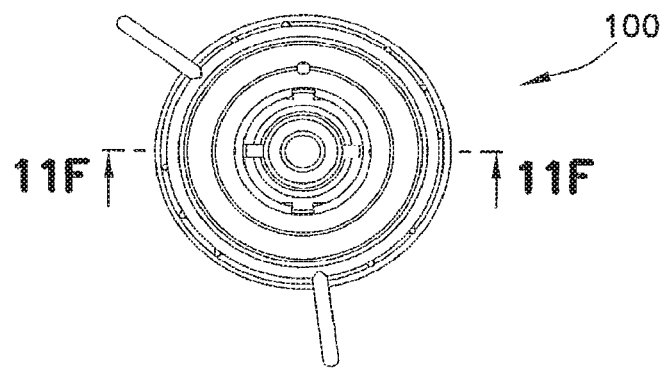
FIG. 11E is a plan view of the flow regulator system of FIG. 2 in accordance with an embodiment of the present invention.
Figure 11D:
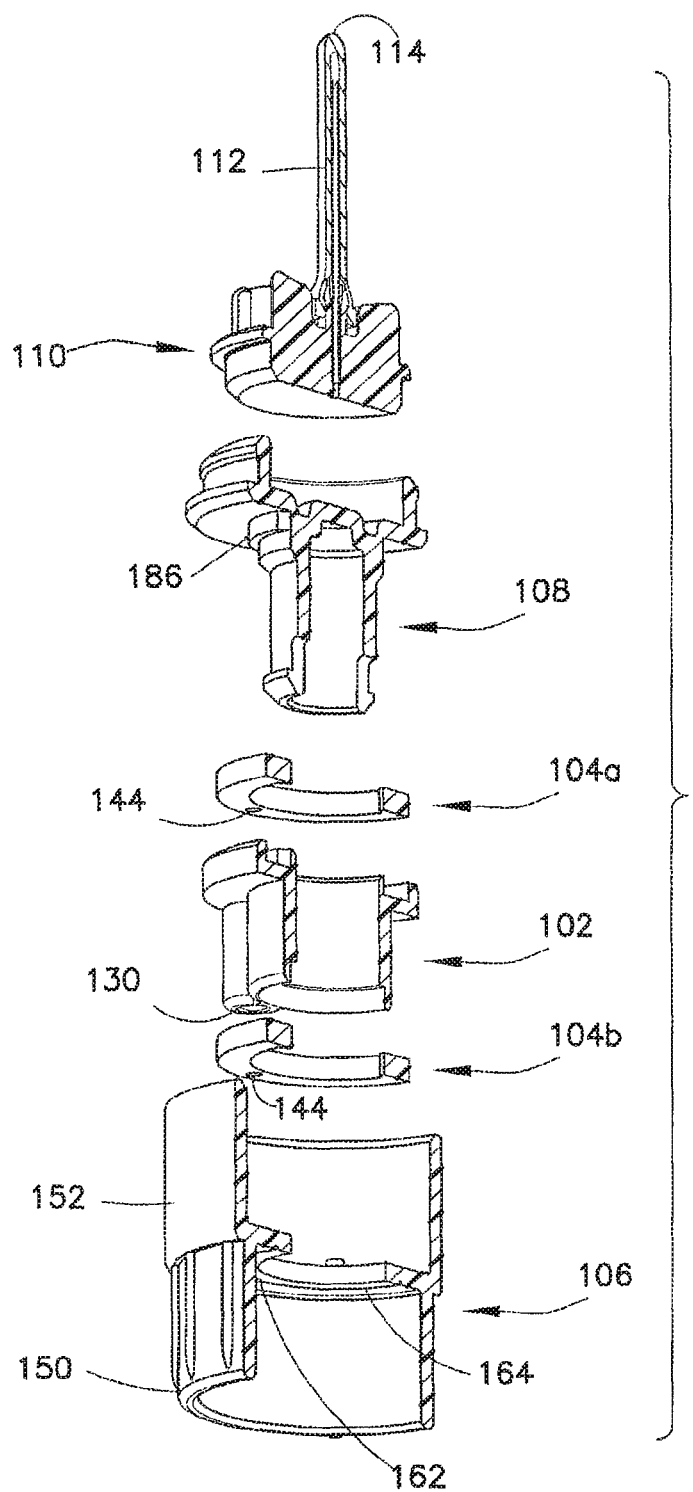
FIG. 11D is an exploded, cross-sectional view taken along line 11D-11D of FIG. 11C in accordance with an embodiment of the present invention.

Referring to FIGS. 8A-8D, spine 108 includes an axial protrusion or body portion 170, a flange portion 172, and a hub receiving portion 174. The walls of body portion 170, flange portion 172, and hub receiving portion 174 together define a center bore 176 through spine 108. In one embodiment, hub receiving portion 174 may include at least one tab 175 (FIG. 8A). Referring to FIG. 8D, hub receiving portion 174 may include two opposing tabs 175. In one embodiment, tabs 175 may be formed of a material that is slightly deformable. Tabs 175 provide a mechanism to secure spine 108 to tube holder 116 such that rotation between spine 108 and tube holder 116 is prevented (FIGS. 3DA and 3DB) as will be described in more detail below.

Body portion 170 of spine 108 includes opposing rails 178 which are each sized and shaped to be insertable into respective slots 134 of tube holder sub-assembly 102 to secure tube holder sub-assembly 102 to spine 108, i.e., with rails 178 of spine 108 secured within slots 134 of tube holder sub-assembly 102, rotation of tube holder sub-assembly 102 relative to spine 108 is prevented. Body portion 170 of spine 108 also defines opposing slots 180 at a top portion and gasket protuberance apertures 182 at a bottom portion. In one embodiment, opposing slots 180 of spine 108 provide respective snap arms on the spine component so that tube holder sub-assembly 102 and spine 108 can be secured together by a snap-fit. Flange portion 172 of spine 108 includes a gasket receiving surface 184 and defines a through-port or spine flow aperture 186 therethrough. Flange portion 172 also includes a detent 188 which is engageable with detents 168 of dial 106 to control movement of dial 106 relative to spine 108.

Referring to FIG. 3E, gasket 104*a* is secured to spine 108 such that gasket body 142 is received on gasket receiving surface 184 of spine 108 with gasket protuberances 146 received within respective gasket protuberance apertures 182 of spine 108. In this manner, gasket 104*a* is secured to spine 108 so that gasket 104*a* is prevented from rotating relative to spine 108. Additionally, gasket 104*a* is secured to spine 108 such that gasket flow aperture 144 is in alignment with spine flow aperture 186 of spine 108 as will be described in more detail below. Gaskets 104*a*, 104*b* provide a substantially leak proof seal between spine 108 and dial 106 and tube holder sub-assembly 102.

Referring to FIGS. 9A-9D, hub 110 includes a needle receiving member 190, a flange portion 192 having a superior surface 193 (FIGS. 9B and 9D) and an inferior surface 194 (FIGS. 9A-9C), a wall assembly 195 extending from inferior surface 194, and a spine connection portion 196 extending from superior surface 193. Needle receiving member 190 defines a flow collection channel 198 through hub 110 and includes a flow entrance aperture 200 (FIG. 9D) at a bottom surface of spine connection portion 196. Needle receiving member 190 is sized and shaped to receive non-patient needle 112 therein as shown in FIG. 3CA.

Referring to FIGS. 2, 3DA, and 3DB, tube holder 116 includes a distal end 202, a proximal end 204, and a flange 208 at proximal end 204. Tube holder 116 defines an interior cavity 206 between distal end 202 and proximal end 204.

Figure 3I:
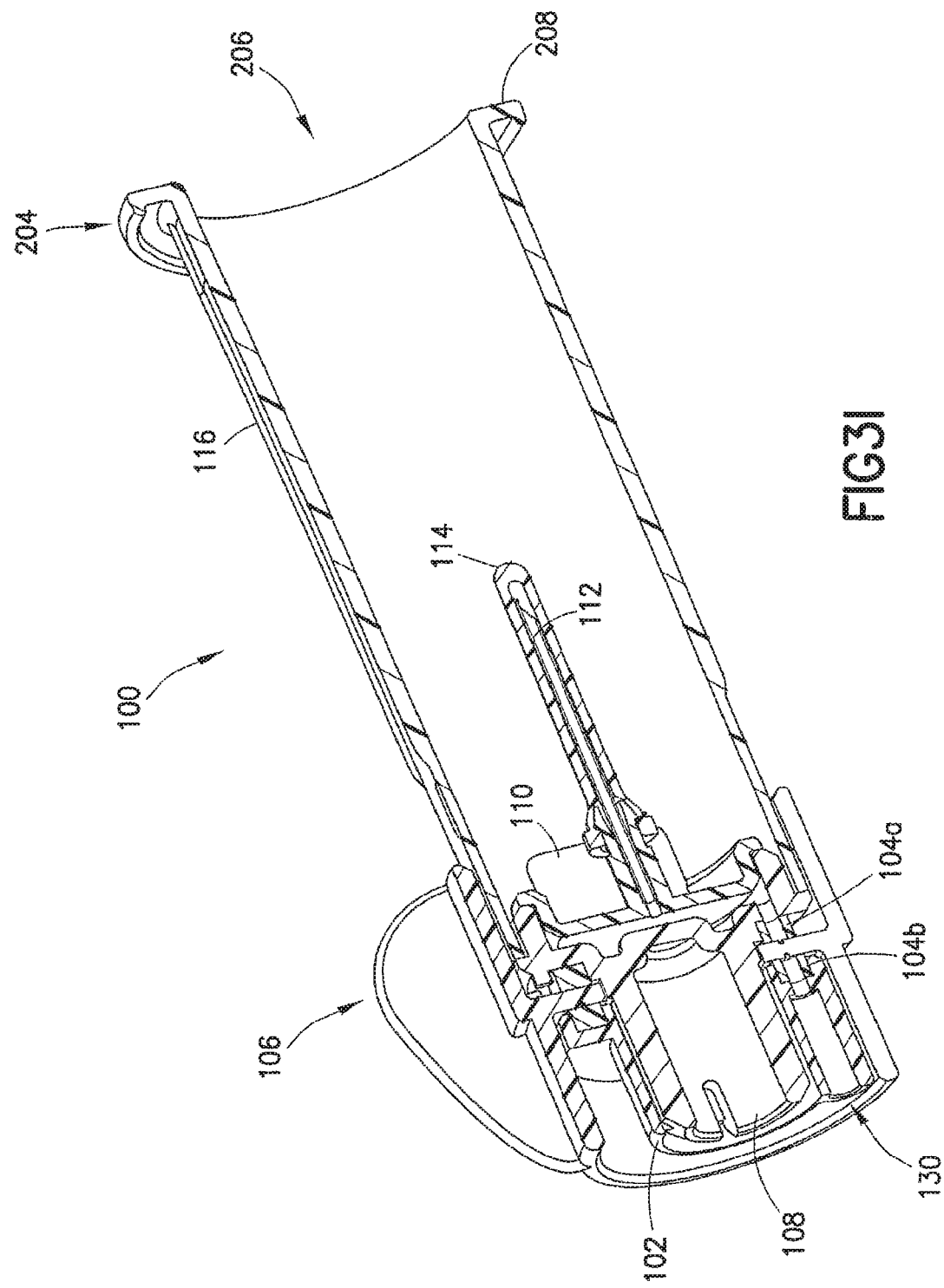
FIG. 3I is a cross-sectional view taken along line 3I-3I of FIG. 3HA in accordance with an embodiment of the present invention.

Referring to FIGS. 3A-3I, to assemble flow regulator system 100 spine connection portion 196 (FIGS. 9A, 9B, and 9D) of hub 110 may be received within hub receiving portion 174 of spine 108 as shown in FIGS. 3BA, 3BB, and 10. Spine 108 and hub 110 can be secured together using a standard fabrication technique such as welding or bonding. In one embodiment, spine 108 and hub 110 can be ultrasonically welded together. With spine 108 and hub 110 secured together as shown in FIGS. 3A, 3BA, 3BB, and 10, spine 108 is prevented from rotating relative to hub 110. Next, referring to FIGS. 3CA and 3CB, non-patient needle 112 can be secured within needle receiving member 190 (FIGS. 9A-9C) of hub 110 such that the lumen of needle 112 is in fluid communication with flow collection channel 198 (FIGS. 9A-9C) and flow entrance aperture 200 (FIG. 9D) of hub 110. Referring to FIGS. 3CA and 3CB, in one embodiment, sleeve 114 can be provided over needle 112 to prevent accidental needle stick injuries to a user of system 100.

Referring to FIGS. 3DA and 3DB, spine 108, hub 110, and needle 112 (disposed within sleeve 114) may be engaged with tube holder 116. For example, hub receiving portion 174 (FIGS. 8A, 8B, and 8D) of spine 108 may be inserted into distal end 202 of tube holder 116. Force exerted on spine 108 moves spine 108 within interior cavity 206 of tube holder 116 until the bottom surface of flange portion 172 (FIGS. 8A-8D) of spine 108 contacts the end surface of the wall of tube holder 116 at distal end 202. In this manner, tabs 175 and hub receiving portion 174 contact the interior surface of the wall of tube holder 116 so that spine 108 is secured to tube holder 116 such that rotation between spine 108 and tube holder 116 is prevented as shown in FIGS. 3DA and 3DB.

In an alternative embodiment, spine 108 may be engaged with tube holder 116 by threadingly engaging a threaded portion of spine 108 to a threaded portion of tube holder 116. In other embodiments, spine 108 may be engaged with tube holder 116 using a ball detent, locking tabs, spring loaded locking mechanism, latch, adhesive, snap fit mechanism, or other similar mechanism. In all embodiments, spine 108 is locked, secured, or engaged with tube holder 116, i.e., significant relative movement or rotation between spine 108 and tube holder 116 is prevented.

Referring to FIG. 3E, with spine 108 and hub 110 engaged with tube holder 116, gasket 104*a* may then be secured to spine 108 as described above. Referring to FIG. 3F, dial 106 may then be assembled to spine 108. Dial 106 is engaged with spine 108 so that dial 106 is rotatable relative to spine 108. In one embodiment, detents 168 (FIG. 7B) of dial 106 are configured to control the degree that dial 106 can rotate relative to spine 108. For example, detents 168 of dial 106 and detent 188 of spine 108 together define the boundaries of rotation of dial 106 relative to spine 108, i.e., rotation of dial 106 in a first direction is limited to a position in which a first detent 168 of dial 106 engages detent 188 (FIGS. 8A-8D) of spine 108 and rotation of dial 106 in a second direction is limited to a position in which a second detent 168 of dial 106 engages detent 188 of spine 108. In this manner, the configuration and position of detents 168 of dial 106 can be varied to determine the amount of rotation of dial 106 relative to spine 108 that is desired. Referring to FIGS. 3HA, 3HB, and 3I, dial 106 is prevented from being removed from spine 108 by the securement of tube holder sub-assembly 102 to spine 108 as will be described below.

Referring to FIGS. 3GA and 3GB, before tube holder sub-assembly 102 is secured to spine 108, gasket 104*b* is secured to tube holder sub-assembly 102 as described above. Referring to FIGS. 3HA and 3HB, with gasket 104*b* (FIG. 3GB) secured to tube holder sub-assembly 102, tube holder sub-assembly 102 can be secured to spine 108 by aligning respective slots 134*a*, 134*b* (FIG. 5C) of tube holder sub-assembly 102 with respective rails 178 (FIGS. 8A-8D) of spine 108 and then tube holder sub-assembly 102 can be slidably received over spine 108. In this manner, tube holder sub-assembly 102 is secured to spine 108, i.e., with rails 178 (FIGS. 8A-8D) of spine 108 secured within slots 134*a*, 134*b* (FIG. 5C) of tube holder sub-assembly 102, such that rotation of tube holder sub-assembly 102 relative to spine 108 is prevented.

Figure 4A:
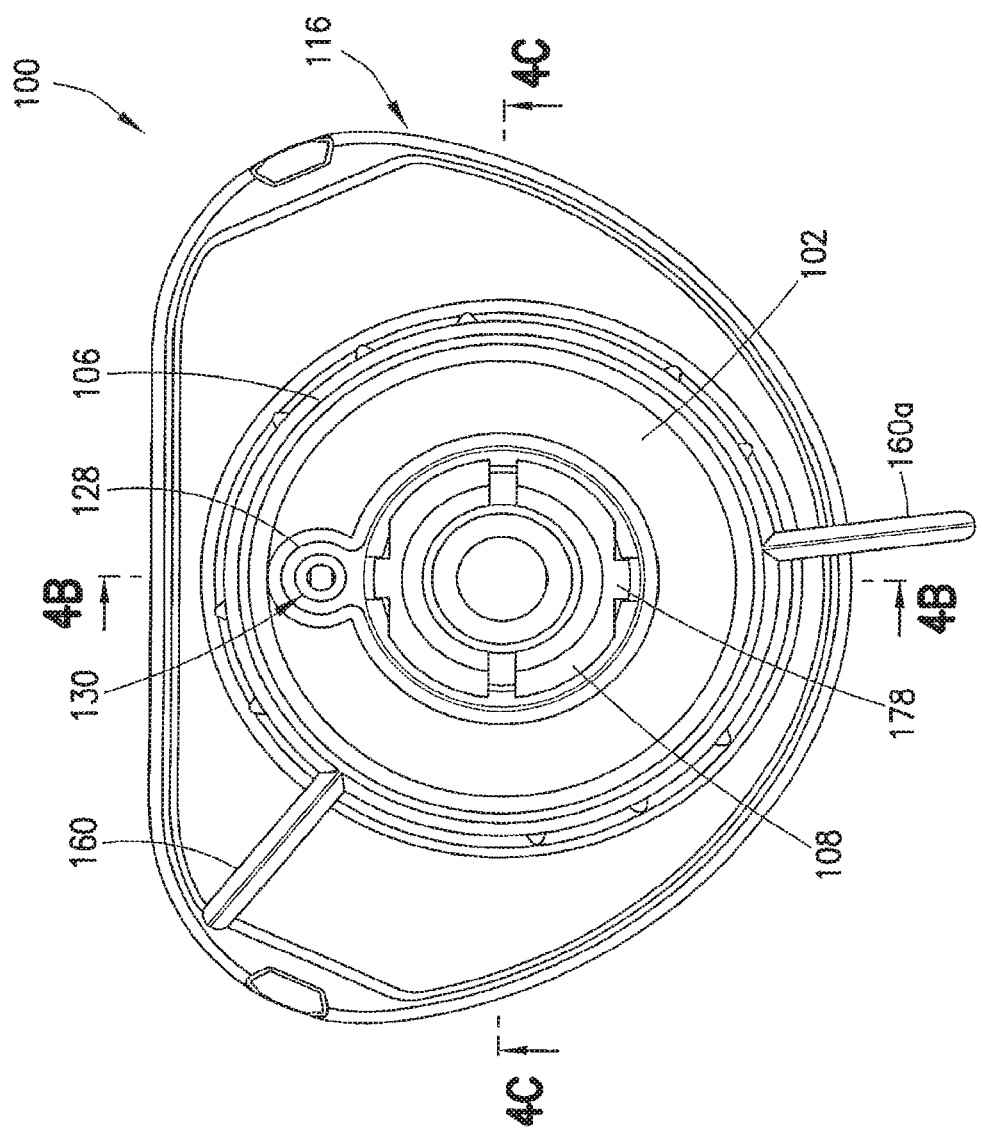
FIG. 4A is a plan view of the flow regulator system of FIG. 2 in accordance with an embodiment of the present invention.
Figure 4B:
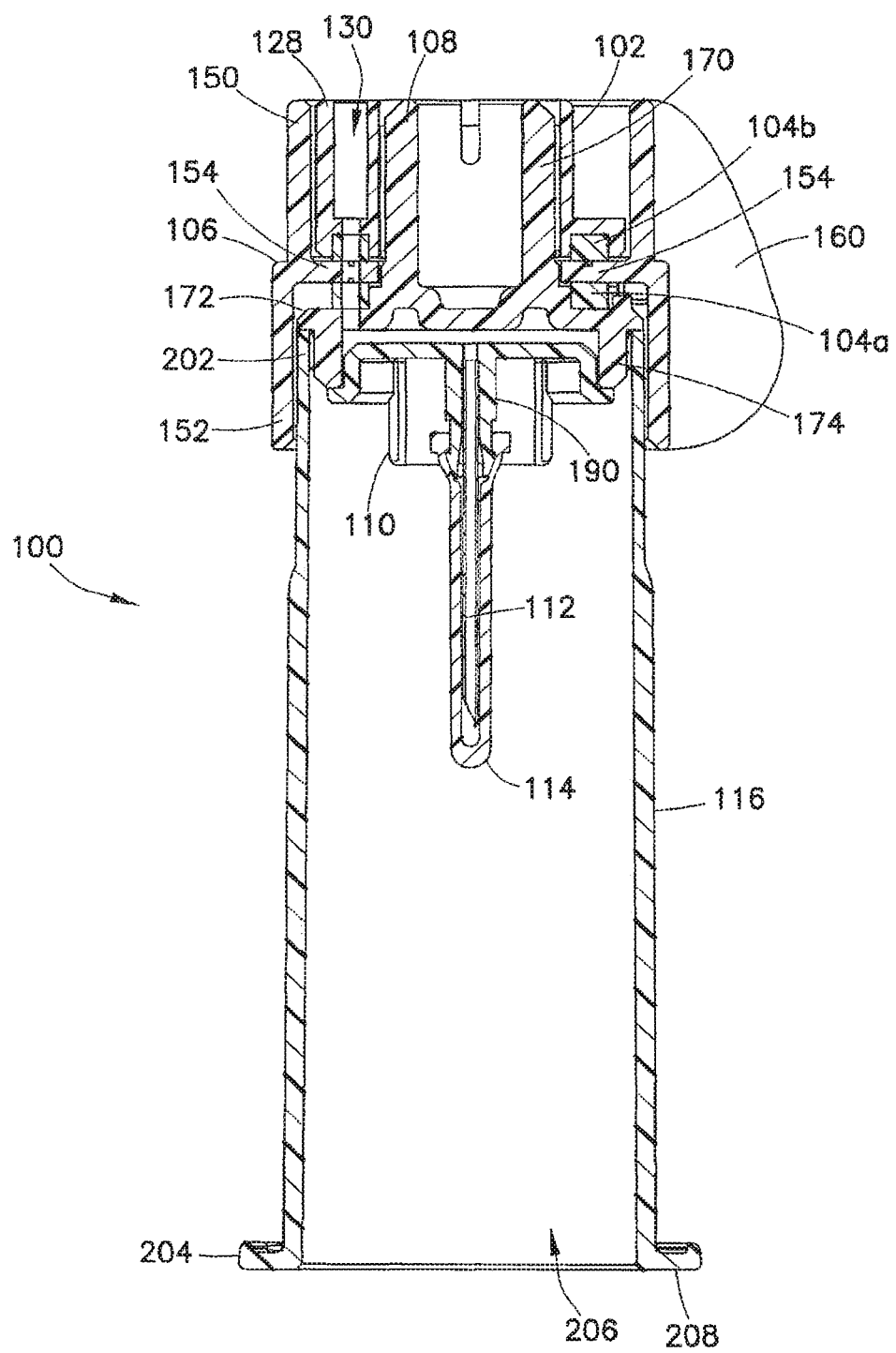
FIG. 4B is a cross-sectional view taken along line 4B-4B of FIG. 4A in accordance with an embodiment of the present invention.
Figure 4C:
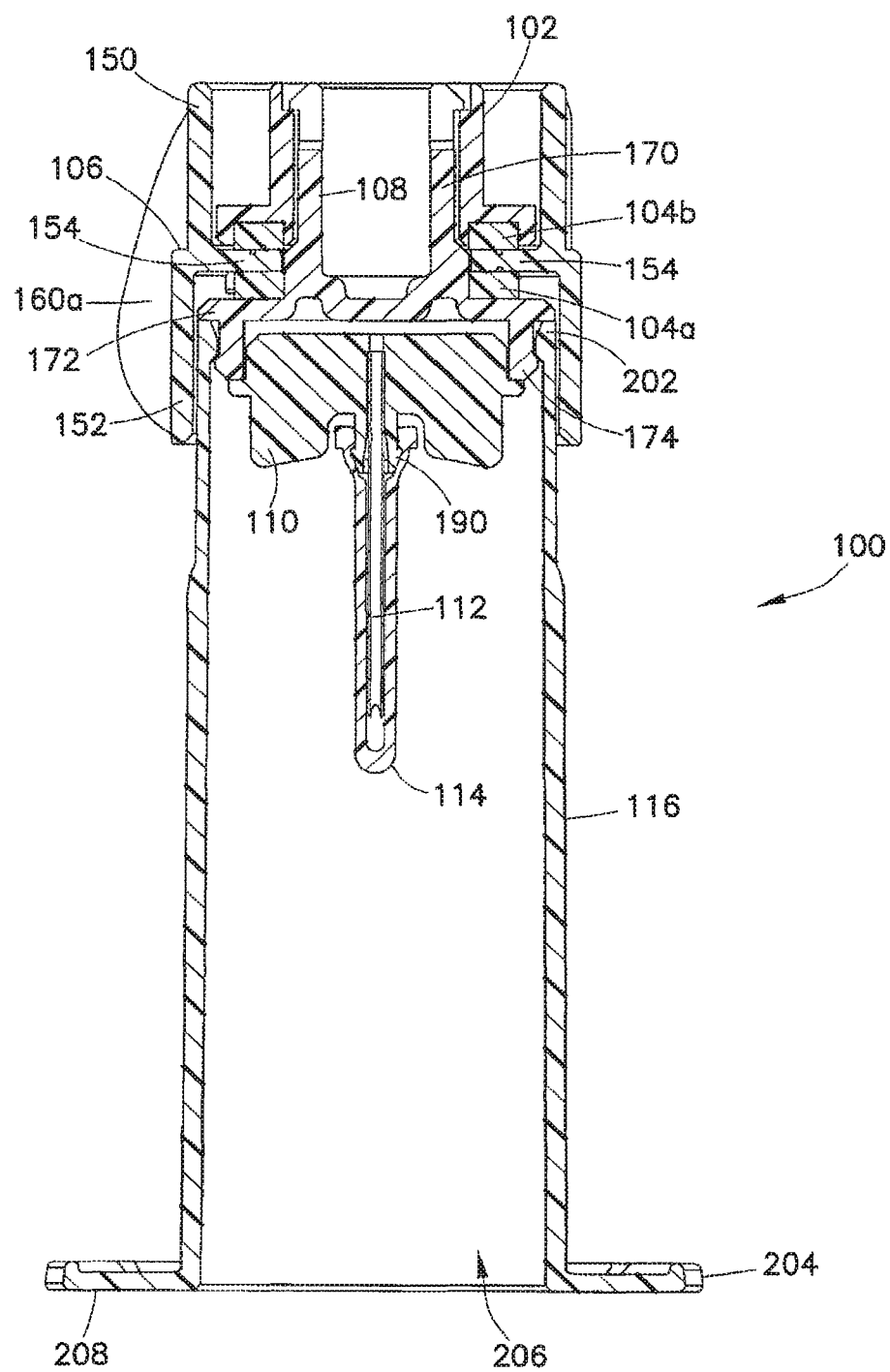
FIG. 4C is a cross-sectional view taken along line 4C-4C of FIG. 4A in accordance with an embodiment of the present invention.

In one embodiment, corresponding locking features, such as a snap fit mechanism, are included on tube holder sub-assembly 102 and spine 108, respectively, to further secure tube holder sub-assembly 102 to spine 108. For example, tube holder sub-assembly 102 and spine 108 may respectively include a ball detent system, locking tabs, spring loaded locking mechanism, latch, adhesive, snap fit mechanism, or other similar mechanisms. Tube holder sub-assembly 102 may be secured to spine 108 with center plate 154 of dial 106 positioned between tube holder sub-assembly 102 and spine 108 as shown in FIGS. 4B and 4C. In this manner, dial 106 is secured to tube holder 116 while being rotatable relative to tube holder sub-assembly 102 and spine 108 as will be described in more detail below. Referring to FIGS. 3A, 4B, 4C, 3HA, 3HB, and 3I, assembled flow regulator system 100 is shown with dial 106 being rotatable relative to tube holder sub-assembly 102 and spine 108.

Phlebotomy procedures are often carried out using a blood collection device, such as an evacuated blood collection container. The manual blood flow regulation device of the present invention may be used with blood collection devices such as a blood collection device 10 shown in FIG. 1. Referring to FIG. 1, blood collection device 10 includes a needle assembly 20 with a cannula 24 that has a proximal end 28, a pointed distal end 32, and a lumen 36 extending between the ends. The needle assembly 20 also includes a hub 40 with a proximal end 44, a distal end 48, and a passage 52 extending between the ends. The proximal end 28 of the cannula 24 is mounted in the passage 52 of the hub 40 so that the lumen 36 through the cannula 24 communicates with the passage 52 through the hub 40. A shield 56 may be provided for shielding the cannula pointed distal end 32 after use. The blood collection device 10 may also include a wingset 60 that projects transversely from the hub 40 or from the shield 56. Wings 64 of the wingset 60 can be folded into face-to-face relationship with one another to define a handle that facilitates manipulation of the needle assembly 20. The wings 64 can then be rotated away from one another and held against the skin of the patient.

Blood collection device 10 also includes a length of flexible plastic tubing 68. The tubing 68 has a distal end 70 that is connected to the proximal end 44 of the hub 40 and communicates with the lumen 36 of the needle cannula 24. The end of the plastic tube, i.e., a proximal end 72 of tubing 68, remote from the needle cannula 24 may include a fitting or fixture 74 for connecting the needle cannula 24 to a blood collection tube or other receptacle. The specific construction of the fixture 74 will depend upon the characteristics of the receptacle to which the fixture is to be connected.

Phlebotomy procedures often employ evacuated tubes, such as the VACUTAINER® brand of evacuated tubes sold by Becton, Dickinson and Company, the assignee of the present invention. Evacuated tubes often are used with a tube holder 76 that has a proximal end 78, a distal end 80, and a tubular side wall 82 extending between the ends. The proximal end 78 of the holder 76 is widely open and is configured for slidably receiving the evacuated tube. The distal end 80 of the holder 76 typically includes an end wall with a mounting aperture. The tube holder 76 may be used with a non-patient needle assembly that has a non-patient hub configured for cooperation with the mounting aperture of the holder 76. The non-patient needle assembly further includes a non-patient cannula extending proximally from the hub and into the tube holder 76.

The blood collection device 10 may be used by mounting the fitting 74 at the proximal end 72 of the flexible plastic tubing 68 to the distal end of the hub of the non-patient needle assembly. The pointed distal end 32 of the cannula 24 is urged into a targeted blood vessel, such as a vein, by gripping of the wings 64 of the wingset 60 for manipulation of the cannula 24. The wings 64 then may be folded into engagement with the skin of the patient and may be taped in position. An evacuated tube then is urged into the open proximal end 78 of the blood collection tube holder 76 so that the proximal end of the non-patient needle pierces the stopper of the evacuated tube. As a result, the blood vessel of the patient is placed in communication with the interior of the evacuated tube, and the pressure differential between the blood vessel and the evacuated tube will generate a flow of blood through the cannula 24, through the passage 52 of the hub 40, through the flexible tubing 68, through the non-patient hub, and finally through the non-patient needle and into the evacuated tube.

In one embodiment, flow regulator system 100 (FIGS. 2 and 3A) may be used with blood collection device 10 to regulate the flow rate of the blood between the blood vessel of the patient and the evacuated tube. For example, in one embodiment, flexible plastic tubing, such as tubing 68 shown in FIG. 1, may be secured to tube holder sub-assembly 102 so that the tubing is in fluid communication with flow regulator system 100 via flow channel 130 of tube holder sub-assembly 102. The other end of the tubing may be secured to a needle assembly, such as needle assembly 20 shown in FIG. 1, which can be inserted in the vein of a patient for blood collection as described above. Additionally, an evacuated tube may be positioned into open proximal end 204 and into interior cavity 206 of tube holder 116 so that a proximal end of non-patient needle 112 pierces a stopper of the evacuated tube. As a result, the blood vessel or vein of the patient is placed in communication with the interior of the evacuated tube for a phlebotomy procedure. In this manner, a medical clinician or patient can perform a blood collection procedure in a standard manner using flow regulator system 100 to modulate the flow of blood coming from the vein of a patient by manually varying the effective length of an orifice or flow path, e.g., fluid flow path FFP. In another embodiment, flow regulator system 100 may be positioned directly on a tube holder, such as tube holder 116 as shown in FIG. 3A, with a patient needle extending from distal end 202 of tube holder 116. In this manner, the tubing, e.g., tubing 68 (FIG. 1), and the wingset, e.g., wingset 60 (FIG. 1), may be eliminated.

In another embodiment, a flow regulator system 300 (FIG. 16) may be used with blood collection device 10 (FIG. 1). For example, flow regulator system 300 may be positioned between distal end 70 (FIG. 1) and proximal end 72 (FIG. 1) of tubing 68 to regulate the flow rate of the blood between the blood vessel of the patient and the evacuated tube as will be described in more detail below.

Referring to FIGS. 2-13E, the use of flow regulator system 100 to adjustably alter a flow path will now be described. Flow regulator system 100 is capable of acting to slow down the initial flow rate of blood into an evacuated blood collection device as a result of the application of a strong vacuum pressure from the evacuated blood collection device on the patient's accessed vasculature. The flow regulator system 100 is responsive to the initial spike in vacuum pressure from the evacuated blood collection device and slows down the draw of blood in order to avoid rapid depletion of blood from the patient to prevent the collapse of the patient's blood vessel during blood collection. In the embodiment shown in FIGS. 2-13E, the flow of blood coming from the vein of a patient is modulated by manually varying the effective length of the fluid flow path FFP of the regulator as shown in FIGS. 12A and 13A.

Referring to FIGS. 11A-13E, with flow regulator system 100 in a maximum flow position, a minimum flow position, or any position therebetween, flow channel 130 (FIG. 5A) of tube holder sub-assembly 102 is aligned with a gasket flow aperture 144 of a first gasket 104b (FIG. 3GB). Additionally, flow channel 130 (FIG. 5A) of tube holder sub-assembly 102 is aligned with a gasket flow aperture 144 of a second gasket 104a (FIG. 3E) and flow aperture 186 (FIG. 8A) of spine 108. To adjustably alter a flow path using flow regulator system 100, dial 106 is rotated relative to tube holder sub-assembly 102 and spine 108, i.e., flow aperture 162 of dial 106 is rotated relative to flow channel 130 of tube holder sub-assembly 102 and flow aperture 186 of spine 108.

Referring to FIGS. 11A-11F and 12A-12E, flow regulator system 100 is shown in a maximum flow position. In this position, flow aperture 162 of dial 106 is aligned with flow channel 130 of tube holder sub-assembly 102 and flow aperture 186 of spine 108 as shown in FIGS. 11A-11F and 12A. In this manner, an effective flow distance is minimized and the flow of a fluid, such as blood, is not impeded.

Figure 12A:
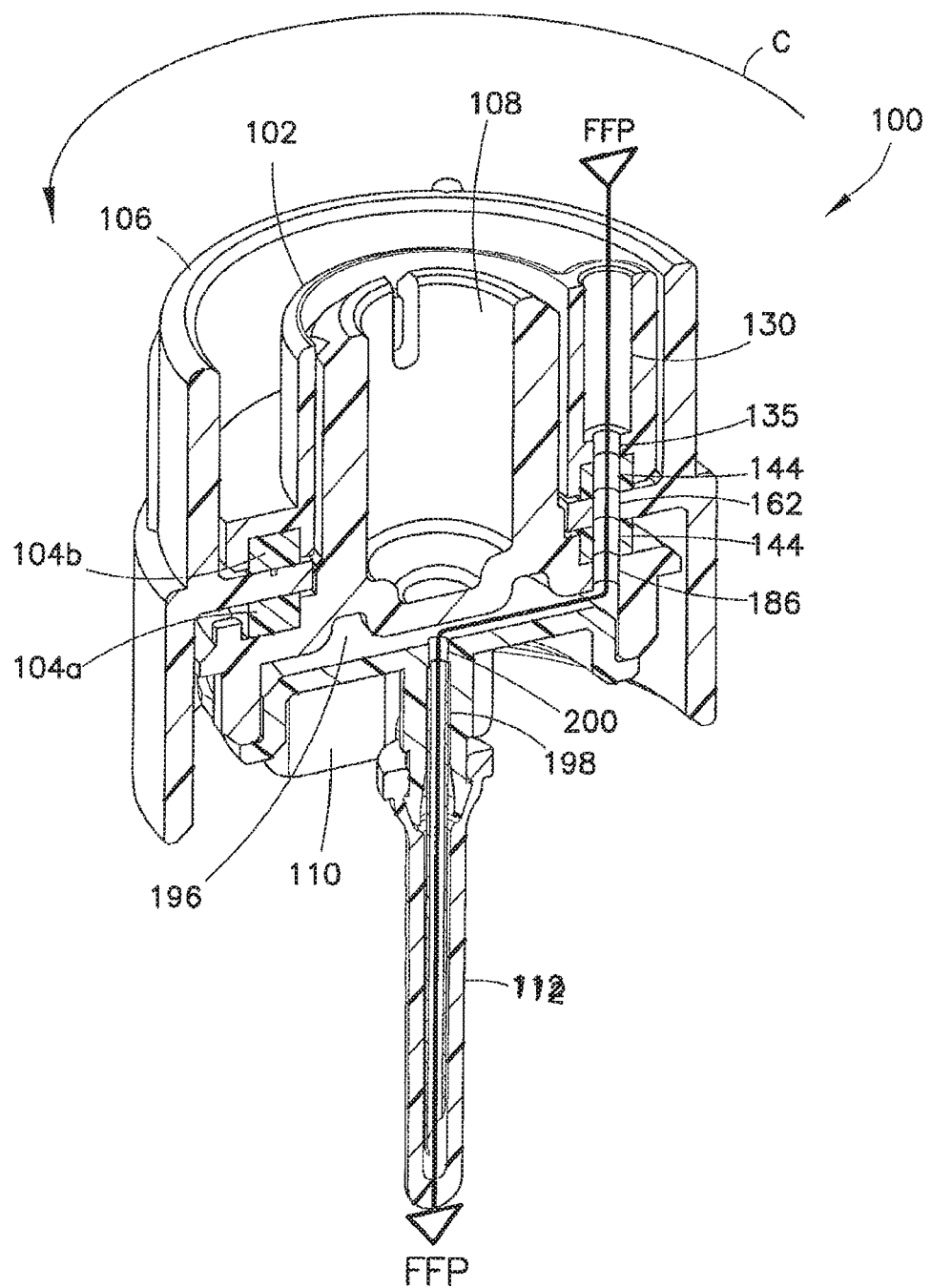
FIG. 12A is an assembled, cross-sectional perspective view of the flow regulator system of FIG. 2 in a maximum flow position in accordance with an embodiment of the present invention.
Figure 12B:
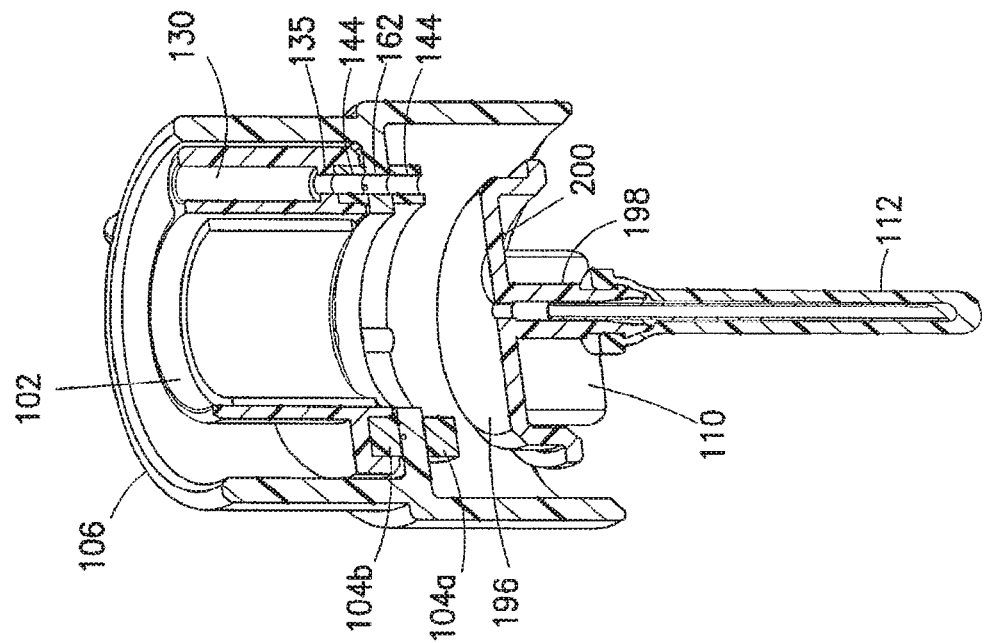
FIG. 12B is an assembled, cross-sectional perspective view of the flow regulator system of FIG. 12A in the maximum flow position with the spine removed in accordance with an embodiment of the present invention.
Figure 12C:
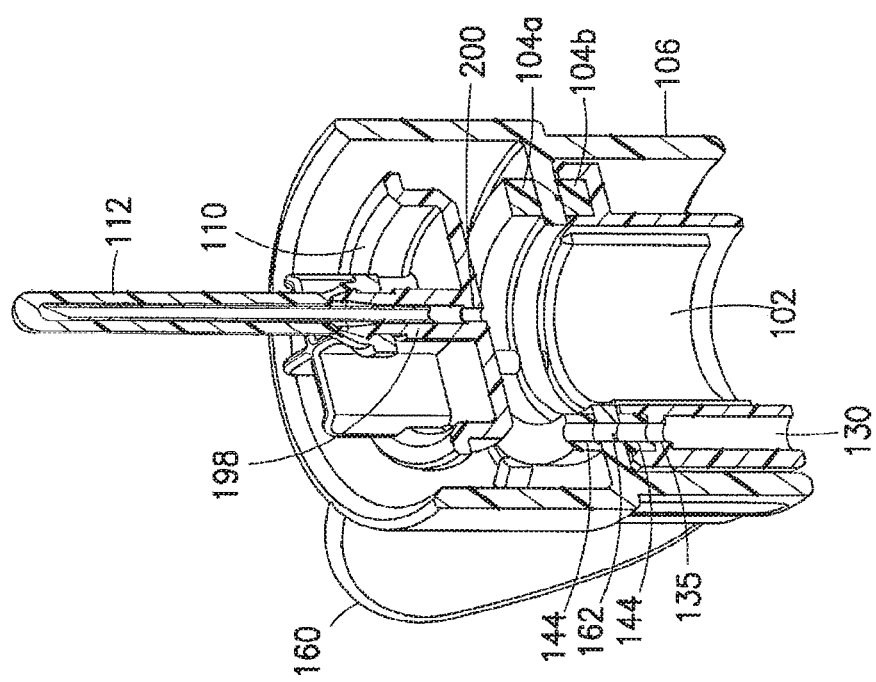
FIG. 12C is another assembled, cross-sectional perspective view of the flow regulator system of FIG. 12A in the maximum flow position with the spine removed in accordance with an embodiment of the present invention.
Figure 12E:
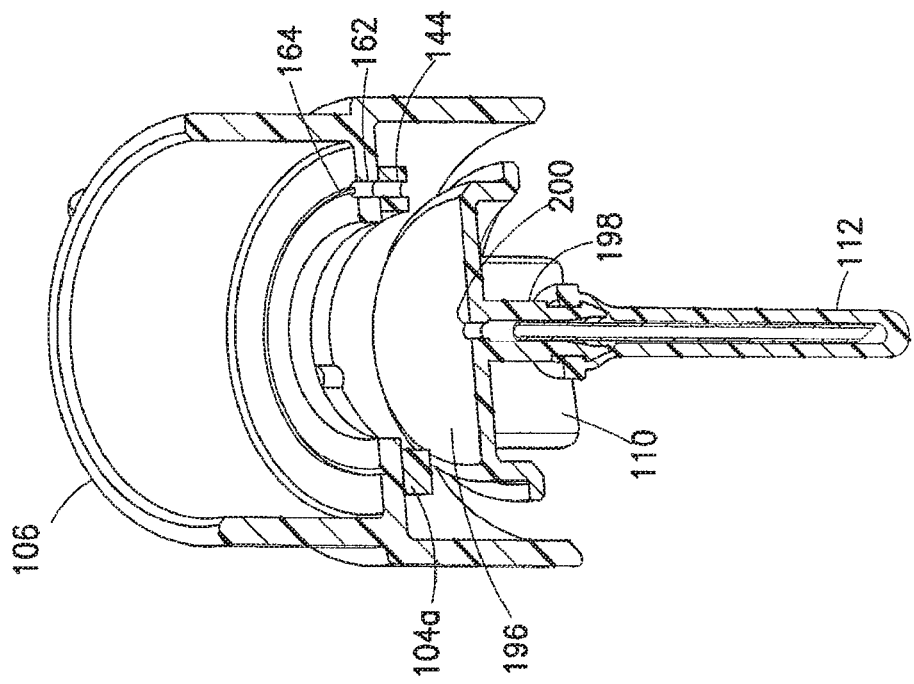
FIG. 12E is another assembled, cross-sectional perspective view of the flow regulator system of FIG. 12A in the maximum flow position with the spine and the tube holder removed in accordance with an embodiment of the present invention.
Figure 12D:
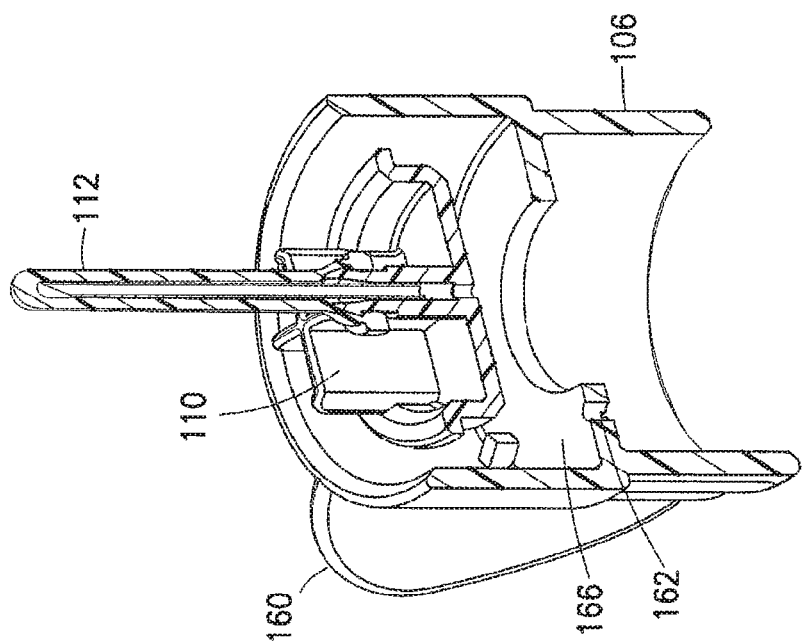
FIG. 12D is an assembled, cross-sectional perspective view of the flow regulator system of FIG. 12A in the maximum flow position with the spine and the tube holder removed in accordance with an embodiment of the present invention.
Figure 13A:
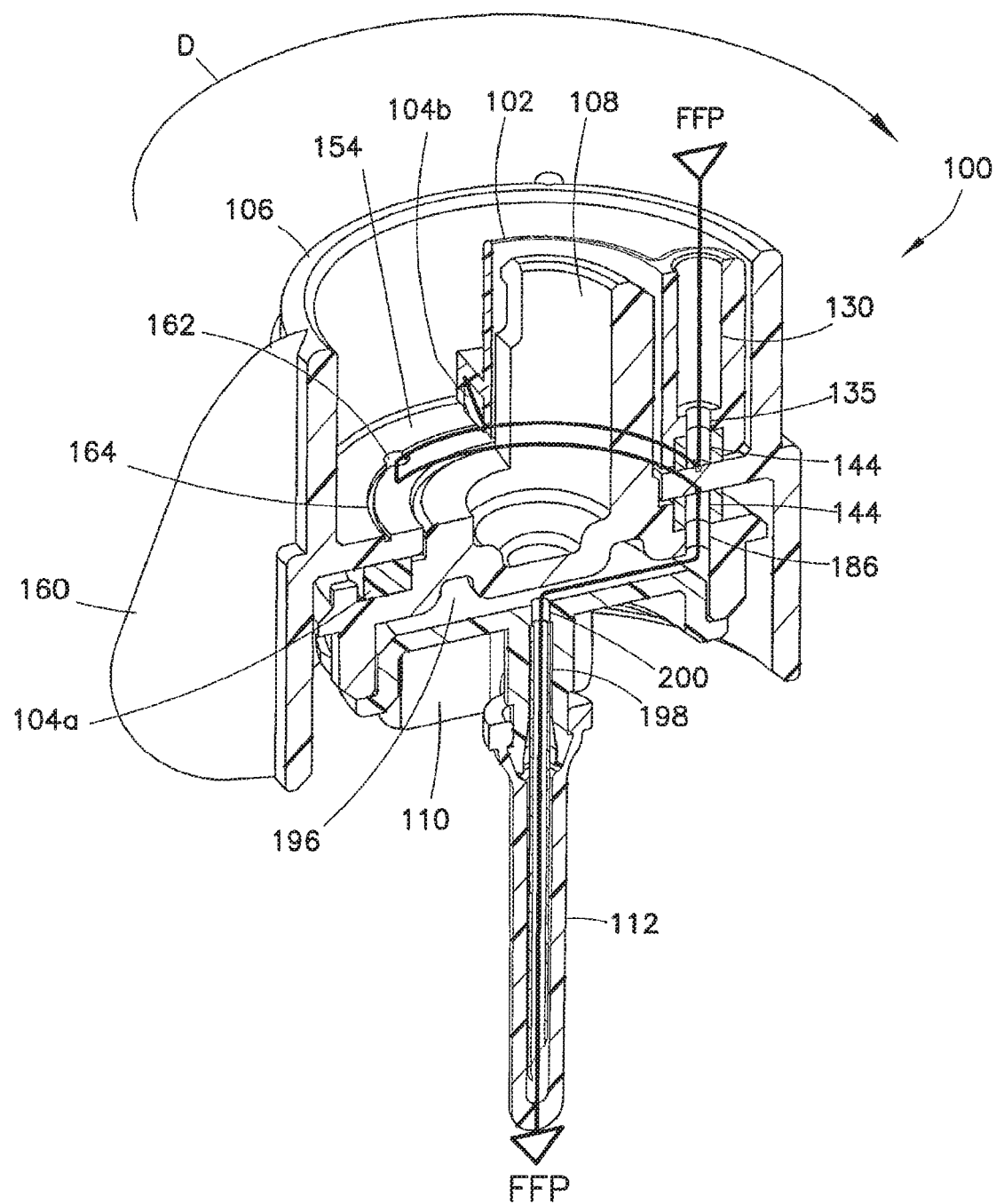
FIG. 13A is an assembled, cross-sectional perspective view of the flow regulator system of FIG. 2 in a minimum flow position in accordance with an embodiment of the present invention.
Figure 13C:
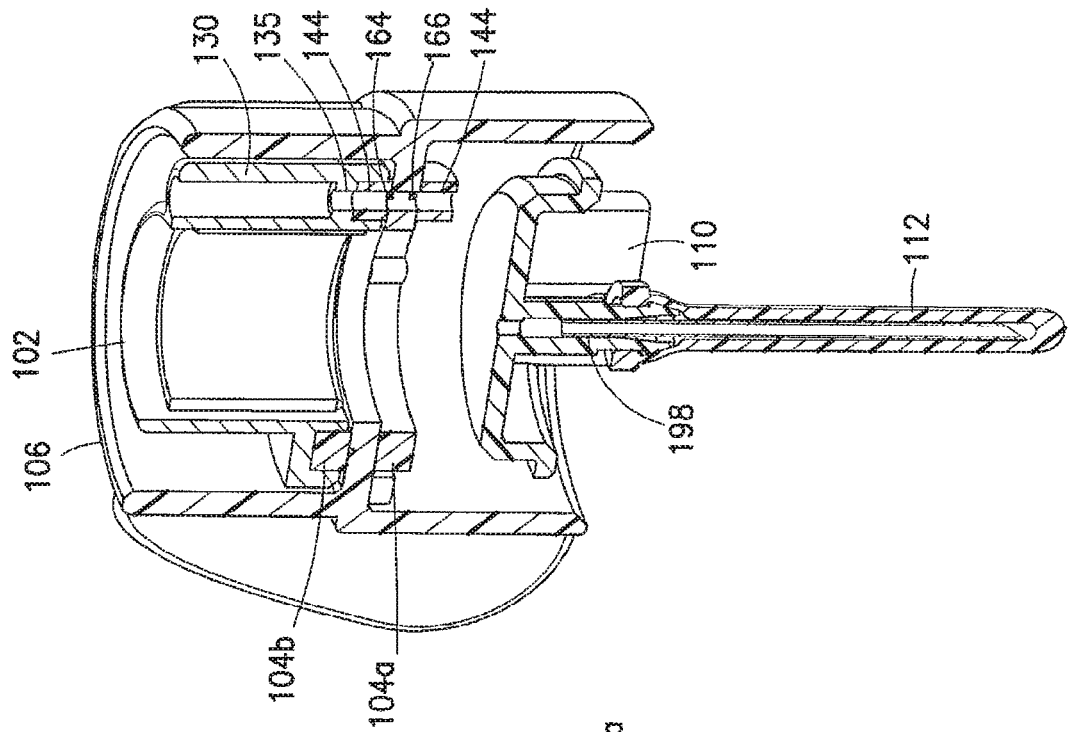
FIG. 13C is another assembled, cross-sectional perspective view of the flow regulator system of FIG. 13A in the minimum flow position with the spine removed in accordance with an embodiment of the present invention.
Figure 13B:
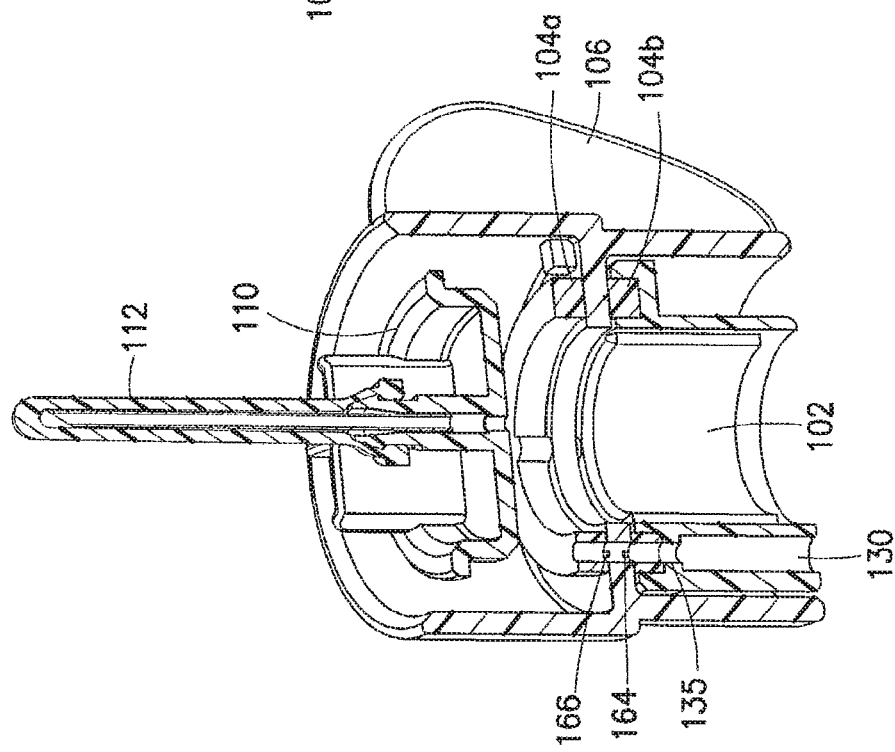
FIG. 13B is an assembled, cross-sectional perspective view of the flow regulator system of FIG. 13A in the minimum flow position with the spine removed in accordance with an embodiment of the present invention.
Figure 13E:
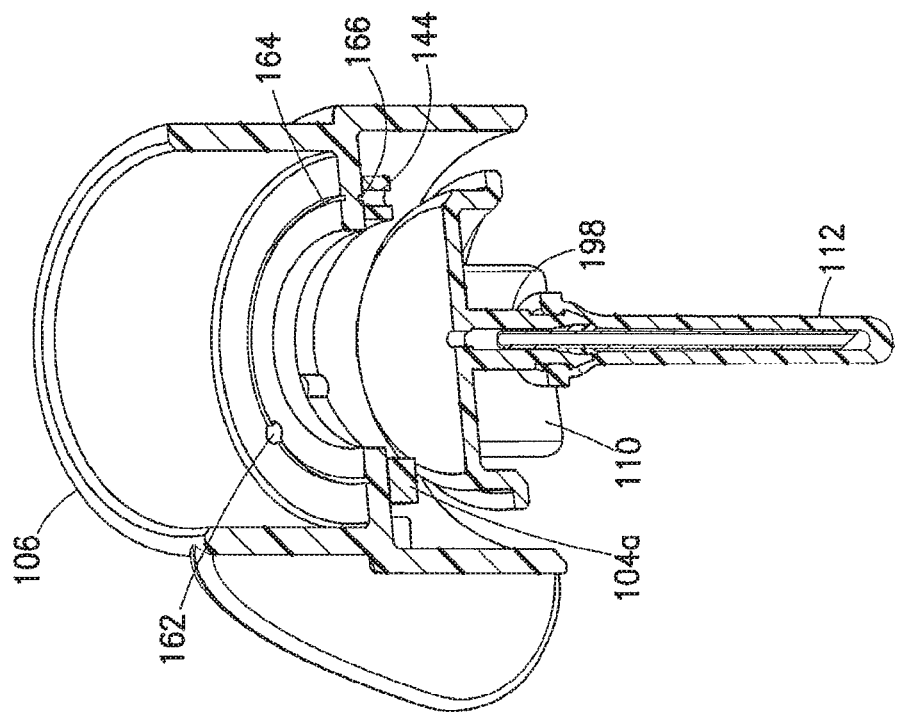
FIG. 13E is another assembled, cross-sectional perspective view of the flow regulator system of FIG. 13A in the minimum flow position with the spine and the tube holder removed in accordance with an embodiment of the present invention.
Figure 13D:
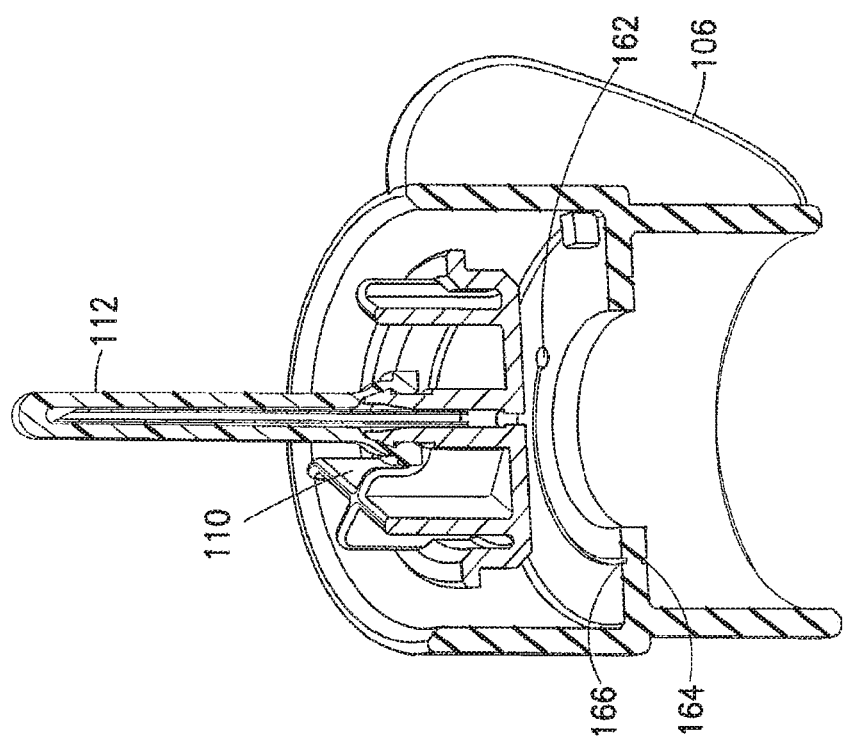
FIG. 13D is an assembled, cross-sectional perspective view of the flow regulator system of FIG. 13A in the minimum flow position with the spine and the tube holder removed in accordance with an embodiment of the present invention.

Referring to FIG. 12A, the fluid flow path FFP of a fluid, such as blood, through flow regulator system 100 with system 100 in the maximum flow position will now be described. If the device is provided in the maximum flow position as shown in FIG. 12A, blood flows along the fluid flow path FFP from the vein of a patient to flow channel 130 of tube holder sub-assembly 102. With system 100 in the maximum flow position (FIG. 12A) as described above, the blood then flows through flow channel 130 of tube holder sub-assembly 102 and out second opening 135 (FIGS. 5E and 12A) of flow channel 130 to gasket flow aperture 144 of a first gasket 104b. The blood then flows directly through flow aperture 162 of dial 106 and gasket flow aperture 144 of a second gasket 104a to flow aperture 186 of spine 108 as shown by fluid flow path FFP in FIG. 12A. The blood will then flow between spine 108 and hub 110 along a bottom surface of spine connection portion 196 of hub 110 and through flow entrance aperture 200 (FIG. 9D) to flow collection channel 198 of hub 110 as shown in FIG. 12A. The blood may then travel through flow collection channel 198 of hub 110 to the lumen of needle 112 for collection in an evacuated tube secured to needle 112 as described above. In one embodiment, the bottom surface of spine connection portion 196 of hub 110 may include a concave surface or may be curved inward to facilitate the flow of blood through flow entrance aperture 200 to flow collection channel 198 of hub 110.

In this manner, an effective flow distance that the blood travels is minimized, the flow of the blood is not impeded, and the flow rate of the blood is maximized. Accordingly, in the position shown in FIG. 12A, system 100 is in a maximum flow position. Referring to FIG. 13A, with system 100 in a minimum or reduced flow position, an effective flow distance that the blood travels is increased to impede the flow of the blood and reduce the flow rate of the blood as will be described below. The configuration of flow aperture 162 of dial 106 allows for the effective length of the fluid flow path FFP of the regulator (as shown in FIGS. 12A and 13A) to be manually varied to modulate the flow of blood coming from the vein of a patient and through system 100.

During blood collection, system 100 allows a medical clinician to manually vary the flow of blood from the vein of a patient and through system 100 based on the condition of the patient. For example, the medical clinician is part of the feedback loop and it is the medical clinician's judgment to determine an appropriate flow rate from a particular patient. The medical clinician would be able to set a position of dial 106 prior to blood collection and would then have the ability to manually adjust dial 106 to manipulate or vary the flow rate during blood collection. For example, referring to FIGS. 12A and 13A, with flow regulator system 100 in a maximum flow position (FIG. 12A), the medical clinician may determine that the flow rate should be reduced. Accordingly, the clinician may rotate dial 106 in a direction generally along arrow C to the position shown in FIG. 13A. In this manner, the flow rate may be reduced as will now be described. Rotation of dial 106 to the position shown in FIG. 13A causes flow aperture 162 of dial 106 to move out of alignment with flow channel 130 of tube holder sub-assembly 102 and flow aperture 186 of spine 108 as shown in FIG. 13A. In this manner, an effective flow distance that the blood travels is increased and the flow of blood is impeded. Accordingly, the flow rate of the blood is reduced.

With system 100 in a minimum flow position as shown in FIG. 13A, flow aperture 162 of dial 106 is not in alignment with flow channel 130 of tube holder sub-assembly 102 and flow aperture 186 of spine 108. The fluid flow path FFP of a fluid, such as blood, through flow regulator system 100 with system 100 in the minimum flow position will now be described. With the device in the minimum flow position as shown in FIG. 13A, blood flows along the fluid flow path FFP from the vein of a patient to flow channel 130 of tube holder sub-assembly 102. With system 100 in the minimum flow position (FIG. 13A) as described above, the blood then flows through flow channel 130 of tube holder sub-assembly 102 and out second opening 135 (FIGS. 5E and 13A) of flow channel 130 to gasket flow aperture 144 of a first gasket 104b. The blood then flows through gasket flow aperture 144 of the first gasket 104b to a portion of front flow channel 164 (FIG. 7A) of dial 106. Front flow channel 164 provides a flow channel for the blood to travel along. The only passage that allows the blood to flow through center plate 154 of dial 106 to spine 108 is flow aperture 162 of dial 106. Because flow aperture 162 of dial 106 is not in alignment with flow channel 130 of tube holder sub-assembly 102 in the minimum flow position, the blood must flow along front flow channel 164 as shown in FIG. 13A to flow aperture 162 of dial 106. In this manner, the effective length of the fluid flow path FFP of the regulator is increased and the flow rate of the blood through flow regulator system 100 is reduced. The greater the distance that the blood must travel along front flow channel 164 of dial 106 to reach flow aperture 162, the greater the reduction of the flow rate of the blood through flow regulator system 100.

Once the blood travels to flow aperture 162, the blood is then able to flow through flow aperture 162 of dial 106 and to back flow channel 166 (FIG. 7B) of dial 106. Because flow aperture 162 of dial 106 is not in alignment with flow aperture 186 of spine 108 in the minimum flow position, the blood must flow along back flow channel 166 (FIG. 7B) of dial 106 as shown in FIG. 13A to reach flow aperture 186 of spine 108. In this manner, the effective length of the fluid flow path FFP of the regulator is increased and the flow rate of the blood through flow regulator system 100 is reduced. The greater the distance that the blood must travel along back flow channel 166 of dial 106 to reach flow aperture 186 of spine 108, the greater the reduction of the flow rate of the blood through flow regulator system 100. Once the blood travels to flow aperture 186 of spine 108, the blood flows from back flow channel 166 of dial 106 through gasket flow aperture 144 of a second gasket 104a to flow aperture 186 of spine 108 as shown in FIG. 13A. The blood will then flow between spine 108 and hub 110 along a bottom surface of spine connection portion 196 of hub 110 and through flow entrance aperture 200 (FIG. 9D) to flow collection channel 198 of hub 110 as shown in FIG. 13A. The blood may then travel through flow collection channel 198 of hub 110 to the lumen of needle 112 for collection in an evacuated tube secured to needle 112 as described above. In one embodiment, the bottom surface of spine connection portion 196 of hub 110 may include a concave surface or may be curved inward to facilitate the flow of blood through flow entrance aperture 200 to flow collection channel 198 of hub 110.

In this manner, an effective flow distance that the blood travels is increased, the flow of the blood is impeded, and the flow rate of the blood is reduced. Accordingly, in the position shown in FIG. 13A, system 100 is in a minimum or reduced flow position.

As described above, during blood collection, system 100 allows a medical clinician to manually vary the flow of blood from the vein of a patient and through system 100 based on the condition of the patient. For example, the medical clinician may determine that the flow rate should be shut off. Accordingly, the clinician may rotate dial 106 in a direction generally along arrow C (FIG. 12A) to a shut off position. In the shut off position, no portion of back flow channel 166 of dial 106 is in alignment with aperture 186 of spine 108. In this manner, the blood is not able to reach aperture 186 of spine 108 and thus the flow of blood is prevented from flowing to spine 108.

As described above, during blood collection, system 100 allows a medical clinician to manually vary the flow of blood from the vein of a patient and through system 100 based on the condition of the patient. For example, from a shut off position or the minimum flow position of FIG. 13A, the medical clinician may determine that the flow rate should be turned back on or that the flow rate should be increased. Accordingly, referring to FIG. 13A, the clinician may rotate dial 106 in a direction generally along arrow D to increase the flow rate in the manner as described above.

In this manner, system 100 allows the clinician to rotate dial 106 in the direction generally along either arrow C (FIG. 12A) or arrow D (FIG. 13A) to incrementally or linearly move system 100 from the position shown in FIG. 12A to the position shown in FIG. 13A and to all positions in between, or to a shut off position if desired. Dial 106 of system 100 allows for precise, incremental, or linear control of the flow rate of a fluid through system 100.

In one procedure, initially a medical clinician will set a position of dial 106 so that flow regulator system 100 is in a reduced flow position with an effective flow distance that the blood travels is increased so that the flow rate of the blood is reduced to counteract the strong vacuum effect upon initial access of the evacuated tube. The medical clinician may then decrease the effective flow distance that the blood travels through flow regulator system 100, i.e., the medical clinician may increase the flow rate of the blood through flow regulator system 100, to allow better flow once initial draw is equalized.

FIGS. 14-20B illustrate another exemplary embodiment of the present invention directed to a manual blood flow regulation device which regulates the flow of blood from the vein of a patient by manually varying the cross-sectional area of an orifice of the regulation device. Referring to FIGS. 14-20B, a flow regulator system 300 includes a flow control dial 302, a flow control insert 304, a housing 306, and an optional label or plate 308 with indicia.

Figure 15C:
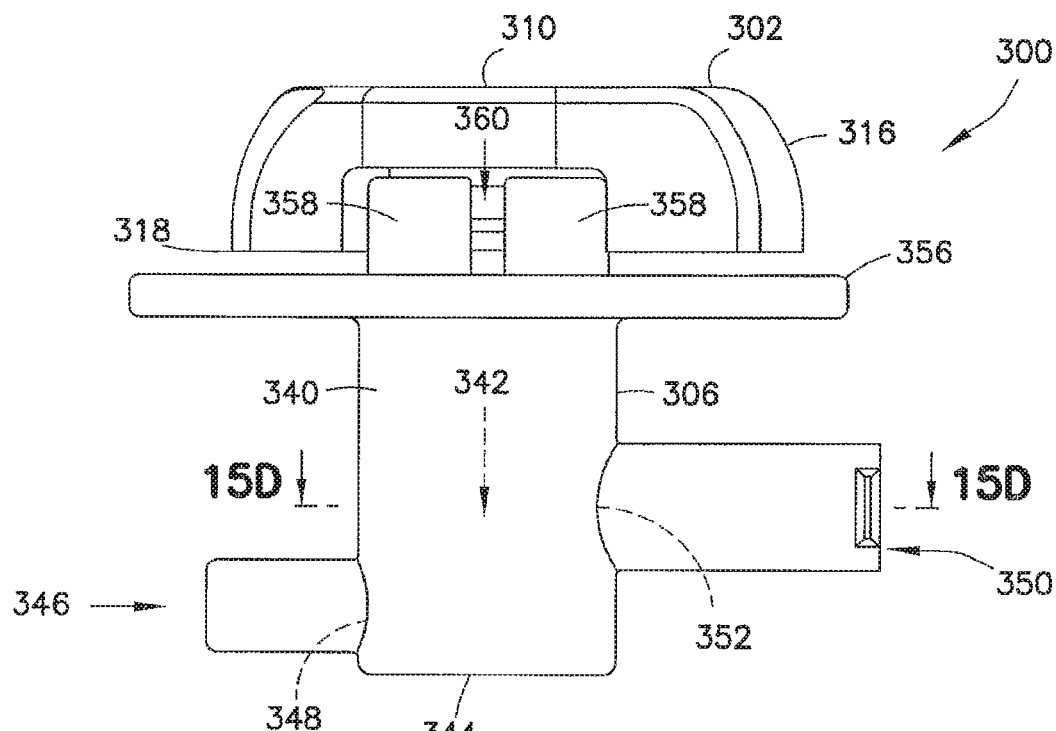
FIG. 15C is an assembled, side elevation view of the flow regulator system of FIG. 14 in accordance with an embodiment of the present invention.

Referring to FIGS. 14, 15A, 15B, and 15C, flow control dial 302 includes a head portion 310, a body portion 312, and an annular groove 314 defined therebetween. Head portion 310 of flow control dial 302 includes at one of the radial ends a finger flange 316 and at the other radial end a point portion 318. Point portion 318 can be tapered to a point to form a pointer or indicator for pointing to a graduated scale disposed on a portion of system 300 or otherwise provided on the plate 308 to indicate the flow rate of a fluid through flow regulator system 300. Referring to FIGS. 15A and 15B, body portion 312 of flow control dial 302 includes a flow control portion 320 which defines an open flow recess 322 and includes a helical profile or tapered groove 324 which extends from a maximum width portion 329 (FIGS. 15A and 18B) to a minimum width portion 331 (FIGS. 15B and 18B) and terminates in an aperture blocking portion 326. Flow control portion 320 also defines a cavity 325 at a bottom end thereof which includes a protruding member 327 for securement to flow control insert 304 as will be described in detail later. Flow control portion 320 provides a means for manually varying the open cross-sectional area of a flow orifice 352 of housing 306 as will be described in more detail below. In one embodiment, open flow recess 322 of flow control dial 302 is sized relative to flow orifice 352 of housing 306 so that with open flow recess 322 in alignment with flow orifice 352 of housing 306, no portion of flow orifice 352 is covered or blocked by flow control portion 320 of flow control dial 302.

Figure 15D:
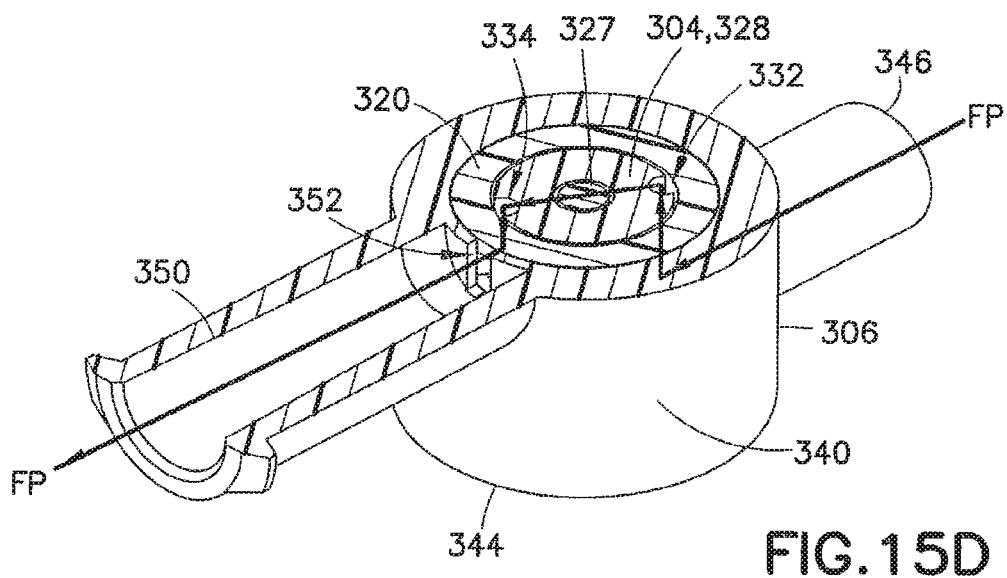
FIG. 15D is a cross-sectional perspective view taken along line 15D-15D of FIG. 15C in accordance with an embodiment of the present invention.

Referring to FIGS. 14 and 15D, flow control insert 304 includes a body 328, an annular protrusion 330 extending around a periphery of body 328, an inlet fluid channel 332 defined at a first end of body 328 and an opposing outlet fluid channel 334 defined at an opposite end of body 328, and a center bore 336 defined in body 328 at a top end. In one embodiment, inlet fluid channel 332 is disposed one-hundred eighty (180) degrees from outlet fluid channel 334. In other embodiments, inlet fluid channel 332 may be disposed any number of degrees from outlet fluid channel 334. Fluid channels 332, 334 of flow control insert 304 define a part of flow path FP (FIGS. 15D, 17B, 18B, 19B, and 20B) as will be described in more detail below. Center bore 336 of flow control insert 304 is sized to accept protruding member 327 of flow control dial 302 such that a fluid, e.g., blood, can flow from an inlet duct 346 to an outlet duct 350 of housing 306 via flow control dial 302 and flow control insert 304 as will be described in more detail below.

Referring to FIGS. 14, 15C, 15D and 17B, housing 306 includes a continuous exterior sidewall 340 which defines an interior cavity 342 therein. Inlet duct 346 and outlet duct 350 extend from respective opposing ends of sidewall 340 of housing 306 and are in fluid communication to one another via interior cavity 342 of housing 306. Inlet duct 346 is in fluid communication with interior cavity 342 of housing 306 via an inlet port 348. Additionally, outlet duct 350 is in fluid communication with interior cavity 342 of housing 306 via outlet port or flow orifice 352. In one embodiment, outlet duct 350 is in fluid communication with interior cavity 342 of housing 306 via flow orifice 352 and a slot 360. Slot 360 is located below flow orifice 352 and is disposed within the interior surface of a portion of sidewall 340 of housing 306. At an upper end of housing 306, an upper plate 354 extends from sidewall 340 around a periphery of sidewall 340. Upper plate 354 includes a lip 356 thereby forming a receiving portion to receive label 308 which may contain indicia to indicate a graduated scale indicating the flow rate of a fluid through flow regulator system 300 as will be described in more detail below. The uppermost portion of housing 306 further includes a plurality of upper walls 358 having slots 360 defined between adjacent upper walls 358. The plurality of upper walls 358 together define a center bore 362. An annular protrusion 364 extends from the interior surface of upper walls 358 and into bore 362.

Flow control insert 304 may be inserted into center bore 362 of housing 306. The outside diameter or annular protrusion 330 of flow control insert 304 is sized relative to the interior surface of sidewall 340 of housing 306 so that flow control insert 304 is secured within housing 306 by a sliding fit. In one embodiment, a lubricant may be disposed between flow control insert 304 and the interior surface of sidewall 340 of housing 306 to create a fluid seal between flow control insert 304 and housing 306. Upper walls 358 of housing 306 include slots 360 respectively therebetween to allow the upper portion of housing 306 to slightly deform so that flow control insert 304 can be inserted within housing 306 as shown in FIGS. 15C-20B. Next, flow control dial 302 can be inserted within center bore 362 of housing 306 such that protruding member 327 is received within center bore 336 of flow control insert 304 as shown in FIG. 17B. The engagement between protruding member 327 of flow control dial 302 within center bore 336 of flow control insert 304 allows flow control dial 302 to be rotatable relative to flow control insert 304 and housing 306, and also allows a fluid, such as blood, to flow between flow control dial 302 and flow control insert 304 as will be described in more detail below.

As described above with respect to flow control insert 304 and housing 306, upper walls 358 of housing 306 include slots 360 respectively therebetween to allow the upper portion of housing 306 to slightly deform so that flow control dial 302 can be inserted within housing 306. Referring to FIGS. 14, 15A, and 17B, flow control dial 302 is inserted in housing 306 such that body portion 312 of flow control dial 302 is located past annular protrusion 364 of upper walls 358 of housing 306 and annular protrusion 364 of housing 306 occupies annular groove 314 of flow control dial 302 as shown in FIG. 17B. In this manner, flow control dial 302 is secured within housing 306, i.e., flow control dial 302 cannot be unintentionally displaced from housing 306, and flow control dial 302 may be rotatable relative to housing 306 and flow control insert 304, as will be described below.

Referring to FIGS. 14-20B, the use of flow regulator system 300 to adjustably alter a flow path will now be described. Flow regulator system 300 is capable of acting to slow down the initial flow rate of blood into an evacuated blood collection device as a result of the application of a strong vacuum pressure from the evacuated blood collection device on the patient's accessed vasculature. The flow regulator system 300 is responsive to the initial spike in vacuum pressure from the evacuated blood collection device and slows down the draw of blood in order to avoid rapid depletion of blood from the patient to prevent the collapse of the patient's blood vessel during blood collection. In the embodiment shown in FIGS. 14-20B, the flow of blood coming from the vein of a patient is modulated by manually varying the effective cross-sectional area of an orifice of the regulation device, e.g., flow orifice 352 of housing 306.

Figure 16:
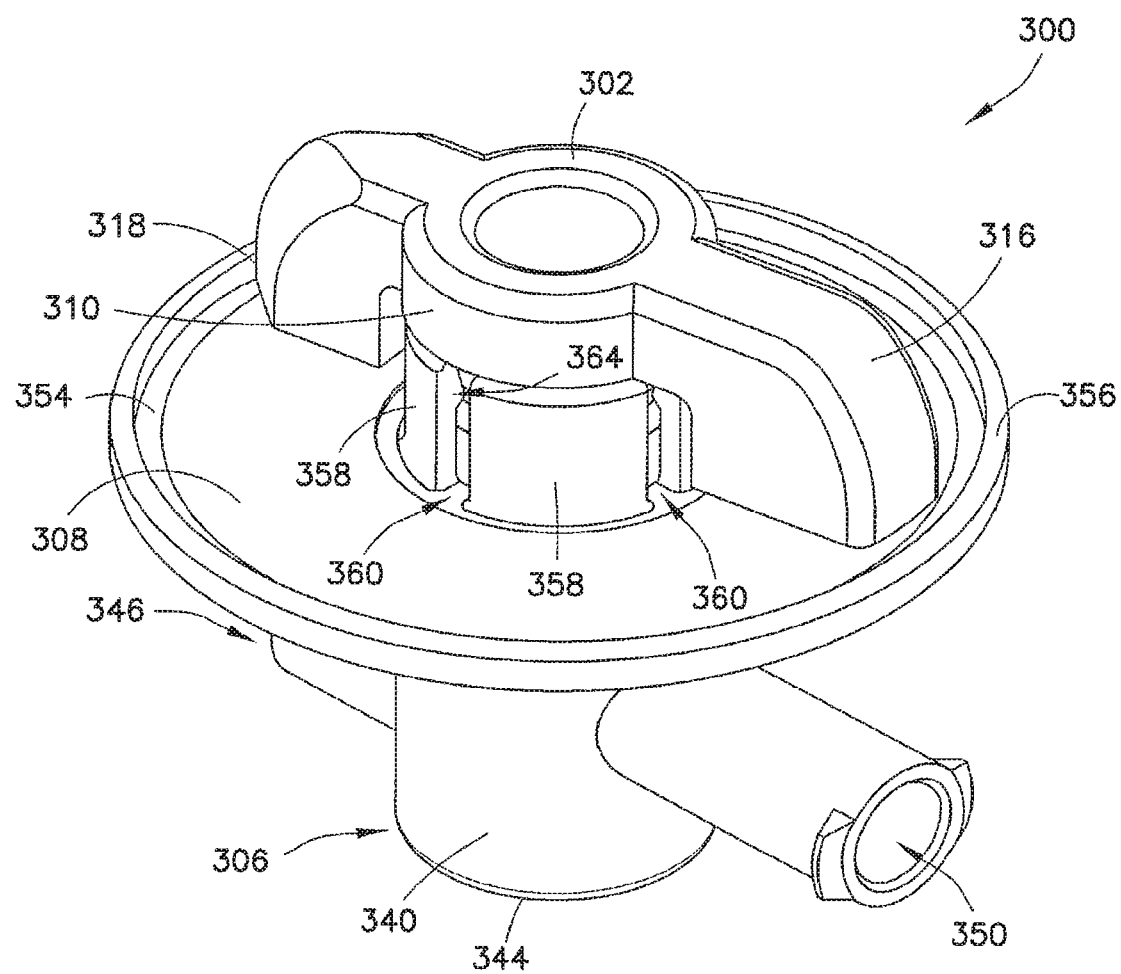
FIG. 16 is an assembled, perspective view of the flow regulator system of FIG. 14 in accordance with an embodiment of the present invention.
Figure 17A:
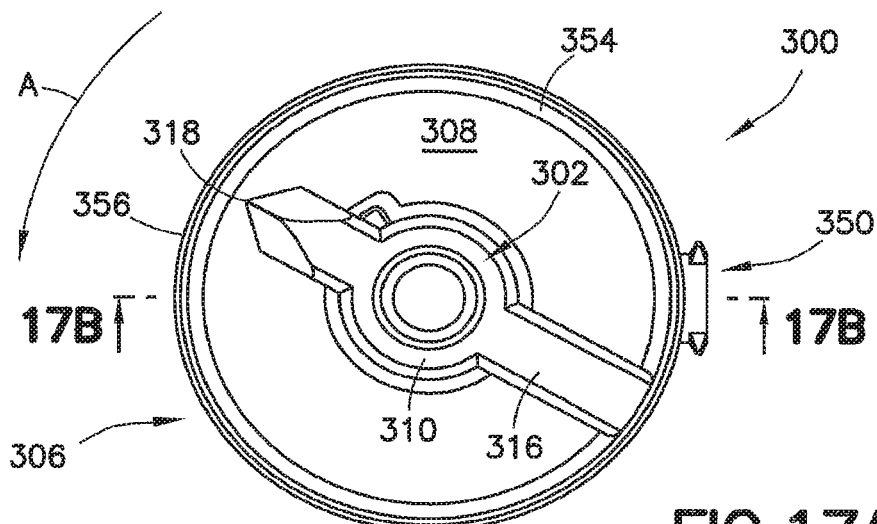
FIG. 17A is a plan view of the flow regulator system of FIG. 16 in a maximum flow or fully open position in accordance with an embodiment of the present invention.
Figure 17B:
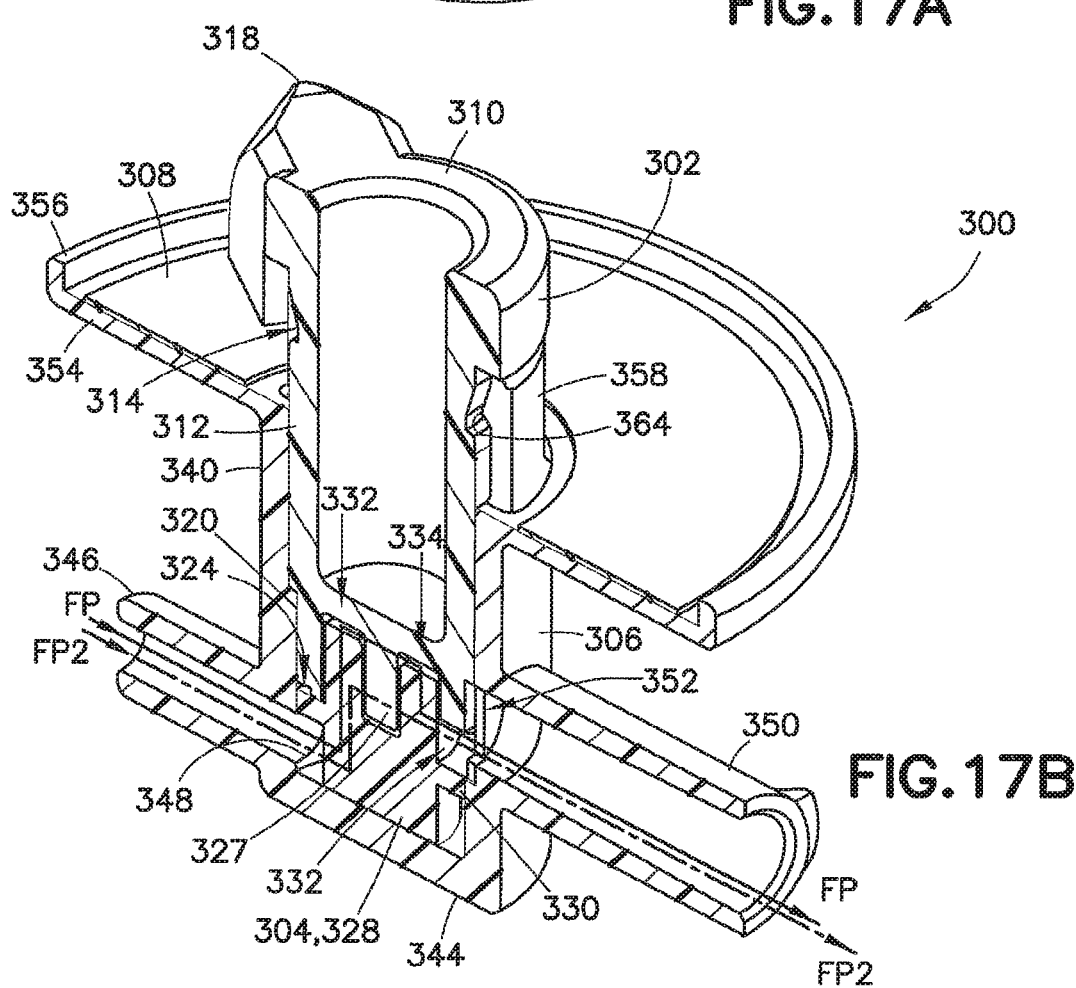
FIG. 17B is a cross-sectional perspective view taken along line 17B-17B of FIG. 17A in accordance with an embodiment of the present invention.
Figure 20A:
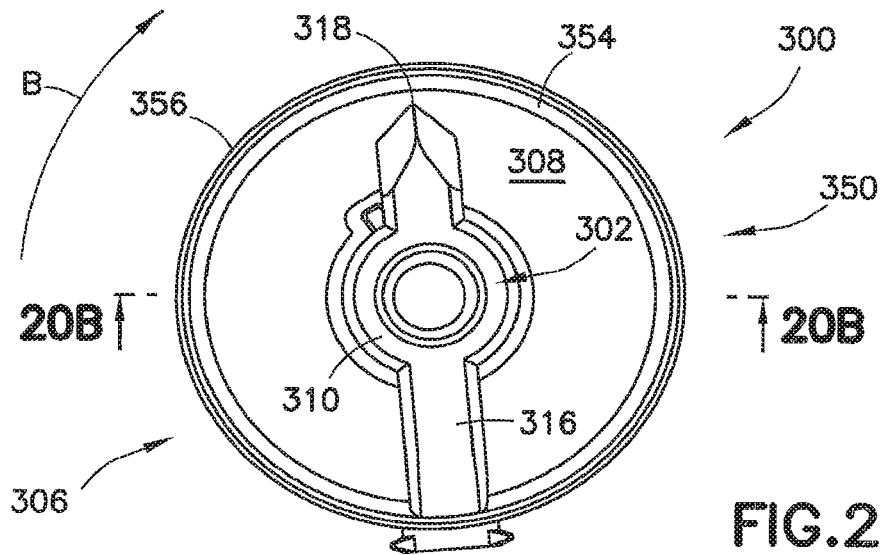
FIG. 20A is a plan view of the flow regulator system of FIG. 16 in a no flow or fully closed position in accordance with an embodiment of the present invention.

Referring to FIGS. 16-17B, flow regulator system 300 is shown in a maximum flow or fully open position. In this position, flow recess 322 (FIG. 15A) of flow control dial 302 is aligned with flow orifice 352 (FIG. 15D) of housing 306 as shown in FIG. 17B. Referring to FIG. 17A, in one embodiment, plate 308 includes a scale of indicia thereon to indicate to a user the flow rate of a fluid flowing through flow regulator system 300. For example, label 308 may include indicia indicating the flow rate of a fluid through system 300 in milliliters per hour (mL/hr). Point portion 318 of flow control dial 302 may be tapered to form a point so that point portion 318 points to particular indicia on label 308 to indicate a current flow rate through system 300. Referring to FIGS. 15A, 17A, and 17B, in one embodiment, point portion 318 is configured relative to open flow recess 322 of flow control dial 302 so that with flow recess 322 of flow control dial 302 aligned with flow orifice 352 of housing 306, point portion 318 of flow control dial 302 is indicated at a first position (FIG. 17A) and system 300 is in a maximum flow position. In such an embodiment, point portion 318 of flow control dial 302 points to indicia that indicates system 300 is at a maximum flow position. Referring to FIG. 20A, in such an embodiment, point portion 318 is also configured relative to aperture blocking portion 326 (FIG. 15A) of flow control dial 302 so that with aperture blocking portion 326 of flow control dial 302 aligned with flow orifice 352 (FIGS. 15C and 15D) of housing 306, point portion 318 of flow control dial 302 is indicated at a second position (FIG. 20A) and system 300 is in a fully closed or reduced flow position. In such an embodiment, point portion 318 of flow control dial 302 points to indicia that indicates system 300 is at a reduced flow or off position.

In one embodiment, flow regulator system 300 (FIG. 16) may be used with blood collection device 10 (FIG. 1). For example, flow regulator system 300 may be positioned between distal end 70 (FIG. 1) and proximal end 72 (FIG. 1) of tubing 68 to regulate the flow rate of the blood between the blood vessel of the patient and the evacuated tube. In one embodiment, flexible plastic tubing, such as tubing 68 shown in FIG. 1, may be secured to inlet duct 346 and outlet duct 350 of housing 306, respectively, so that the tubing secured to inlet duct 346 and the tubing secured to outlet duct 350 are in fluid communication together via system 300. The other end of the tubing secured to inlet duct 346 may be securable to a needle assembly which can be inserted in the vein of a patient for blood collection. Additionally, the other end of the tubing secured to outlet duct 350 may be securable to a tube holder and an evacuated tube for a phlebotomy procedure. In this manner, a medical clinician or patient can perform a blood collection procedure in a standard manner using system 300 to modulate the flow of blood coming from the vein of a patient by manually varying the cross-sectional area of flow orifice 352 of housing 306.

Referring to FIG. 17B, the flow path FP of a fluid, such as blood, through flow regulator system 300 with system 300 in a maximum flow or fully open position will now be described. If the device is provided in the maximum flow position as shown in FIG. 17B, blood flows along the flow path FP from the vein of a patient to inlet duct 346 of housing 306. The blood may then travel through inlet duct 346 and past inlet port 348 into interior cavity 342 (FIG. 15C) of housing 306 adjacent the bottom portion of body 328 of flow control insert 304. The blood may then travel up flow control insert 304 by flowing within inlet fluid channel 332 of insert 304 and past annular protrusion 330 of insert 304. The blood may then travel within the gap between the top surface of body 328 of flow control insert 304 and the top surface of cavity 325 (FIG. 15A) of flow control dial 302. The blood may then travel down flow control insert 304 by flowing within outlet fluid channel 334 of insert 304. As the blood travels down flow control insert 304 by flowing within outlet fluid channel 334 of insert 304, the blood may also flow along annular protrusion 330 of insert 304 within the track of tapered groove 324 of flow control dial 302 and then the blood may travel through open flow recess 322 of flow control dial 302 and out flow orifice 352 of housing 306.

Additionally, with the device provided in the position shown in FIG. 17B, blood may flow along a second flow path FP2. The flow path that the blood may take through flow regulator system 300 depends on the rotational position of flow control insert 304 relative to housing 306. Blood may flow along flow path FP2 from the vein of a patient through inlet duct 346 and past inlet port 348 into interior cavity 342 of housing 306 adjacent the bottom portion of body 328 of flow control insert 304. The blood may then travel up flow control insert 304 by flowing within inlet fluid channel 332 of insert 304 and past annular protrusion 330 of insert 304. The blood may then travel along annular protrusion 330 of insert 304, within the track of tapered groove 324 of flow control dial 302, and then the blood may travel through open flow recess 322 of flow control dial 302 and out flow orifice 352 of housing 306.

Once the blood has traveled through flow orifice 352, the blood travels through outlet duct 350 and to the tubing secured to outlet duct 350 and to an evacuated tube, for example, for collection. With flow recess 322 of dial 302 aligned with flow orifice 352 of housing 306, the blood is allowed to flow through flow orifice 352. In the maximum flow position, in one embodiment, the entirety of flow recess 322 is aligned with flow orifice 352 and thus the greatest cross-sectional area of flow orifice 352 is available to allow blood to flow past. As will be described below, the configuration of flow recess 322, tapered groove 324, and blocking portion 326 (FIG. 15A) of flow control dial 302 allows for the cross-sectional area of flow orifice 352 to be manually varied to modulate the flow of blood coming from the vein of a patient and through system 300.

Figure 18A:
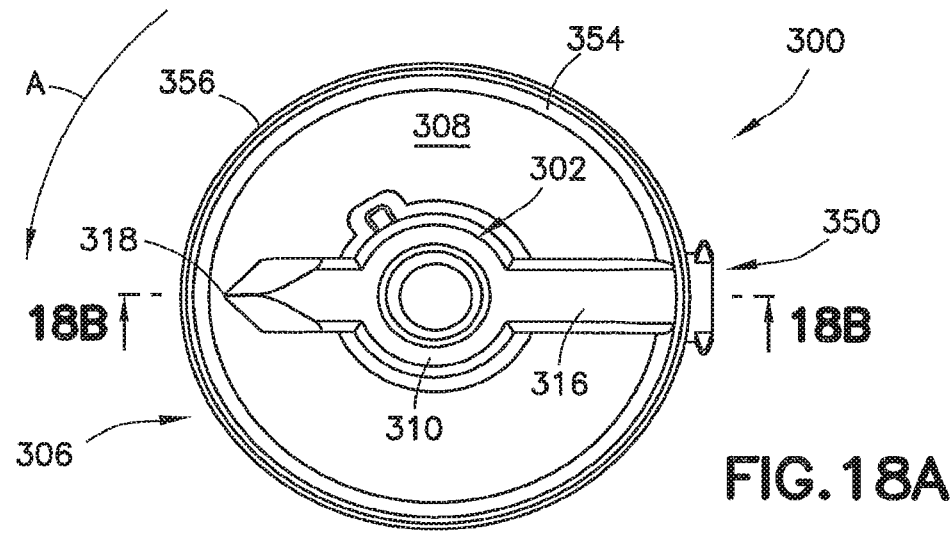
FIG. 18A is a plan view of the flow regulator system of FIG. 16 in a first flow or first partially open position in accordance with an embodiment of the present invention.
Figure 18B:
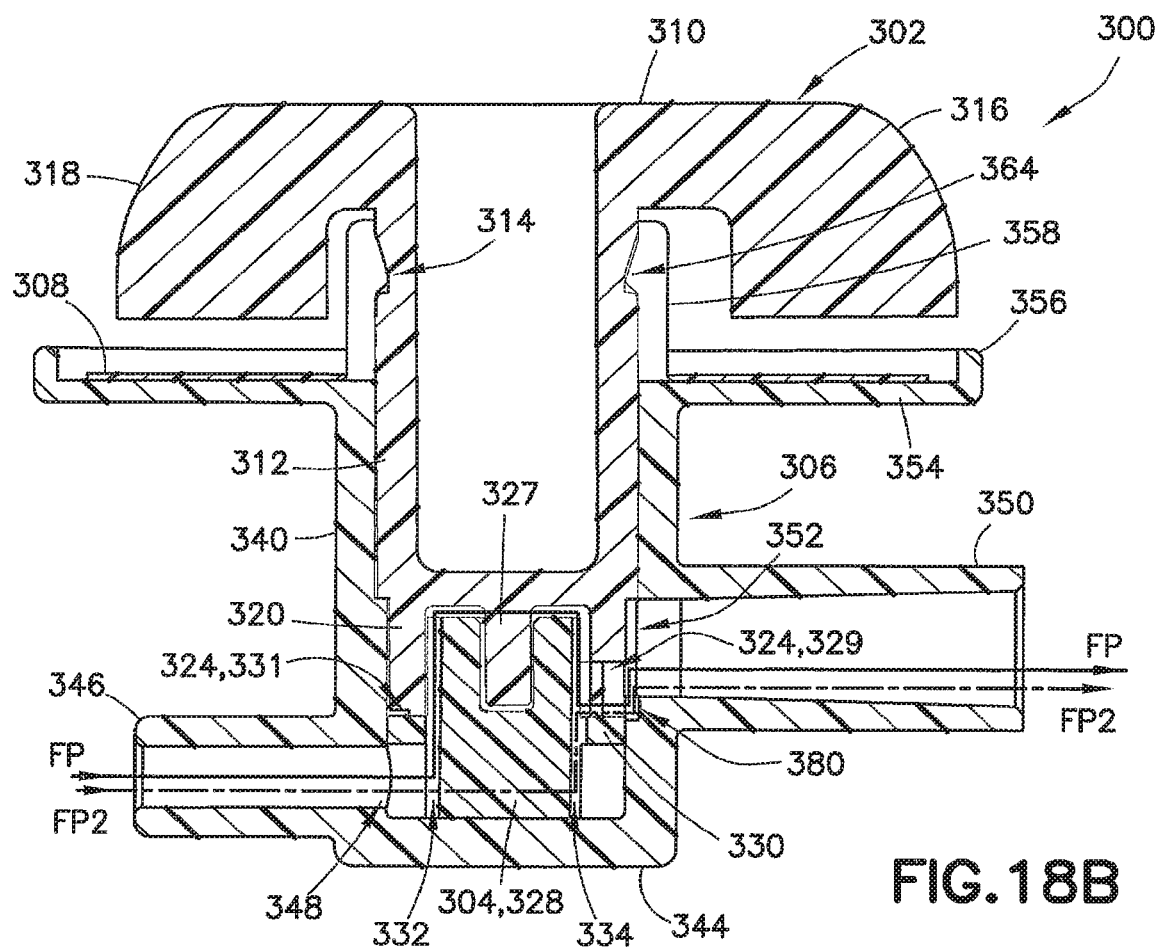
FIG. 18B is a cross-sectional view taken along line 18B-18B of FIG. 18A in accordance with an embodiment of the present invention.

During blood collection, system 300 allows a medical clinician to manually vary the flow of blood from the vein of a patient and through system 300 based on the condition of the patient. For example, the medical clinician is part of the feedback loop and it is the medical clinician's judgment to determine an appropriate flow rate from a particular patient. The medical clinician would be able to set the flow control dial 302 of system 300 prior to blood collection and would then have the ability to manually adjust flow control dial 302 to manipulate or vary the flow rate during blood collection. For example, referring to FIG. 17A with flow regulator system 300 in a maximum flow position, the medical clinician may determine that the flow rate should be reduced. Accordingly, the clinician may rotate flow control dial 302 in a direction generally along arrow A to the position shown in FIGS. 18A and 18B. In this manner, the flow rate is reduced as will now be described. Rotation of flow control dial 302 to the position shown in FIGS. 18A and 18B causes open flow recess 322 (FIG. 15A) of flow control dial 302 to rotate in the direction generally along arrow A so that open flow recess 322 is no longer in alignment with flow orifice 352 of housing 306. In the position of FIGS. 18A and 18B, the portion of tapered groove 324 adjacent open flow recess 322 of flow control dial 302, i.e., maximum width portion 329 (FIG. 15A) of tapered groove 324, is aligned with flow orifice 352 of housing 306 as shown in FIG. 18B.

Referring to FIG. 18B, the flow path FP of a fluid, such as blood, through flow regulator system 300 with system 300 in the partially open flow position shown in FIGS. 18A and 18B will now be described. In the flow position as shown in FIGS. 18A and 18B, as the medical clinician or patient performs blood collection, blood flows along the flow path FP from the vein of a patient through the tubing secured to inlet duct 346 and to inlet duct 346 of housing 306. Next, as described above, the blood travels through inlet duct 346 and past inlet port 348 into interior cavity 342 (FIG. 15C) of housing 306 adjacent the bottom portion of body 328 of flow control insert 304. Next, as described above, the blood travels up flow control insert 304 by flowing within inlet fluid channel 332 of insert 304 and past annular protrusion 330 of insert 304. Next, as described above, the blood travels within the gap between the top surface of body 328 of flow control insert 304 and the top surface of cavity 325 (FIG. 15A) of flow control dial 302. Next, as described above, the blood travels down flow control insert 304 by flowing within outlet fluid channel 334 of insert 304. As the blood travels down flow control insert 304 by flowing within outlet fluid channel 334 of insert 304, the blood may also flow along annular protrusion 330 of insert 304 within the track of tapered groove 324 of flow control dial 302 and then the blood may be forced through slot 360 of housing 306. In this manner, the blood is forced to step through slot 360 before flowing out flow orifice 352 of housing 306. In one embodiment, the effective cross-sectional area of slot 360 is determined by slot 360 and the helical shoulder of flow control dial 302. As described above, once the blood has traveled through flow orifice 352, the blood travels through outlet duct 350 and to the tubing secured to outlet duct 350 and to an evacuated tube, for example, for collection.

Additionally, with the device provided in the position shown in FIG. 18B, blood may flow along a second flow path FP2. The flow path that the blood may take through flow regulator system 300 depends on the rotational position of flow control insert 304 relative to housing 306. Blood may flow along flow path FP2 from the vein of a patient through inlet duct 346 and past inlet port 348 into interior cavity 342 of housing 306 adjacent the bottom portion of body 328 of flow control insert 304. The blood may then travel up flow control insert 304 by flowing within inlet fluid channel 332 of insert 304 and past annular protrusion 330 of insert 304. The blood may then travel along annular protrusion 330 of insert 304, within the track of tapered groove 324 of flow control dial 302, and then the blood may be forced through slot 360 of housing 306. In this manner, the blood is forced to step through slot 360 before flowing out flow orifice 352 of housing 306.

As described above, during blood collection, system 300 allows a medical clinician to manually vary the flow of blood from the vein of a patient and through system 300 based on the condition of the patient. For example, the medical clinician may determine that the flow rate should be reduced even farther below the flow rate with the system in the position of FIGS. 18A and 18B. Accordingly, the clinician may rotate flow control dial 302 in a direction generally along arrow A to the position shown in FIGS. 19A and 19B. In this manner, the flow rate is reduced to a level below the flow rate with the system in the position of FIGS. 18A and 18B as will now be described. FIGS. 19A and 19B illustrate flow control dial 302 in an exemplary position and it is contemplated that flow control dial 302 may be rotated to any of a plurality of positions relative to housing 306. In this manner, flow regulator system 300 allows for precise control of the flow rate of a fluid through system 300.

Rotation of flow control dial 302 to the position shown in FIGS. 19A and 19B causes the effective cross-sectional area of slot 360, which is determined by slot 360 and the helical shoulder of flow control dial 302, to be reduced. In this manner, the blood is forced to step through slot 360 before flowing out flow orifice 352 of housing 306. Because the effective cross-sectional area of slot 360 is reduced with flow control dial 302 in the position shown in FIGS. 19A and 19B, the flow rate of a fluid through system 300 is reduced to a level below the flow rate of a fluid with the system 300 in the position shown in FIGS. 18A and 18B. In other words, with system 300 in the partially open flow position shown in FIGS. 19A and 19B, the flow path FP of a fluid, such as blood, through flow regulator system 300 is the same as described above except that the blood is forced to step through slot 360 having a reduced effective cross-sectional area which thereby reduces the flow rate of the fluid within system 300.

In one procedure, initially a medical clinician will set a position of flow control dial 302 so that flow regulator system 300 is in a reduced flow position, as will be described in more detail below, so that the flow rate of the blood is reduced to counteract the strong vacuum effect upon initial access of the evacuated tube. The medical clinician may then increase the flow rate of the blood through flow regulator system 300 to allow better flow once initial draw is equalized.

In the manner described above for system 300, rotation of flow control dial 302 in a direction generally along arrow A from the maximum flow position (FIGS. 17A and 17B) allows the flow rate to be modulated.

In some embodiments, system 300 may allow for precise, incremental control of the flow rate of a fluid, such as blood, through system 300. In other embodiments, profile 324 may include a stepped or other configuration to allow for incremental adjustment of system 300.

Figure 20B:
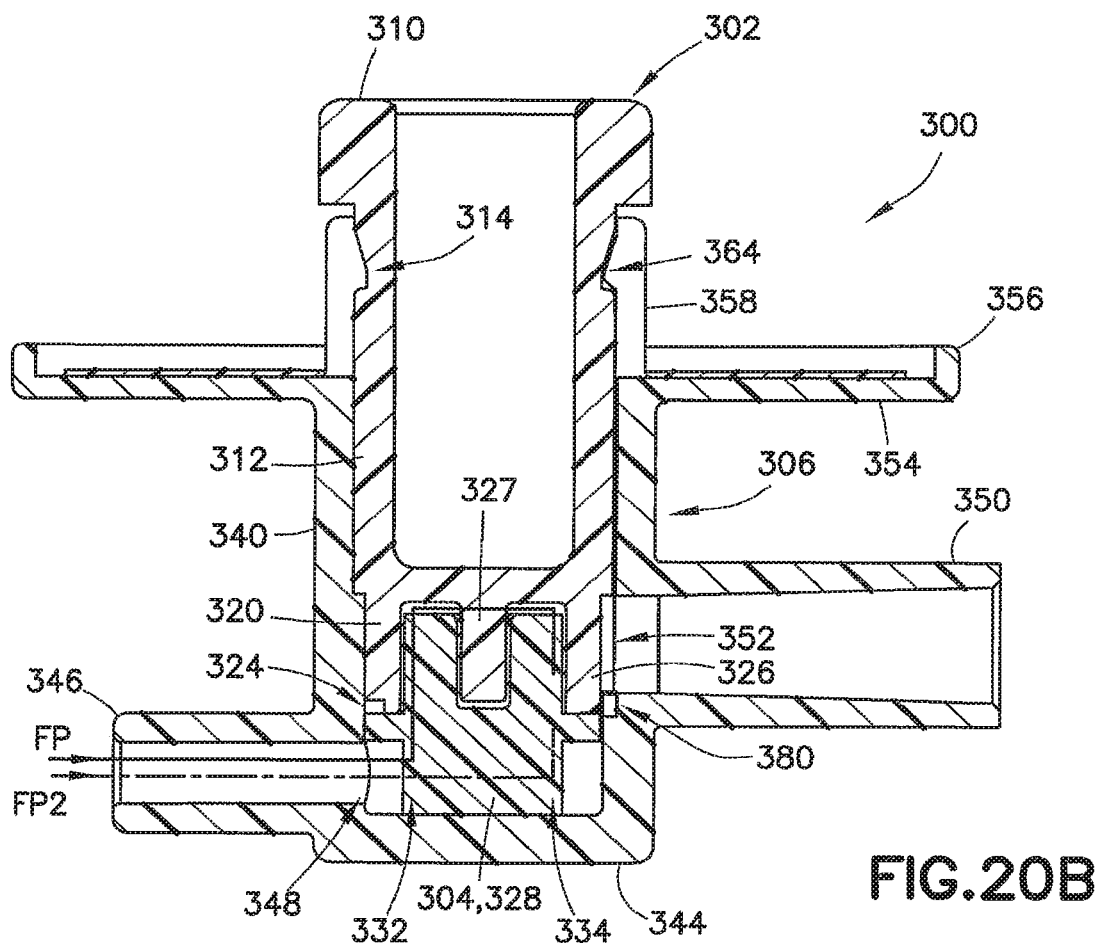
FIG. 20B is a cross-sectional view taken along line 20B-20B of FIG. 20A in accordance with an embodiment of the present invention.

As described above, during blood collection, system 300 allows a medical clinician to manually vary the flow of blood from the vein of a patient and through system 300 based on the condition of the patient. For example, the medical clinician may determine that the flow rate should be shut off. Accordingly, the clinician may rotate flow control dial 302 in a direction generally along arrow A (FIG. 19A) to the position shown in FIGS. 20A and 20B. FIGS. 20A and 20B illustrate flow control dial 302 in an exemplary position and it is contemplated that flow control dial 302 may be located in other positions, and system 300 configured accordingly, and the system 300 may be in a fully closed position.

Rotation of flow control dial 302 to the position shown in FIGS. 20A and 20B causes aperture blocking portion 326 of flow control dial 302 to rotate in the direction generally along arrow A (FIG. 19A) such that aperture blocking portion 326 is placed in alignment with flow orifice 352 of housing 306 as shown in FIG. 20B. In the position of FIGS. 20A and 20B, aperture blocking portion 326 provides a physical barrier that blocks the entirety of flow orifice 352 of housing 306 and thus prevents any blood from flowing past flow orifice 352.

As described above, during blood collection, system 300 allows a medical clinician to manually vary the flow of blood from the vein of a patient and through system 300 based on the condition of the patient. For example, from the fully closed position of FIGS. 20A and 20B, the medical clinician may determine that the flow rate should be turned back on. Accordingly, referring to FIG. 20A, the clinician may rotate flow control dial 302 in a direction generally along arrow B to open flow orifice 352 in the manner as described above. In this manner, the clinician may rotate flow control dial 302 in the direction generally along arrow B (FIG. 20A) to incrementally or linearly move system 300 from the position shown in FIGS. 20A and 20B to the position shown in FIGS. 17A and 17B (maximum flow position) and to all positions in between. Similarly, with system 300 in the maximum flow position, the clinician may rotate flow control dial 302 in the direction generally along arrow A (FIG. 17A) to incrementally or linearly move system 300 from the position shown in FIG. 17A to the position shown in FIGS. 20A and 20B and to all positions in between. As described above, flow regulator system 300 allows for precise, incremental, or linear control of the flow rate of a fluid through system 300.

In one embodiment, a protrusion (not shown) may be disposed on the interior wall of interior cavity 342 of housing 306 to form a rotation limiting abutment member for preventing rotation of dial 302 beyond the maximum flow position or the fully closed position. In such embodiments, a portion of dial 302 may protrude out from body portion 312 or extend beyond a bottom surface of flow control portion 320 so that a portion of dial 302 may engage the protrusion disposed on the interior wall of interior cavity 342 of housing 306. In this manner, system 300 is configured so that once dial 302 reaches either the maximum flow position or the fully closed position, a portion of dial 302 engages the protrusion of interior cavity 342 of housing 306 to prevent movement beyond the maximum flow position or the fully closed position.

Figure 22:
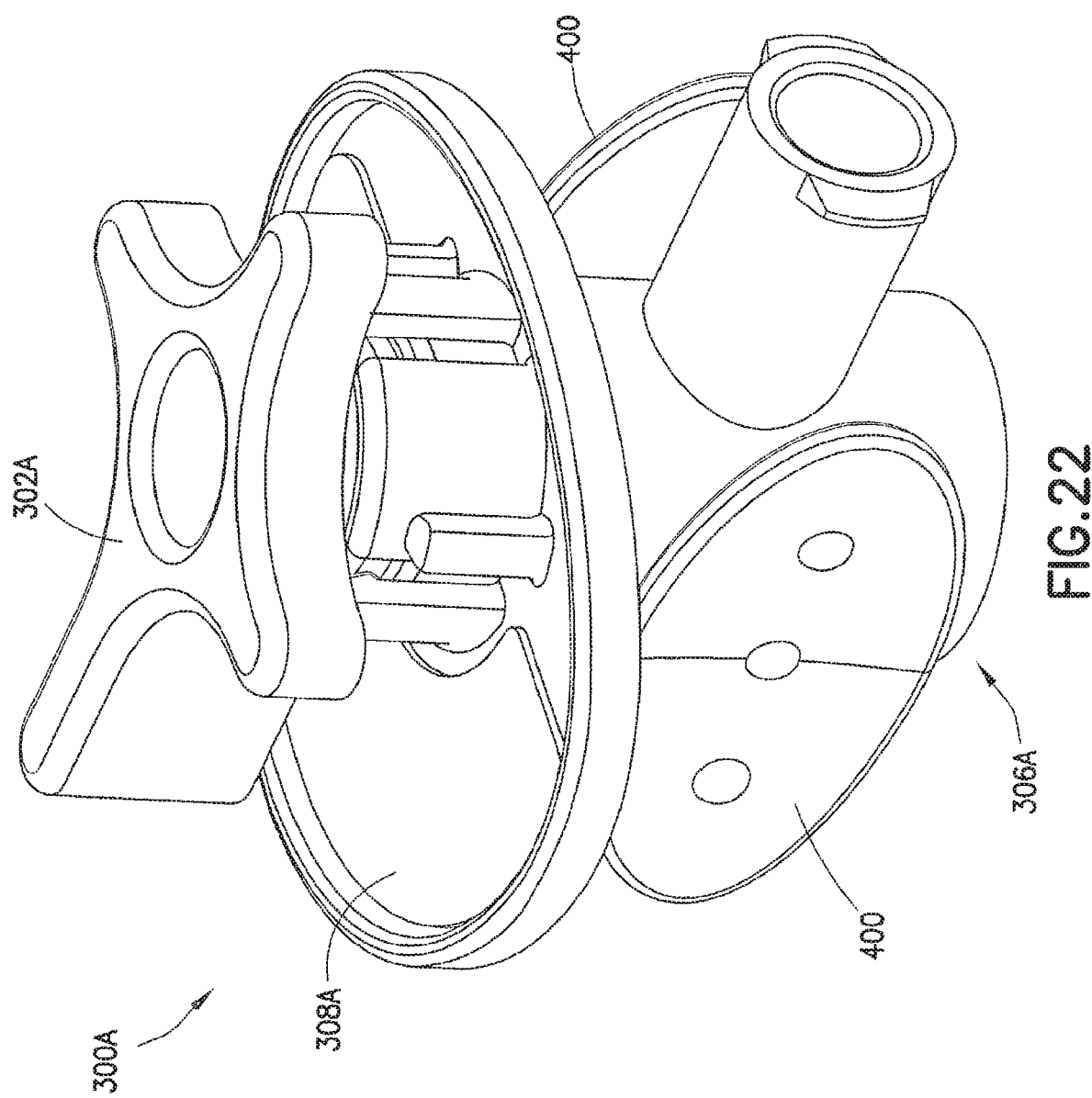
FIG. 22 is an assembled, perspective view of the flow regulator system of FIG. 21 in accordance with an embodiment of the present invention.

FIGS. 21 and 22 illustrate another exemplary embodiment of the present invention. The embodiment illustrated in FIGS. 21 and 22 includes similar components to the embodiment illustrated in FIGS. 14-20B, and the similar components are denoted by a reference number followed by the letter A. For the sake of brevity, these similar components and the similar steps of using flow regulator system 300A (FIGS. 21 and 22) will not all be discussed in conjunction with the embodiment illustrated in FIGS. 21 and 22.

Referring to FIGS. 21 and 22, flow regulator system 300A, having a flow control insert 304A and plate 308A, is used to adjustably alter a flow path in a manner similar to the embodiment shown in FIGS. 14-20B, e.g., the flow of blood coming from the vein of a patient is modulated by manually varying the cross-sectional area of an orifice. In one embodiment, flow regulator system 300A may provide a system that has a smaller and more ergonomic design than the embodiment shown in FIGS. 14-20B. Flow regulator system 300A may also include finger plates 400 disposed on opposing sides of housing 306A. In this manner, a user is provided with a place to more easily hold housing 306A while rotating flow control dial 302A in a direction generally along arrow B (FIG. 20A) to open a flow orifice as described above.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A specimen collection assembly comprising:
a cannula defining a lumen therein;
a housing having a housing wall defining an internal chamber having an inlet port and an outlet port, the inlet port adapted for fluid communication with the lumen, the outlet port adapted for fluid communication with an evacuated collection container; and
a flow control member cooperating with the housing, the flow control member having a flow control portion defining an open flow recess, the flow control portion being rotatable to position the open flow recess in and out of alignment with a flow orifice within the housing to vary an effective cross-sectional area of at least one of the inlet port and the outlet port.

2. The specimen collection assembly of claim 1, wherein the flow control member is manually adjustable to alter the effective cross-sectional area.

3. The specimen collection assembly of claim 1, further comprising a flow control insert disposed at least partially within the internal chamber and configured to cooperate with the flow control member to direct flow from the inlet port to the outlet port.

4. The specimen collection assembly of claim 1, wherein the flow control member includes a tapered groove disposed about a central axis of the flow control member and terminating in an aperture blocking portion, wherein upon rotation of the flow control member, the aperture blocking portion is configured to vary an effective cross-sectional area of at least one of the inlet portion and the outlet port and/or is configured to open or close at least one of the inlet portion or outlet port.

5. A specimen collection assembly comprising:
a cannula defining a lumen therein;
a housing having a housing wall defining an internal chamber having an inlet port and an outlet port, the inlet port adapted for fluid communication with the lumen, the outlet port adapted for fluid communication with an evacuated collection container; and
a flow control member cooperating with the housing, the flow control member having a flow control portion defining an open flow recess, the flow control portion being rotatable to position the open flow recess in and out of alignment with a flow orifice within the housing to vary an effective cross-sectional area of at least one of the inlet port and the outlet port, wherein the flow control member is rotatable between a maximum flow position and a minimum flow position.

6. A specimen collection assembly comprising:

a cannula defining a lumen therein;

a housing having a housing wall defining an internal chamber having an inlet port and an outlet port, the inlet port adapted for fluid communication with the lumen, the outlet port adapted for fluid communication with an evacuated collection container; and a flow control member cooperating with the housing, the flow control member having a flow control portion defining an open flow recess, the flow control portion being rotatable to position the open flow recess in and out of alignment with a flow orifice within the housing to vary an effective cross-sectional area of at least one of the inlet port and the outlet port, wherein the flow control portion includes a helical profile disposed about a central axis of the flow control member, wherein, upon rotation of the flow control member, the helical profile is configured to open or close at least one of the inlet port and the outlet port.

7. A method of regulating blood flow in a blood collection assembly comprising:

establishing fluid communication between a patient vasculature and an evacuated collection container; and regulating blood flow from the patient vasculature by varying an effective cross-sectional area of at least one of an inlet port and an outlet port defined in a portion of a blood collection assembly housing provided in fluid communication with the patient vasculature, wherein regulating the blood flow is achieved by providing a rotatable flow control member cooperating with the housing, the flow control member having a flow control portion defining an open flow recess, the flow control member being rotatable to position the open flow recess in and out of alignment with a flow orifice within the housing.

8. The method of claim 7, wherein the regulating blood flow occurs by manually varying the effective cross-sectional area of the at least one of the inlet port and the outlet port.

9. The method of claim 7, wherein the flow control member is rotatable between a maximum flow position and a minimum flow position.

* * * * *